United States Patent
Shevitz

(10) Patent No.: US 9,446,354 B2
(45) Date of Patent: Sep. 20, 2016

(54) DEVICE, SYSTEM AND PROCESS FOR MODIFICATION OR CONCENTRATION OF CELL-DEPLETED FLUID

(75) Inventor: Jerry Shevitz, Livingston, NJ (US)

(73) Assignee: Repligen Corporation, Waltham, MA (US)

( * ) Notice: Subject to any disclaimer, the term of this patent is extended or adjusted under 35 U.S.C. 154(b) by 698 days.

(21) Appl. No.: 13/408,243

(22) Filed: Feb. 29, 2012

(65) Prior Publication Data

US 2013/0059371 A1   Mar. 7, 2013

Related U.S. Application Data

(63) Continuation-in-part of application No. PCT/US2011/001485, filed on Aug. 24, 2011.

(60) Provisional application No. 61/376,810, filed on Aug. 25, 2010.

(51) Int. Cl.
*B01D 61/58* (2006.01)
*B01D 63/02* (2006.01)
*C12M 1/00* (2006.01)

(52) U.S. Cl.
CPC .............. *B01D 61/58* (2013.01); *B01D 63/02* (2013.01); *C12M 29/16* (2013.01); *C12M 29/18* (2013.01); *B01D 2313/13* (2013.01); *B01D 2313/243* (2013.01)

(58) Field of Classification Search
CPC ............... B01D 2313/13; B01D 2313/243; B01D 61/58; B01D 63/02; C12M 29/16; C12M 29/18
See application file for complete search history.

(56) References Cited

U.S. PATENT DOCUMENTS

| | | |
|---|---|---|
| 2,751,084 A | 6/1956 | Wilhelm |
| 4,256,583 A | 3/1981 | Lennartz |
| 4,806,484 A | 2/1989 | Petrossian |
| 4,844,804 A * | 7/1989 | Taylor ................ 210/321.8 |
| 5,055,198 A | 10/1991 | Shettigar |
| 5,106,501 A | 4/1992 | Yang et al. |
| 5,286,646 A | 2/1994 | Kearns |
| 5,563,068 A | 10/1996 | Zhang et al. |

(Continued)

FOREIGN PATENT DOCUMENTS

| | | |
|---|---|---|
| EP | 715875 | 6/1996 |
| JP | H05-505540 | 8/1993 |

(Continued)

OTHER PUBLICATIONS

Brain, M., Kidney dialysis machines clean toxins from blood. McClatchy-Tribune, Saturday, Apr. 18, 2009.

(Continued)

*Primary Examiner* — Nathan Bowers
*Assistant Examiner* — Lydia Edwards
(74) *Attorney, Agent, or Firm* — Fish & Richardson P.C.

(57) ABSTRACT

A product concentration device that utilizes a reservoir connected to a hollow-fiber filter element where the reservoir can serve as a container for filtrate emanating from another filtering device, such that product in the reservoir can be stored, concentrated and/or further processed as desired. Enclosed reactor systems, each of at least three chambers, fluid flow between the chambers controlled by selectively permeable barriers, flow controlled by an alternating flow diaphragm pump.

34 Claims, 19 Drawing Sheets

(56) References Cited

U.S. PATENT DOCUMENTS

| | | | |
|---|---|---|---|
| 5,712,154 | A | 1/1998 | Mullon et al. |
| 5,811,259 | A | 9/1998 | Hall |
| 6,051,131 | A | 4/2000 | Maxson |
| 6,139,727 | A | 10/2000 | Lockwood |
| 6,544,424 | B1 | 4/2003 | Shevitz |
| 6,555,005 | B1 | 4/2003 | Zha |
| 2003/0121858 | A1 | 7/2003 | Yu |
| 2003/0222006 | A1 | 12/2003 | Cella |
| 2004/0200768 | A1* | 10/2004 | Dannenmaier et al. ... 210/321.6 |
| 2004/0211726 | A1 | 10/2004 | Baig |
| 2004/0222156 | A1 | 11/2004 | Yu |
| 2010/0078395 | A1* | 4/2010 | Shevitz .................. 210/808 |

FOREIGN PATENT DOCUMENTS

| | | |
|---|---|---|
| JP | H11-104412 | 4/1999 |
| JP | 2001-510396 | 7/2001 |
| WO | WO 2010/036338 | 4/2010 |
| WO | WO 2013/130176 | 9/2013 |

OTHER PUBLICATIONS

Xia, S., Removing parathyroid hormone by immunoadsorption at kidney dialysis: an in silico and in vitro investigation for elimination of PTH by immunospecific adsorption for kidney failure patients. TribLive Lifestyles, May 31, 2009 (Abstract Only).

Office Action issued in CN201180051283.7 on Dec. 29, 2014 (13 pages).

Japanese Office Action in Japanese Application No. 2013-525895 dated May 26, 2015, 8 pages.

European Search Report in European Application No. P11820281.1, dated Jun. 25, 2015, 4 pages.

European Search Report in European Application No. 13755349.1, dated Oct. 2, 2015, 3 pages.

International Preliminary Report on Patentability issued in International Application No. PCT/US2009/005288, dated Mar. 29, 2011, 7 pages.

International Search Report and Written Opinion issued in International Application No. PCT/US2009/005288, dated Nov. 23, 2009, 9 pages.

IPER of Nora Linder dated Mar. 29, 2011; 7 pages.

Japanese Office Action in Japanese Application No. 2013-525895, dated Mar. 29, 2016.

Korean Office Action in Korean Application No. 10-2011-7009234, dated Feb. 18, 2016, 8 pages (English Translation).

* cited by examiner

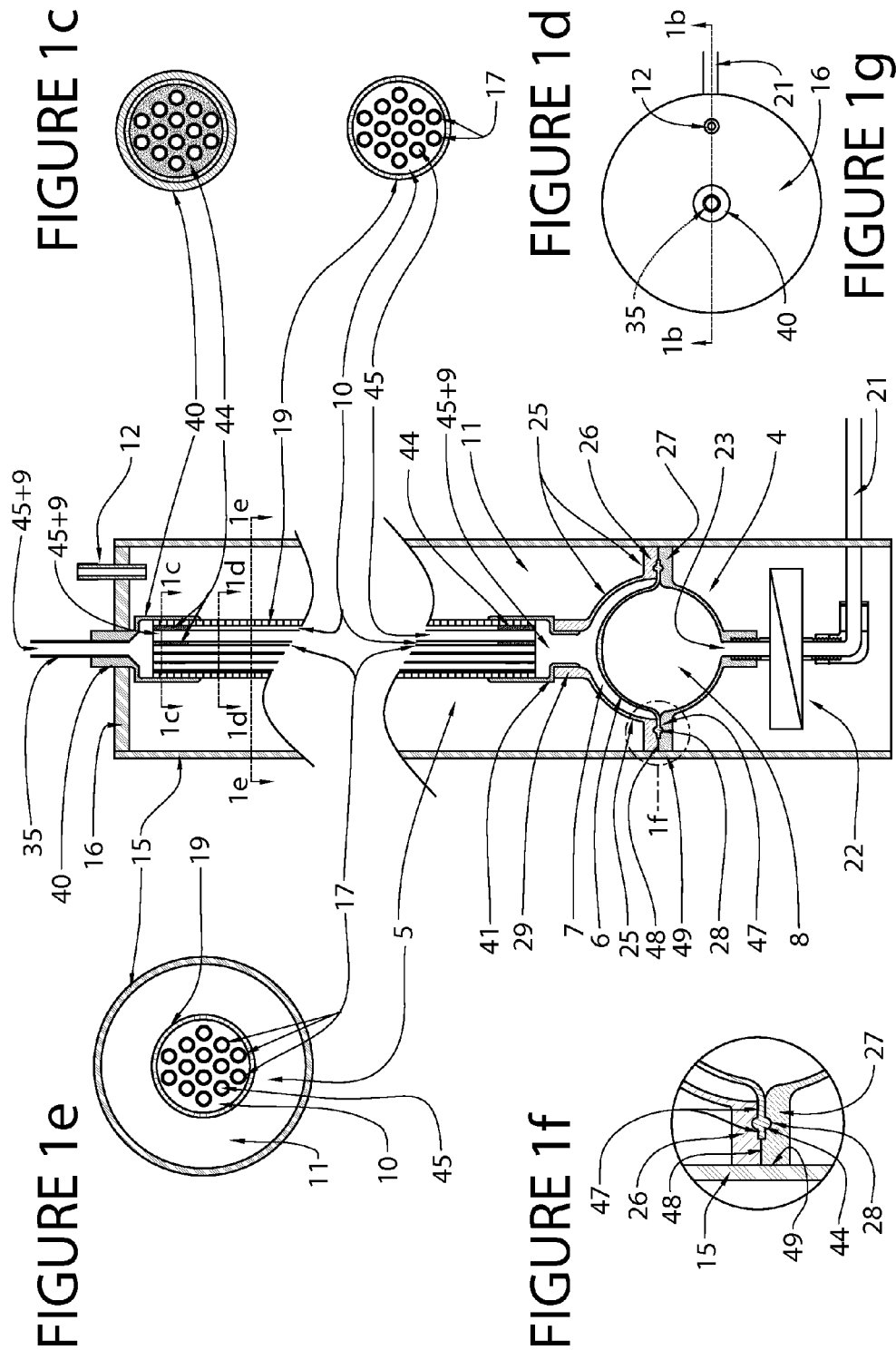

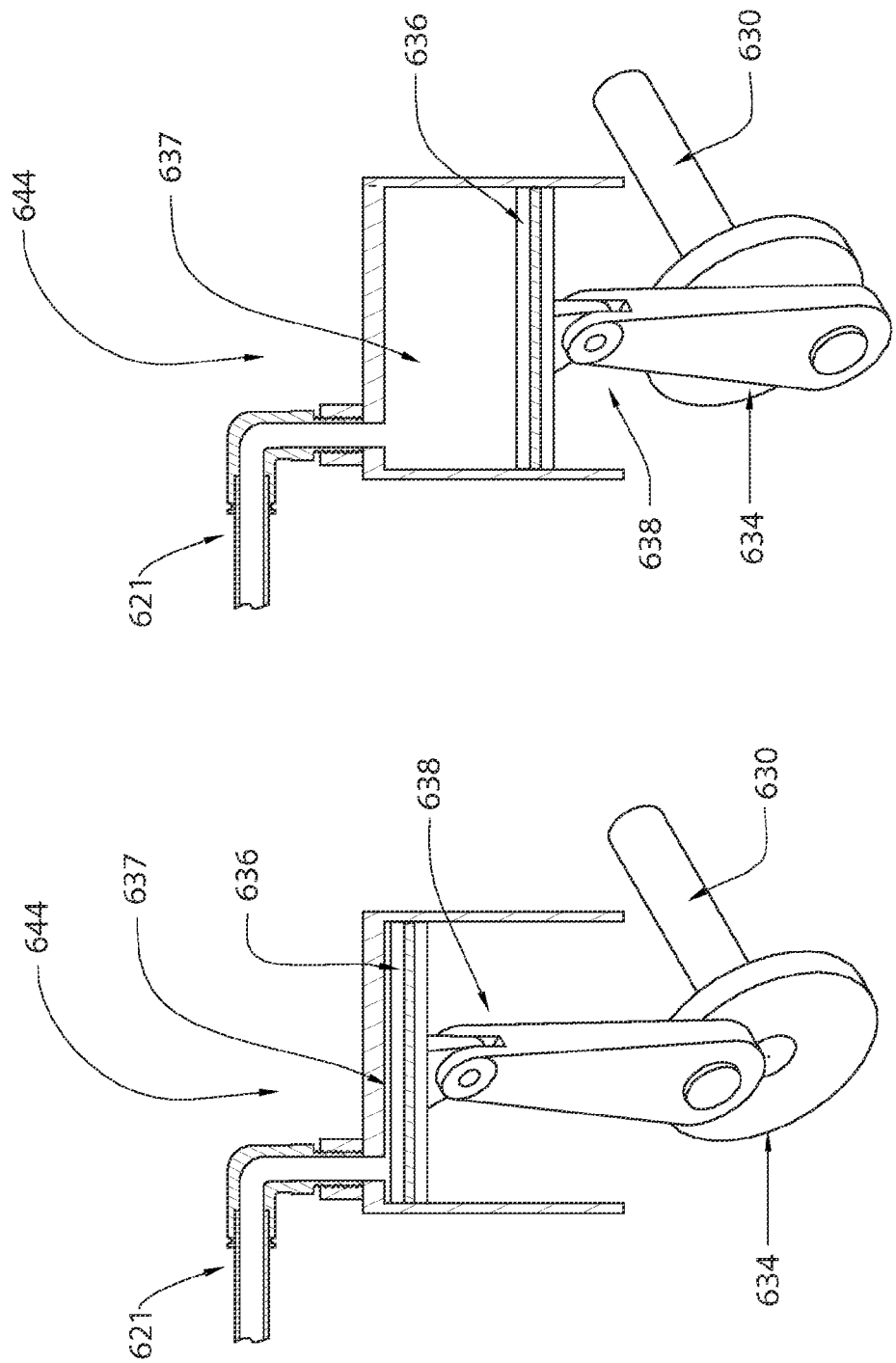

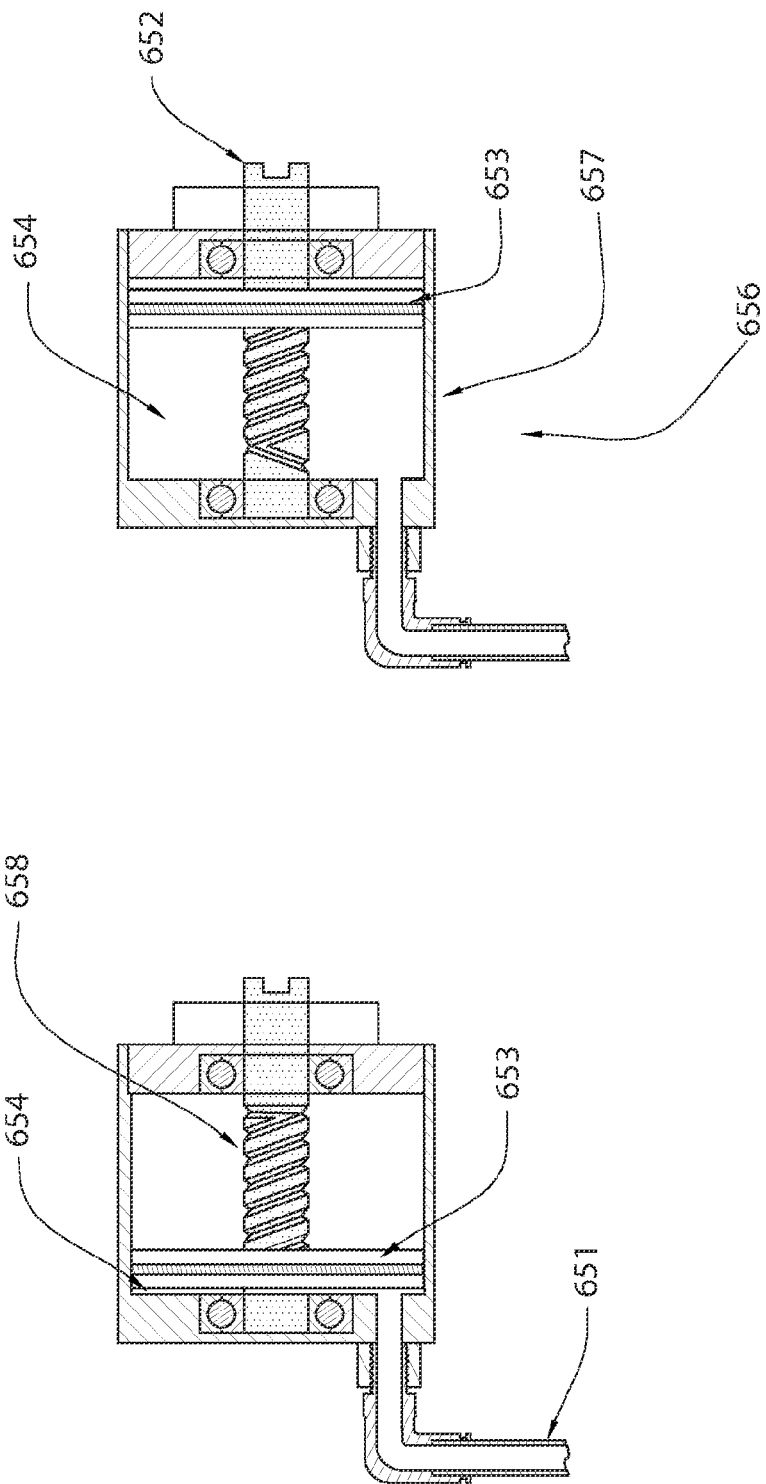

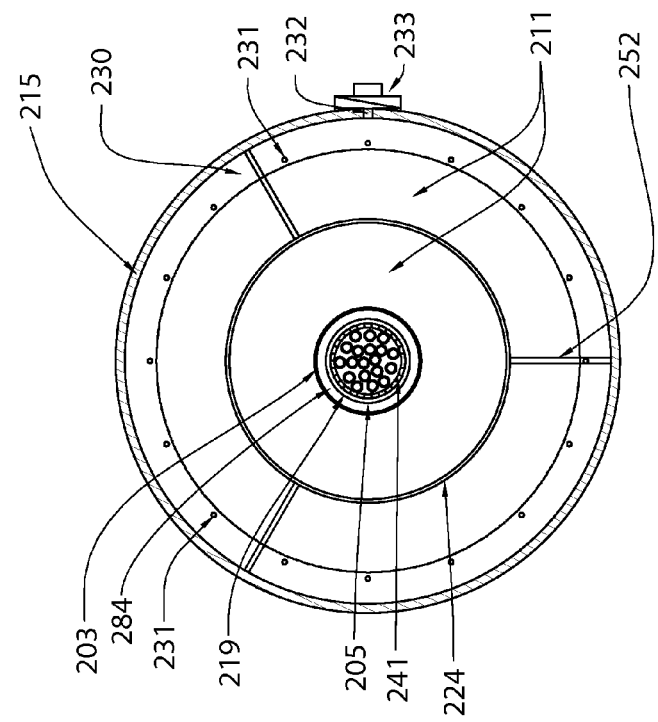
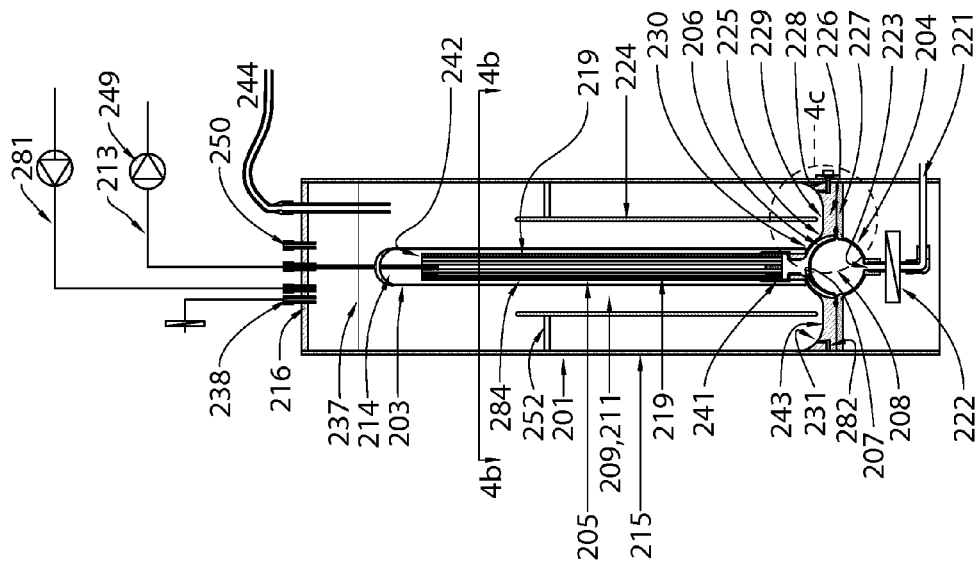
FIGURE 4b
FIGURE 4a

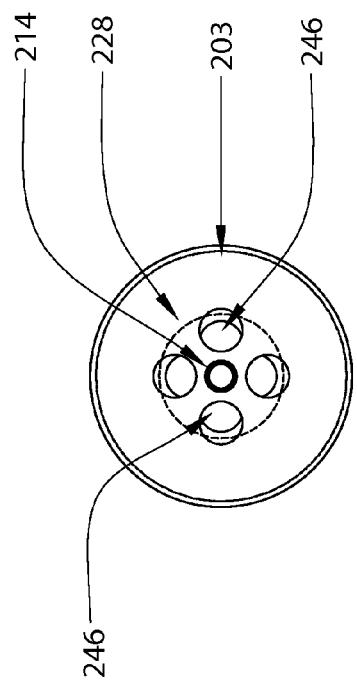
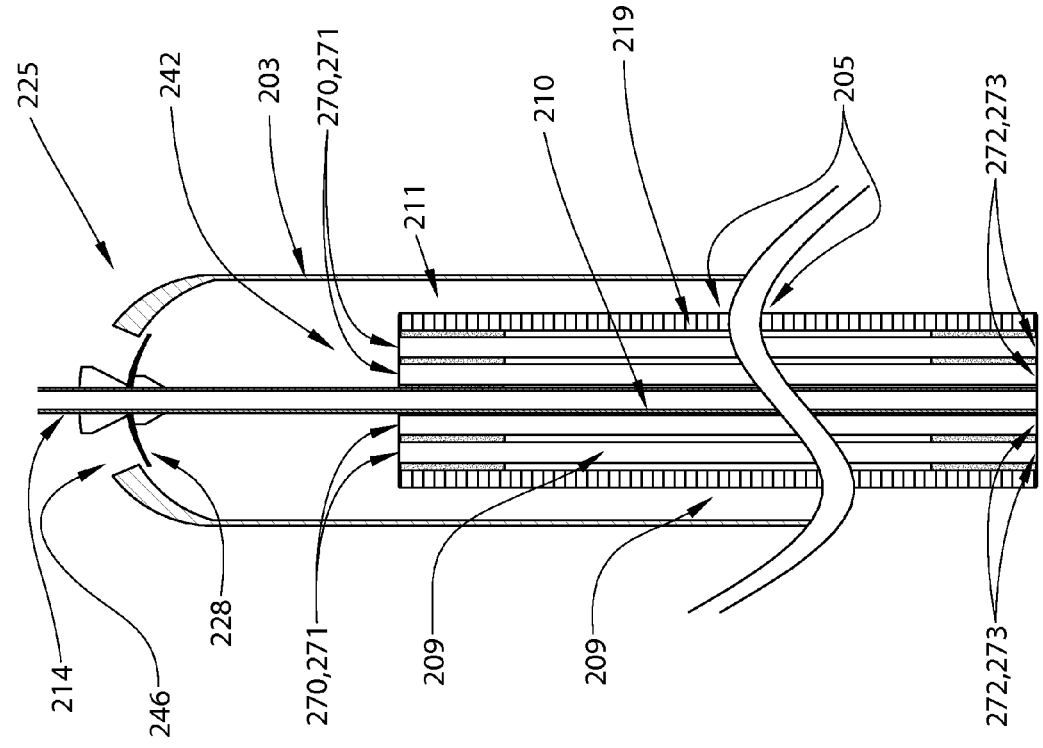

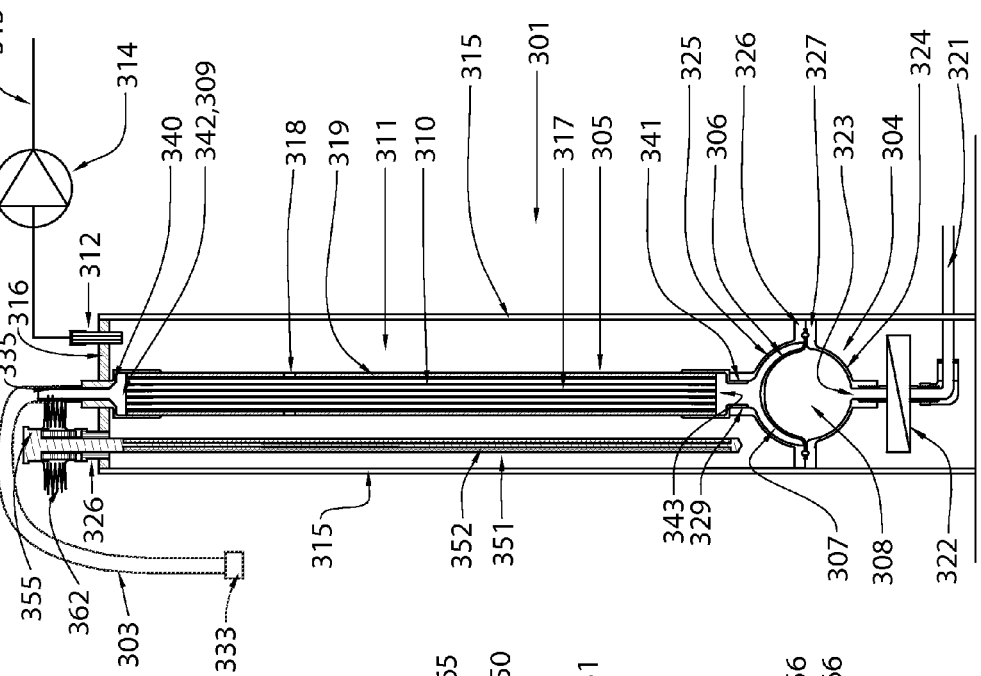
FIGURE 6a
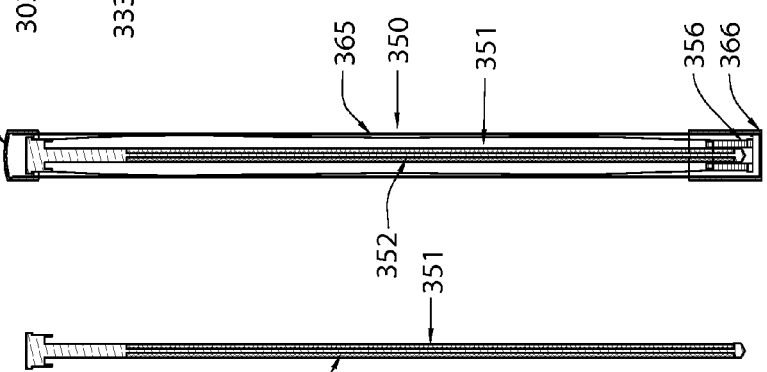
FIG. 6b
FIG. 6d
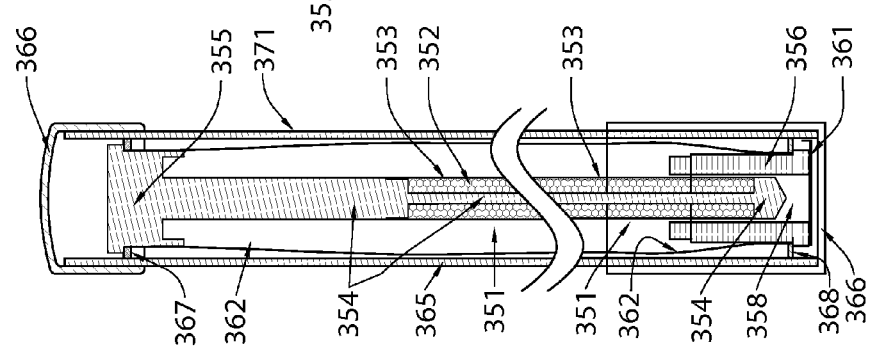
FIGURE 6c

DEVICE, SYSTEM AND PROCESS FOR MODIFICATION OR CONCENTRATION OF CELL-DEPLETED FLUID

CROSS REFERENCE TO OTHER APPLICATIONS

This application is a Continuation-In-Part (CIP) of PCT Application No. PCT/US2011/001485, filed on Aug. 24, 2011, which claims the benefit of U.S. provisional application Ser. No. 61/376,810 filed Aug. 25, 2010. The contents of the above PCT application are incorporated herein by reference.

FIELD OF INVENTION

The present invention relates to filtration systems. More specifically, the invention relates to filtration systems for biological fluids and products, as well as sampling manifolds, pump systems, and modifying modules useful in such systems.

BACKGROUND

Filtration is typically performed to separate, clarify, modify and/or concentrate a fluid solution, mixture or suspension. In the biotechnology pharmaceutical and medical industries, filtration is vital for the successful production, processing and analysis of drugs, diagnostics, chemicals as well as many other products. As examples, filtration may be used to sterilize fluids or gases, clarify a complex suspension into a filtered "clear" fraction and an unfiltered fraction; similarly, constituents in a suspension may be concentrated by removing or "filtering out" the suspending medium. Further, with appropriate selection of filter material, filter pore size or other filter variables, many other specialized filter uses have been developed; these may involve selective isolation of constituents from various sources, including, cultures of microorganisms, blood, as well as other fluids that may be solutions mixtures or suspensions. With further advancements in cell and recombinant DNA technologies many new products are being developed, many of which are so complex that they can only be produced by the complex synthetic machinery of live cells, using cell culture techniques. Filtration may be used to enhance the productivity of such cell cultures; by maintaining the cultures for extended periods at high cell concentrations at high productivity and by providing a product stream more amenable to further processing and purification.

Filter chemistries, configurations and modalities of use have been developed to facilitate separation of materials according to their chemical and physical properties; In spite the extensive developments in filter technology, they are generally limited by their tendency to clog; for example, when used to filter a suspension of cultured mammalian cells they tend to clog with dead cells, cell debris, aggregates, fibrous biomolecules or other constituents found in the complex "soup" of a culture. In this regard, the method of filtration can have a profound effect on the filtration efficiency and the longevity of the membrane. In one kind of filtration process, commonly known as "dead end" filtration, the entire fluid is passed through the membrane perpendicular to the membrane surface. Debris rapidly accumulates at the surface resulting in rapid blockage of the membrane. Typically, application using dead end filtration involves small samples. The process is simple and relatively inexpensive. Another filtration process, generally known as Tangential Flow Filtration (also known as TFF) offers an improvement over dead end filtration. In TFF, fluid to be filtered is recirculated with a pump, typically, from a reservoir through a filter and back to the reservoir. The flow through the filter is parallel to the surface of the filter. Any accumulation of debris is effectively removed by the "washout" effect of the circulating fluid; nevertheless, one of its limitations is the tendency to form a gelatinous deposit on the filter surface, which may limit the effectiveness of the filter and eventually clogging it. Another processes, known as alternating tangential flow filtration, offers yet another mode of filtration; It is similar to TFF, in that it generates a flow pattern parallel to the filtration membrane surface; however, it differs from TFF in that the direction of flow is repeatedly alternating or reversing across the filter surface. If a change in flow direction is described using a complex pathway of tubing, valves and pumps, placement of such components in a culture flow path adds sheer to the system and provides sites for cell to aggregate and potential clogging sites, nor are such systems very amenable for sustaining homogeneous cultures. The alternating tangential flow filtration system described in U.S. Pat. No. 6,544,424 consists of a filter element, commonly a hollow fiber cartridge, connected at one end to a reservoir containing the content to be filtered and at the other end the filter its connected to a diaphragm pump capable of receiving and reversibly expelling the unfiltered liquid flowing reversibly between reservoir and pump through the filter element. The system has shown the ability to sustain filtration of a complex mixtures, Including the medium of a cell culture, even when that medium is burdened with high cell concentration and other cellular products. That system, however, is limited in its range of applications.

The use of animal cell culture is increasingly used for production of various cell derived biologicals that may be natural or engineered, including proteins, nucleotides, metabolites and many others. Accordingly, methods of production may also vary. They may range from the use of "simple" batch to continuous processes. In a normal batch culture production processes, cells are first inoculated into a fresh medium, after which the cells rapidly enter a logarithmic growth phase. As they consume the nutrients in the medium, waste products accumulate; concomitantly, cells transition from rapid growth to a stationary growth phase followed by a cellular decay phase. While several methods have been developed to optimize batch culture production, in each case, these processes undergo rapid growth and decay cycles. Another culture process involves maintenance of the culture continuously using a process commonly known as perfusion. In a perfusion culture, waste products generated by the cells are continuously removed from the culture, while retaining the cells. Removed waste medium is replenished with fresh medium. With this method, it is possible, therefore, to achieve a state of equilibrium in which cell concentration and productivity are maintained. Typically, about one to two culture volumes are exchanged per day and the cell concentration achieved in perfusion is typically 2 to more than 10 times that achieved at the peak of batch culture. Yet, in spite of the great benefits of the perfusion process, its acceptance has been slow. One reason for this slow acceptance may be inherent in the fact that most products originate at small scale in a batch culture system, like a "T" flask. If more material is needed, it is generally produced by increasing the number and size of the "T" flasks or transferring the culture to roller bottles or spinner flasks, both of which are typically also batch cultures by nature. By the time the culture is scaled to a bioreactor, the process has been largely biased by the previous handling of the culture. It would therefore be desirable to create a disposable perfusion system that is more accessible at small scale, at the level of research and development. Attempts to address this issue with hollow fiber bioreactor or other solid bed bioreactor, in which the cells grow attached or entrapped to a fixed surface, are only partially effective; their inherent inhomogeneity and inaccessibility to the cells limits their usefulness as a research tool. It would desirable to create a system that is easily scaled down, that would maintain cultures homogeneously in continuous perfusion, such that sampling, modifying or monitoring any part of the culture will reflect the conditions in the entire culture. An investigator may tap into such a continuous culture as the need arises for cells, for analysis or for a desired product to study the behavior of the cells in a continuous steady state culture. An investigator can make essential modifications to such a culture followed by observing the cultures response. In addition to proving a means for generating product, such a continuous culture may offer a powerful research and development tool. The proposed invention addresses this issue by providing a perfusion bioreactor system, that maintains a homogenous culture which is accessible to manipulation, sampling and analysis. The proposed system may be provided in a convenient sterile form ready for use and readily disposable.

With advancements in new materials, manufacturing methods and requirements in recent years, the construction and use of disposable equipment has gained increasing acceptance. The use of disposable bags as cell culture bioreactors and storage vessels has become more common. Such disposable containers can be "set-up" with minimal handling and do not require cleaning or sterilization by the user. They are supplied clean, sterile and in a form ready for use, at great savings in cost and reduced handling by the user; furthermore, at the end of their use, the bags can be readily discarded without disassembly or cleaning. The disadvantage of the bags lies in their inherent fragile nature, limiting their size; although, significant progress has been made in the construction of large disposable bags. Another disadvantage of the bags is the limited ability to agitate or mix the culture. Linear scale up of mixing is difficult to sustain with increasing bag size. While the bag volume increases by the cube, the surface area of the culture head space increases by the square; oxygen transfer becomes limiting as is growth and cell productivity. There are also limitations on monitoring the conditions of the culture with pH, oxygen or other probes, factors which can profoundly effect the reproducibility of the culture and limit its achievable cell concentration and productivity. Considerable progress has been made by some bag manufacturers to solve the problem of agitation by incorporating an impeller into the bag, additionally, means for sampling, monitoring and making changes to the culture within a bag are being developed; in spite these developments, however, these bags are used to grow cells in batch or fed batch.

It would be, therefore, desirable to incorporate a device that would enhance the productivity of disposable bags or similar systems and alleviate some of their shortcomings. Some desirable features of such a device may incorporate the following features, including: (i), the ability to facilitate mixing of the culture within the disposable bag, (ii), the ability to retain cells and sustain the culture in continuous perfusion mode, (iii), include the capacity to be used externally so that it may be replaced in mid process with minimum disruption to the process, including maintaining process sterility, (iv), remain fully or partially disposable in nature. One can envision the alternating tangential flow filtration system described in U.S. Pat. No. 6,544,424 as encompassing the above requirements as well as a disposable system, since in its description the device was not limited to construction material nor to its methods of assembly; however, the system in U.S. Pat. No. 6,544,424 does not describe a system that may be used as a complete culture system, eg, a system that incorporates or combines the culture vessel and the perfusion device into a single apparatus. The current invention, as will be described, may be used as such an apparatus that, in addition to providing a means for continuous culture, may be fully disposable, and also offers other benefits and uses.

Changing pressures gradients and flows that are both parallel (axial flow) and perpendicular (transmembrane flow) to the membrane surface are inherent in the alternating tangential flow process. During the "pressure cycle", the pressure in the pump is greater than the pressure in the retentate reservoir. The retentate flows "forward" from the diaphragm pump, i.e., through the filter element towards the retentate reservoir. Also, some of the liquid is forced across the filter membrane into the filtrate compartment. Therefore, with an enclosed filtrate compartment, the influx of filtrate can pressurize the filtrate compartment. Conversely, during the "exhaust, cycle" of the alternating tangential flow filtration process, the pressure in the pump is less than that in the retentate reservoir, so that liquid flows in reverse, from reservoir to pump. Additionally, during the exhaust cycle, filtrate compartment fluid pressurized during the previous pressure cycle will also flow in reverse, from the filtrate compartment to the retentate compartment. The backflow produces a back flush component that maintains the membrane and inhibits clogging. This effect is further enhanced by another kind of transmembrane flow, one which forms when the resistance to axial flow inside the hollow fiber, or lumen side, is greater than in the external, shell, side of the hollow fiber. Therefore, during the pressure cycle pressurized fluid forced into the inlets of the hollow fibers will take the path of least resistance, or in proportion to the resistance, and the fluid will flow not only through the lumens, but also in part across the membrane, into the filtrate or shell side, as previously described. An axial pressure gradient forms on both sides of the filter causing fluid flow towards the exit end of the filter. Towards the exit end of the hollow fiber, the lumen pressure decreases towards its minimum. The pressure drop inside the lumen relative to the shell side results in filtrate reentry into the lumen or retentate stream, on its way to the retentate reservoir. The flow from the filtrate side back into retentate side provides additional back flushing. It is obvious that such a flow will also be observed during the exhaust cycle, but in the reverse direction. The process thus provides back flushing capacity at both ends of the filter element. As a result, it is obvious that the described flows offer a great capacity for exchange of fluids between the retentate and filtrate sides. Such exchange can be highly beneficial for processing fluids. It is also the objective of this invention to use this capacity of the alternating tangential flow filtration system for exchanging fluids across a membrane by modifying the configuration of that system in a manner that would result in unique systems and provide great improvement over existing devices, beyond its previous use as strictly a filtration device.

As will be shown, by specific compartmentalization of the alternating tangential flow filtration process, one can produce systems that may greatly improve processing of blood, convert the system into a disposable perfusion bioreactor, facilitate certain biological and chemical reactions or be used for purification or isolation of certain constituents from biological or other fluids. Other processes and uses are also possible as will become apparent.

BRIEF SUMMARY OF THE INVENTION

The enclosed filtration system invention is a system in which a two-chambered filter element is enclosed in a chamber, referred to as a reactor chamber, such that the reactor chamber and one or both filter element chambers are accessible outside the system via their ports The filter element is preferably a hollow fiber filter cartridge in which the internal hollow fiber membranes are semi-permeable and the cartridge outer wall is semi-permeable or fully permeable. In one embodiment, this permits intermediate size molecules or complexes to be collected in the filtrate chamber and even smaller molecules or complexes to be collected in the reactor chamber. Fluid flow is controlled by an alternating flow pump.

The enclosed bioreactor system comprises 3 types of chambers: filtration retentate chambers, a filtrate chamber essentially surrounding the filtration retentate chambers but without blocking their entrance or exit ends, and a processing chamber that essentially surrounds the filtrate chamber but also does not block the entrances or exits of the retentate chambers. The processing chamber provides an enclosed space in which fluid escaping the entrance of the filtration retentate chambers is captured. The only way fluid from the processing chamber can be accessed from outside that chamber is through one or more port in the processing chamber wall. The filtrate chamber and the filtration retentate chambers are separated by the semi-permeable membranes of the filtration retentate chambers, which allow smaller molecules (those small enough to pass through the pores of the membrane) to be moved from the filtration retentate chambers and processing chamber to the filtrate chamber, from which they can be harvested from the system. An alternating flow pump drives fluid in alternating directions through the filtration retentate chambers, back and forth from the reservoir chamber.

The manifold invention is a device that is connectable to a fluid source, such as a bioreactor, fermentor or some other process vessel, and that draws fluid from that source, returns most or all of it to the fluid source; where the direction of fluid flow between source and the manifold is controlled by an alternating flow pump; where the manifold further comprises ports where fluid aliquots can be removed for sampling or for other purposes or added for transport to the fluid source. Optionally, a filter element capable of selecting the fluid's lower molecular weight substances for testing is part of the manifold; furthermore, the manifold contains further ports through which sensors may be added to monitor the fluid flowing within the device; optionally, similar ports with sensors may be added to the manifold to probe the filtrate within the filter element.

The dual pump system invention comprises two pumps in series, at least one of them (the first pump) being an alternating flow diaphragm pump. That first pump, will be connectable, via one of its pump chambers, to the chamber of a bioreactor. That pump will be connected via its other chamber to a first chamber of the second pump of the system. The second pump can also be an alternating flow diaphragm pump, or it can be an alternating flow mechanical pump. The second pump is connectable to a pressure controlling mechanism, generally under electronic power, that alternatingly creates positive and negative pressures that are transmitted to the first pump and, via the first pump, to a bioreactor chamber such as a chamber of an enclosed filtration system or an enclosed bioreactor system. Sensors, such as proximity, mechanical, electronic, optical, position or other devices, may be integrated preferably into the second pump in a manner that indicate the position of the diaphragm in the second pump. With the use of non-elastic coupling between the two pumps, the motion of the diaphragm of the first pump will correspond with the motion of the diaphragm of the second pump.

The modifier module invention is a module designed for use inside filtration and bioreactor systems so as to modify some (or less commonly, all) of the components in the system. The module, preferably columnar in shape, comprises a scaffold and a population of modifier agents, the modifier agent population, that is either homogenous (all agents are the same) or heterogeneous (all agents are not the same). Examples of modifier agents are antibodies or enzymes. The modifier agent population can be bound to the scaffold. In the case where the modifier agent population is not bound to the scaffold, the module further comprises a semipermeable or fully permeable membrane, such that the membrane partially or completely surrounding the scaffold and creates a compartment between the scaffold and membrane, such that while the modifier agent population is retained within the compartment, preferably stacked against the scaffold, constituents from the reactor or processing chamber and can pass in one direction or in both directions across the membrane to interact with the modifying agent(s).

The product concentration device utilizes a reservoir connected to a hollow-fiber filter element where the reservoir can serve as a container for filtrate emanating from another filtering device, such that product in the reservoir can be stored, concentrated and/or further processed as desired.

BRIEF DESCRIPTION OF THE DRAWINGS

FIG. 1b shows an enlarged sectional view of the enclosed filtration system of FIG. 1a.

FIG. 1c is a sectional view of the filter element and filter element adapter of the enclosed filtration system of FIG. 1b, taken along the line 1c-1c in FIG. 1b.

FIG. 1d is a sectional view of the filter element of the enclosed filtration system of FIG. 1b, taken along the line 1d-1d in FIG. 1b.

FIG. 1e is a sectional view of the enclosed filtration system of FIG. 1b, taken along the line 1e-1e in FIG. 1b.

FIG. 1f is an enlarged sectional view of a portion of the system shown in FIG. 1b.

FIG. 1g is a top view of the enclosed filtration system of FIG. 1b.

FIG. 1h is a partial sectional view of part of the enclosed bioreactor system of FIG. 1a. The view enlarges that part of the system as compared to FIG. 1a.

FIG. 3c shows, in partial cross section and partially in perspective view, an example of a pump usable in a dual pump system. The pump is a piston pump driven by a cam mechanism connected to a motor drive shaft.

FIG. 3d shows the pump of FIG. 3c, but with a different position of the cam and coupled piston.

FIG. 3e shows, in partial cross section and partially in perspective view, an example of a pump usable in a dual pump system. The pump is a piston pump driven by a reversible screw mechanism.

FIG. 3f shows the pump of FIG. 3e, but with a different position of the screw and coupled piston mechanism.

FIG. 4a shows a sectional view of an enclosed bioreactor system of the invention. The reactor chamber of the system is connected to a harvest line FIG. 4b is an enlarged view in cross section of the system in FIG. 4a.

FIG. 4c is an enlarged view in cross section of a portion of the system shown in FIG. 4a.

FIG. 4d shows a sectional view of a portion of the system of FIG. 4 with an added feature corresponding to a puppet valve.

FIG. 4e is a top view of the system of FIG. 4d

FIG. 6a shows sectional view of a fluid filtration system of the invention in which the reactor chamber comprises a modifier module capable of altering the fluid composition in the reactor chamber.

FIG. 6b shows a sectional view of a modifier module in a storage case.

FIG. 6c Shows a sectional view of modifier module in a storage case FIG. 6d shows a sectional view of a modifier module.

DETAILED DESCRIPTION

Figure 1A:
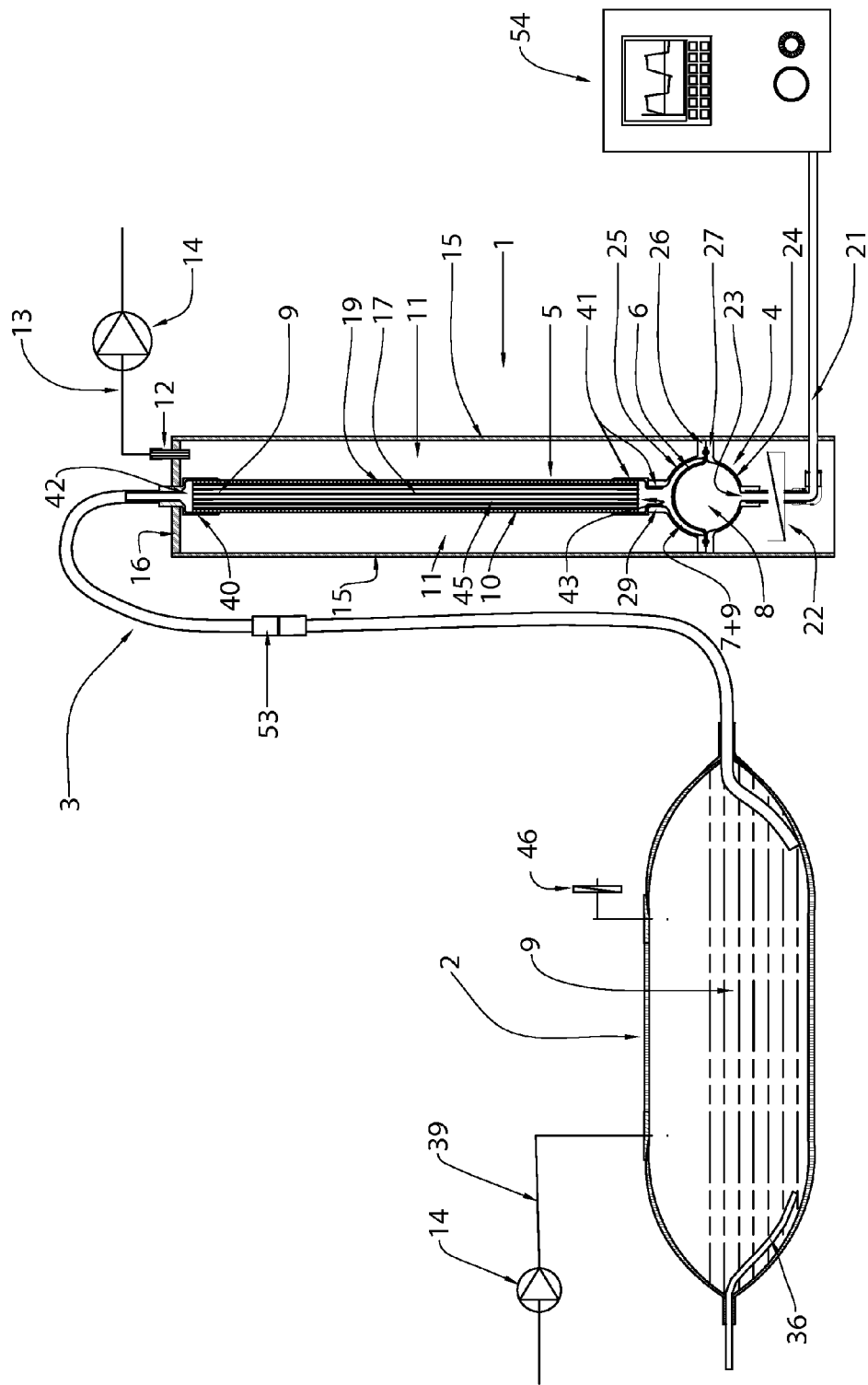
FIG. 1a shows a sectional view of an embodiment of the enclosed filtration system of the invention where the system is connected by a connector line to a storage vessel, also shown in sectional view, and by a connector line to a compressed air controller.

Table of Contents of the Detailed Description:
Detailed description of the enclosed filtration system and process starts: page 16.
Detailed description of the enclosed bioreactor system and process starts: page 40
Detailed description of the manifold system and process starts: page 56.
Detailed description of the dual pump system starts: page 62.
Detailed description of the modifier module system starts: page 76.
Detailed description of the product concentration device, system and process starts: page 85.

Terminology

"Fluid" that is processed by the reactor systems of the inventions are normally aqueous solutions that may or may not comprise suspended particulate matter (such as cells, cell fragments, non-soluble molecular complexes, particles or soluble molecules). The fluid may or may not contain molecules that are dissolved in the fluid.

A "selectively permeable barrier" (or selectively permeable wall) is one that will not allow all particulate matter to pass through it and/or will not allow all dissolved matter to pass through it.

Normally "selectively permeable barrier" is used herein as a descriptor for wall of a hollow fiber that is part of a hollow fiber filter cartridge.

A "selective barrier" is another term used herein for a selectively permeable barrier. Normally "selective barrier" is used herein as a descriptor for the outer wall of a hollow-fiber filter cartridge.

A fully-permeable barrier (or wall) is one that will permit, at one or more openings in the barrier, fluid to pass through it without blocking the passage of any fluid components—either particulate or dissolved.

A fully restrictive barrier does not allow any fluid to pass through it. An opening, such as a harvest port in its open position, must be created in the barrier to allow fluid to move from one side of the barrier to the other.

In the enclosed bioreactor system, the outer wall of the hollow fiber filter cartridge, (i.e., the outer wall of the filtrate chamber) can be selectively permeable, fully permeable, or fully restrictive. Most commonly, it is fully restrictive.

Enclosed Filtration System and Process

The enclosed filtration system (and the enclosed bioreactor system discussed below) employs a retentate chamber and a filtrate chamber. The most convenient way to achieve this is to use a hollow fiber filter. Such a filter is a made as a cartridge that comprises multiple hollow fibers (HF) that run, in parallel, the length of the cartridge and are embedded at each end of the cartridge (preferably with a potting agent); the lumens at the end of the HFs are retained open, thus forming a continuous passage through each of the lumens from one end of the cartridge to the other, i.e., from a cartridge entrance end, to a cartridge exit end. The hollow fibers are enclosed by the outer wall of the cartridge (i.e., the cartridge wall) and a potting layer at their ends. As a result, there is a chamber bounded by the cartridge wall and the outer walls of the HFs. That chamber can be used as the filtrate chamber. The intraluminar (internal) spaces of the HFs are considered collectively to constitute part of the retentate chamber in each of the present systems.

The retentate chamber is extended beyond the internal spaces of the HFs by adapters that fit to each end of the cartridge. Each adapter in conjunction with an end of the cartridge defines a space that is part of the retentate chamber. Depending on the direction of fluid flow through the fibers, that space serves to either (1) collect fluid as it exits the fibers or (2) allow fluid arriving from an external source to interface with the HF open ends and distribute itself among those HFs for purposes of continuing its path towards the other end of the cartridge. Each adapter will have two ends, one end fitted to the cartridge and the other end with an opening connectable to a vessel or a pump. Normally the vessel is connected to the adapter by a line that allows fluid flow but, if desired, the vessel can be connected directly to the adapter or the adapter may form part of the vessel where part or the entire content of the vessel may be contained within the adapter. Normally the adapter is connected directly to a pump but, if desired, the pump can be connected to the pump via a line that permits fluid flow.

When a connecting line is added to an adapter, the retentate chamber is extended to also include the space inside that connecting line.

When a connecting line is connected at one end to an adapter and at its other end to a vessel (e.g., one that contains cells suspended in growth medium), one could consider the interior of the vessel to be a further extension of the retentate chamber, but for purposes of description and discussion herein the vessel and the retentate chamber are referred to as separate entities.

The walls of the lumens of a hollow fiber filter are permeable, conveniently providing a barrier that is either fully permeable or selectively permeable. The selective permeable hollow fiber walls may range in selectivity that ranges the entire gamut of membrane pore sizes, commonly classifies asosmotic membranes, ultrafiltration microfiltration to macrofiltration, where, for example, ultrafiltration range may encompase Molecular Weight cut-offs, in the range from about 10 to about 500 kDa. Pore sizes of 0.2 micron are commonly useful for retaining cells but allowing metabolites and other molecules or molecular complexes pass through the pores. Pore sizes in the range 10 kDA to 500 kDa, are preferred for retaining not only the cells but molecules and molecular complexes larger than the pore sizes.

The outer walls of filter cartridges are often non-permeable and commonly have ports from which filtrate can be drained and/or replaced. For purposes of the enclosed filtration system, however, the filter cartridge comprises an outer wall that constitutes a barrier that is may be non-selective (fully permeable) but is preferably semi-permeable, (not allowing dissolved matter (e.g., molecules and molecular complexes) larger than the pore sizes in the barrier to pass through the barrier and not allowing particulate matter larger than the pore sizes to pass through the barrier). Pore sizes in the range 10 kDA to 500 kDa, are preferred for retaining only molecules and molecular complexes larger than the pore sizes. However, the pore sizes can be made small enough or large enough, so that, respectively, the barrier is highly restrictive, only allowing small salts and their components to pass through or allowing molecules or particles larger than 500 kDa to pass through the membrane. Such membrane selectivity are not only restricted to pore size but to other membrane properties, including: charge, hydrophobisity membrane configuration, membrane surface and pore polarity, etc.

The enclosed filtration system, in its general aspect, is a system that comprises:
1) a retentate chamber, said retentate chamber comprising an entrance at its entrance end and an exit at its exit end, said retentate chamber comprising a retentate chamber wall, at least a portion of said wall being semi-permeable;
2) a filtrate chamber (e.g. the portion of the inside a hollow fiber filter cartridge that is external to the hollow fibers), said filtrate chamber at least partially enclosing said retentate chamber, said filtrate chamber comprising a filter chamber inner wall and a filter chamber outer wall, wherein at least a portion of the filter chamber inner wall corresponds to the semi-permeable portion of the retentate chamber wall; said filtrate chamber outer wall comprising a filtrate chamber outer barrier (possibly fully permeable, but preferably semi-permeable);
3) an alternating flow pump, said pump said pump connected to the perimeter of the retentate chamber exit so as to permit fluid from the pump to enter the retentate chamber and fluid from the retentate chamber to flow into the pump; said pump comprising an outer wall, a diaphragm, and two chambers separated by the diaphragm;
4) a reactor chamber, said reactor disposed so that it at least partially encloses both the filtrate chamber and the retentate chamber in a sealed manner but does not block fluid flow in and out of the retentate chamber entrance, said reactor chamber comprising a reactor chamber inner wall and a reactor chamber outer wall, said reactor chamber inner wall comprising the filtrate chamber outer barrier, said reactor chamber outer wall being sealed to the outside of either the retentate chamber or to the outside of the filtrate chamber, said reactor chamber outer wall optionally sealed to the alternating pump outer wall;
5) a harvest port, said harvest port attached to the reactor chamber outer wall so as to allow fluid to leave or enter the reactor chamber.

As indicated above, one can access the filtrate reservoir through one or more ports to remove filtrate or to make additions to the filtrate in the filtrate chamber.

The terms "sealed", "sealingly" and the like refer to the fact that the juncture or junction of two chambers or other systems components does not permit fluid to leak through the juncture or junction.

The foregoing enclosed filtration system and the variant below where there is a filtrate reservoir are exemplified in the Figures and the detailed discussion of the Figures below.

The enclosed filtration system, in an aspect referred to as the "filtrate reservoir system", may further comprise a filtrate reservoir connected to the filtrate chamber, such that fluid flow directly between that reservoir and the filtrate chamber is permitted. Here, the reactor chamber outer wall is sealed to the outside of the filtrate chamber, but does not enclose the portion of the filtrate chamber that opens into the reservoir. The reservoir encloses the portion of the filtrate chamber that opens into the reservoir. The reservoir is separated from the reactor chamber so that there is no fluid exchange directly between the reservoir and the reactor chamber. In addition to the harvest/addition port(s) connected to the reactor chamber (the first set of port(s)), the system comprises a second set of port(s) which connect to the filtrate reservoir and which extends outside the filtrate reservoir.

The size of the pores in the filtrate chamber outer barrier may be varied depending on the intended use of the system.

In both the enclosed filtration system and the filtrate reservoir system, there may be a second harvest port, that port attached to the filtrate or reservoir chamber so as to allow fluid to leave or enter the filtrate or reservoir chamber.

The diaphragm pump contains two pump chambers and a diaphragm in between. One pump chamber is connected to the retentate chamber so that direction of fluid flow through the retentate chamber may be confine and controlled by the pump. The other pump chamber, the drive chamber, is connected to a source of alternatingly positive and negative pressure.

For the enclosed filtration system and the filtrate reservoir system, a (conduit) connector line will normally be connected to the diaphragm pump's externally connected chamber, or drive chamber, as part of the connection between that chamber and the pressure controller.

For the enclosed filtration system and the filtrate reservoir system, a connector line will normally be connected to the retentate chamber's port. For the enclosed filtration system and the filtrate reservoir system, the line will serve as part of the connection to the external bioreactor, vessel or other containers of retentate.

For the enclosed filtration system and the filtrate reservoir system, additional connector lines and/or harvest lines are used as needed. Many, but not all, such possibilities are illustrated by the examples herein.

Additionally, the enclosed filtration system and the filtrate reservoir system may further comprise additional ports to the retentate, filtrate and/or reactor compartments: for the insertion of probes, instruments or devices, and/or for making additions and subtractions of substances.

Like the alternating tangential flow filtration system, the enclosed filtration system and the filtrate reservoir system provide uniform flow through the entire filter. Also like the alternating tangential flow filtration system, the enclosed reactor systems of the invention may be used with a variety of filter types.

A device that combines the filtrate chamber and the retentate chamber is referred to herein as a "filter element". One filter element that may be used is a hollow fiber (HF) filter, whose use is extensively described herein. They are available in many sizes, configurations, materials, pore sizes, porosity and housings. However, the systems of the invention do not require the use of hollow fiber filters. It is possible to utilize other separation devices. One such device may be a "plate and frame" filter. Another device is a screen module, consisting of a screen mesh as the separation membrane.

It can be seen that the reactor chamber may be used for a variety of functions. For example, it may be used as a permanent or temporary storage reservoir. This makes the content available for various modifications or processing prior to its return to the main process or prior to its harvest.

The enclosed filtration reactor systems of the present inventions (and the enclosed bioreactor systems described below) can be used in additional applications including but not limited to, kidney dialysis, blood processing, water purification concentration, fluid exchange, or various other filtration applications. To illustrate, in the case of kidney dialysis such a situation, the patient's circulatory system can be connected to the retentate chamber. The reactor chamber and/or the filtrate chamber is the source of particular fluid components (electrolytes, biologically active components, adsorptive agents and others) at the concentrations or volumes desired to facilitate the dialysis process. Due to the inherent "lateral" flow during the alternating tangential flow process, fluxes between chambers facilitate rapid equilibration between the compartments. The selectively permeable barrier between the retentate and filtrate chambers may provide one restrictive barrier. Optionally, selective barrier between the filtrate chamber and reactor chamber offer a second restrictive barrier; therefore, the combination of selectivity and rapid equilibration between compartments process offers a more efficient process for removal of undesired or toxic byproducts from circulation i.e., those small enough to pass from the retentate into the filtrate chamber and/or reactor chamber.

It is desirable that enclosed reactor systems of the invention be sterilizable and that, subsequent to sterilization, can be stored sufficiently sealed to prevent subsequent contamination of its interior by external microorganisms or other contaminants that otherwise would enter into the interior of the system subsequent to its sterilization. It is also desirable that these systems are in a configuration and made with construction materials that render the system disposable.

Processes of the Invention Using the Enclosed Filtration Systems

The enclosed filtration system process, in a general aspect, comprises the steps of:
1) discharging fluid from a retentate chamber via a fluid connector into a vessel (such as a storage vessel) such that during said discharging a portion of said fluid is directed via a semipermeable barrier into a filtrate chamber and is then directed via a selective barrier into a reactor chamber, wherein said discharging is due to the force exerted by a diaphragm pump connected to the retentate chamber at a position distal to the fluid connector; and
2) Reversing the direction of the force exerted by the diaphragm pump so that at least some fluid from the vessel flows back into the retentate chamber and at least some fluid from the retentate chamber flows into the filtrate chamber (and preferably some fluid from the filtrate chamber flows into the reactor chamber); and
3) Repeating steps (1) and (2) at least once, wherein fluid discharged from the retentate chamber is selected from the group consisting of a suspension and a solution, and wherein the retentate chamber, filtrate chamber, reactor chamber, and diaphragm pump are part of the same enclosed filtration system (preferably wherein the enclosed filtration system is described in the general aspect or second aspect herein above).

In the foregoing and following process, the fact that fluid crosses a portion of a barrier in one direction does not preclude, and indeed is often associated with, fluid flow in the opposite direction at another portion of the barrier.

Normally, material from the retentate, reactor chamber and/or the filtrate chamber will be harvested at least once.

In a variation of the enclosed filtration system process, applicable to a system that comprises a filtrate reservoir, the process comprises the steps of:
1) discharging fluid from a retentate chamber via a fluid connector into a vessel such that, during said discharging, a portion of said fluid is directed via a selectively permeable barrier from the retentate chamber into a filtrate chamber, such that a portion of said fluid directed into the filtrate chamber is directed via an opening in the filtrate chamber wall to a filtrate reservoir and such that a portion of said fluid directed into the filtrate chamber is directed via a selective barrier into a reactor chamber, wherein said discharging is due to the force exerted by a diaphragm pump connected to the retentate chamber at a position distal to the fluid connector; and
2) Reversing the direction of the force exerted by the diaphragm pump so that at least some fluid from the vessel flows back into the retentate chamber, at least some fluid from the retentate chamber flows into the filtrate chamber, at least some fluid from the filtrate chamber flows into the filtrate reservoir and at least some fluid from the filtrate chamber flows into the reactor chamber; and
3) Repeating steps (1) and (2) at least once, wherein fluid discharged from the retentate chamber is selected from the group consisting of a suspension and solution, and wherein the retentate chamber, filtrate chamber, reactor chambers and diaphragm pump are part of the same filtrate reservoir system, (preferably wherein the filtrate reservoir system is described herein above).

Normally, material from the retentate, filtrate reservoir and the reactor chamber will be harvested at least once.

FIGS. 1a-1h illustrate various views of the enclosed filtration system and devices connected to it. (A reference number (e.g., 45 for the retentate chamber) used in one of those views is applicable to the same component in all other of those views.)

In FIG. 1a, an enclosed fluid filtration system 1 is connected via a fluid connector 3 to a process vessel 2, containing the fluid material or retentate 9 to be processed. (In FIGS. 1a, 1b and 1h, the number 9 indicates the location of retentate, not the retentate itself (except for the retentate fluid shown in vessel 2), in the event that system is in use and contains retentate). The fluid filtration system 1 contains at least three chambers: a retentate chamber 45 (shown in greater detail in FIG. 1b-1h) confining the unfiltered material, a filtrate chamber 10 (shown in greater detail in FIGS. 1b-1h) within the filter element 5 (for example, a hollow fiber filter) and a reactor chamber 11 separated from the filter element by a selectively permeable barrier 19 (for example, a hollow fiber cartridge's outer wall or another membrane).

The fluid filtration system 1 is enclosed by housing 15, whose shape, size or orientation may be varied as needed to enclose the system. The housing 15 may be constructed from a variety of materials, including solid polymers, such as polycarbonate or polysulfone, flexible or elastic materials or any other material or composite of materials. The process vessel 2 may be any suitable container for a fluid to be processed. For example, it may be a bioreactor, a circulatory system or any other vessel, nonexclusively including tanks, bags, flasks and the like which can contain liquids. The process vessel 2 may be composed of any suitable material or combination of materials, including, synthetic polymers, inert metals, such as stainless steel, glass, etc; nor shall they exclude rigid, flexible or elastic materials or a combination thereof; nor should such materials be limited in shape, size or configuration, as long as they result in a process vessel. The process vessel 2 is not limited as to accessibility: It may be modified to allow additions to or subtractions from the content of the vessel. Lines or tubes 36 and 39, for example, can be used to effect additions to or subtractions from the content of process vessel 2, for example using a pump 14 to control such addition or subtractions. Such process vessels are commercially available in all sizes and configurations, and are well known to those in the field. The fluid connector 3 serves to direct a fluid from the process vessel 2 via fluid exchange port 35 to the entrance end 42 of filter element 5 which also corresponds to the entrance end of the retentate chamber 45. Entrance 42 while serving as an entrance to chamber 45, may also serve as a reservoir for retentate; its shape and positioning may be varied according to need; its volume may be approximately equal to the diaphragm pump displacement volume, facilitating between reservoir 42 and pump, and further facilitating greater level of retentate concentration and recovery of final concentrate. (FIG. 1b; The construction of the hollow fiber filter is best understood by also taking into account FIGS. 1b through 1h.) The port 35 is held in place by entrance end adapter 40 which may also serve as the end cover for entrance end reservoir 42, which in turn serves as the cover and entrance end to filter element 5; in combination, 35, 40 and 42 serve as a conduit adapter through top plate 16 of housing 15 for directing fluid to the filter element entrance end 42. As a reservoir, reservoir 42 it may be placed above, through or below top plate 15 and its positioning and configuration would not interfere with ports from the filtrate chamber(s) or reactor chamber(s). The fluid flow is further directed through the filter channels 17, which would correspond to the interiors of the lumen(s) of a hollow fiber filter should filter element 5 correspond to a hollow fiber filter. The filter channels collectively correspond to the retentate chamber 45 of the fluid filtration system 1. In one direction, the fluid flow proceeds to, and exits from, the exit end 43 of the filter element 5 Adapter 41 at the exit end 43 of both the filter element 5 and the retentate chamber 45 directs the fluid from the filter element exit end 43 to the liquid receiving chamber 7 of a diaphragm pump 4. Adapter 41 is not limited by its shown configuration or shape; it may be connected to pump 4 directly or through a pump adapter 29; or it may connect the filter exit end 43 to pump 4 through a conduit (not shown here).

The flow through the filter element 5 between process vessel 2 and diaphragm pump 4 (an alternating flow pump) is generated by pump 4 as previously described in U.S. Pat. No. 6,544,424. Pump 4 preferably comprises a pump housing 4 separated into a first interior chamber 8, also referred to as "the first chamber" or a "drive chamber", and a second interior chamber 7, also referred to as the "second chamber" or "the liquid receiving chamber", by an internal diaphragm 6. The pump housing 4 in FIGS. 1a and 1b is made of two housing components, the first pump housing component 25 and the second pump housing component 24. The components comprise flanges 26 and 27, respectively. Pressure in the first interior chamber 8 drives the diaphragm within diaphragm pump 4 without causing contamination of the fluid content in the second interior chamber 7. Shown in FIG. 1a is an air driven pump. Compressed air is directed by controller 54 to chamber 8 through line (tube) 21, preferably through a sterilizing filter 22 and an air inlet port 23. Increasing the air pressure in chamber 8 relative to process vessel 2 drives a flexible diaphragm 6 into chamber 7, driving liquid in that chamber through the filter element 5 to vessel 2. The reverse flow from process vessel 2 to pump 4 is generated by reducing the pressure in chamber 8 relative to the vessel 2. The cycles are repeated. Alternating flow generated by such a pump has been described in U.S. Pat. No. 6,544,424.

Facilitating the construction of an enclosed filtration system, it may be preferable to fix the flexible diaphragm outer flange 47 (FIG. 1f) to the perimeter of the pump housing 26 and 27 (FIGS. 1b and 1f) with a leak proof connection; typically by using a clamping mechanism to squeeze the diaphragm between the flanges 26 and 27 of the two pump halves, which pump halves comprise chambers 7 and 8. While such connection may be accomplished in a number of ways, an example is shown in FIG. 1b and 1f; as illustrated, peripheral flanges 26 and 27 on the respective diaphragm pump halves contain an "O" ring groove 28, which is designed to accept the counterpart "O" ring segment 44 on the flange portion of diaphragm 6. A preferred embodiment of the peripheral flanges 26 and 27 and "O" ring groove 28 is one that permits bonding the peripheral flanges 26 and 27 together and simultaneously secure the diaphragm "O" ring flange 47 and "O" ring segment 44 between flanges 26 and 27; this may be accomplished, by controlling the spacing between adjacent faces of the flanges 26 and 27, as follows: From the outer perimeter of the diaphragm 6 inwards, towards the center axis of the diaphragm pump 4, the diaphragm pump flanges 26 and 27 are spaced from each other by a distance somewhat less than the corresponding thickness of diaphragm 6 flange segments 47 (i.e. the flange segments of the diaphragm), including its "O" ring segment 44 (FIGS. 1b and 1f). That spacing between the flanges minus the thickness of the diaphragm is termed "compression distance". From the outer perimeter of the diaphragm 6, outward, to the outer perimeter of flanges 26 and 27 the spacing between the facing surfaces of flanges 26 and 27 is equal to the compression distance; therefore, when the two facing flanges 26 and 27 are forced together, they compress, by the compression distance, the diaphragm flange segments 47 and the "O" ring segment 44, at the same time forming a contact surface 48 between the two flange segments 26 and 27. Once in contact, peripheral flanges 26 and 27 can be bonded to each other along their contact surface 48; in the process, diaphragm 6 is sealed securely between the pump segments. The method allows for setting the magnitude of the compression on diaphragm 6 flange 47 and "O" ring segment 44 by controlling the compression distance between corresponding and adjacent pump flange segments. Further, to assure that the flanges of the two diaphragm pump halves remain bonded securely along bonding surface 48, the bond can be further reinforced along the surface 49 of flanges 26 and 27. This is exemplified in FIG. 1*f* by securely bonding flange 26 and 27 ends against the inner wall of the housing 15, forming a bond along surface 49, preferably in a leak proof manner. The procedure results not only in securing the diaphragm within the pump and in securing the pump to a confining scaffold, but also in other unique benefits. One such benefit involves using a cylindrical housing 15 that extends the length of the fluid filtration system 1 to form an enclosure for the entire system, including all its vital components. The cylindrical housing 15 may serve as a stand for the entire system, to maintain the system either in the upright position (as shown) or upside down position The bonding or securing of the peripheral flanges 26 and 27 to the housing 15 adds structural support to the entire system to protects its content. Another benefit is the formation of a "base" 25, FIG. 1*b*, to the reactor chamber 11. In addition, by providing the enclosure 15 with a top 16, its possible to fully enclose the filter element 5 and the reactor chamber 11. Enclosure 15 and top 16 may be configured to a desired form and designed to accept various elements, accessories or insertions to make additions and or subtractions to chamber 11, to monitor or affect conditions within; all of which, as will be shown, increase the system's versatility. FIG. 1*a* shows an example of an enclosure 11 formed by wall 15, base 25 and top 16; shown also is a system containing a filter element 5 connected at one end to the pump 4 and at the other end to adapter 40, which forms a passageway to conduit 3 and through enclosure top 16. With top 16 and pump flanges 26 and 27 bonded or sealed against enclosure 15, the filter element 5 is positioned within the reactor chamber 11, where the filtrate chamber 10 (and the filter element 5) share a common selective barrier 19 with reactor chamber 11 as part of their respective walls. (Filtrate chamber 10 is defined by the surfaces of the lumens 17, by the cartridge outer wall 19, and by the areas filled with the potting material 44). By controlling the properties of selective barrier 19 a highly useful selective barrier can be formed between reactor chamber 11 and filtrate compartment 10 (and thereby with filter element 5). As will be shown, using the well known function of the filter element 5 and its capacity for selective separation of constituents between the filtrate chamber 10 and the retentate chamber 45, and further providing a selective barrier 19 between filter element 5 and reactor chamber 11 results in a unique device with multiple useful functions.

The harvest from reactor chamber 11 is collected via line 13 which is connected to harvest port 12, which allows fluid exchange between the chamber and that line so as to allow fluid to enter or leave the reactor chamber. (See also FIG. 1*b* for the relationship of harvest port 12 (or its equivalent) through top 16 (or its equivalent).)

The housing 15, diaphragm pump 4, diaphragm 6, valves, filters and other constituents of the system may be constructed from various materials, preferably from materials that withstand the pressures generated during operation of the fluid filtration system 1, preferably, from materials that may be sterilized either chemically, with steam or radiation; for example, such materials may including stainless steel. However, one of the primary disadvantages of stainless steel is the inability to view the content inside housing 15 or inside the diaphragm pump 4. Some other disadvantages of stainless steel is weight, cost, and difficulty to form into specific shapes. It is therefore preferable, particularly when a disposable system is required, to use materials such as, polycarbonate, polysulfone or others, that are selected for their structural strength and transparency; such materials, that can be readily molded into desired shapes, that are light and relatively inexpensive, that can also be sterilized chemically, with radiation or with steam. An additional desired features of a construction material is its suitability to manufacturing techniques, its amenability to its packaging, storage, transportability, and to providing protection against damage or contamination.

Figure 1H:
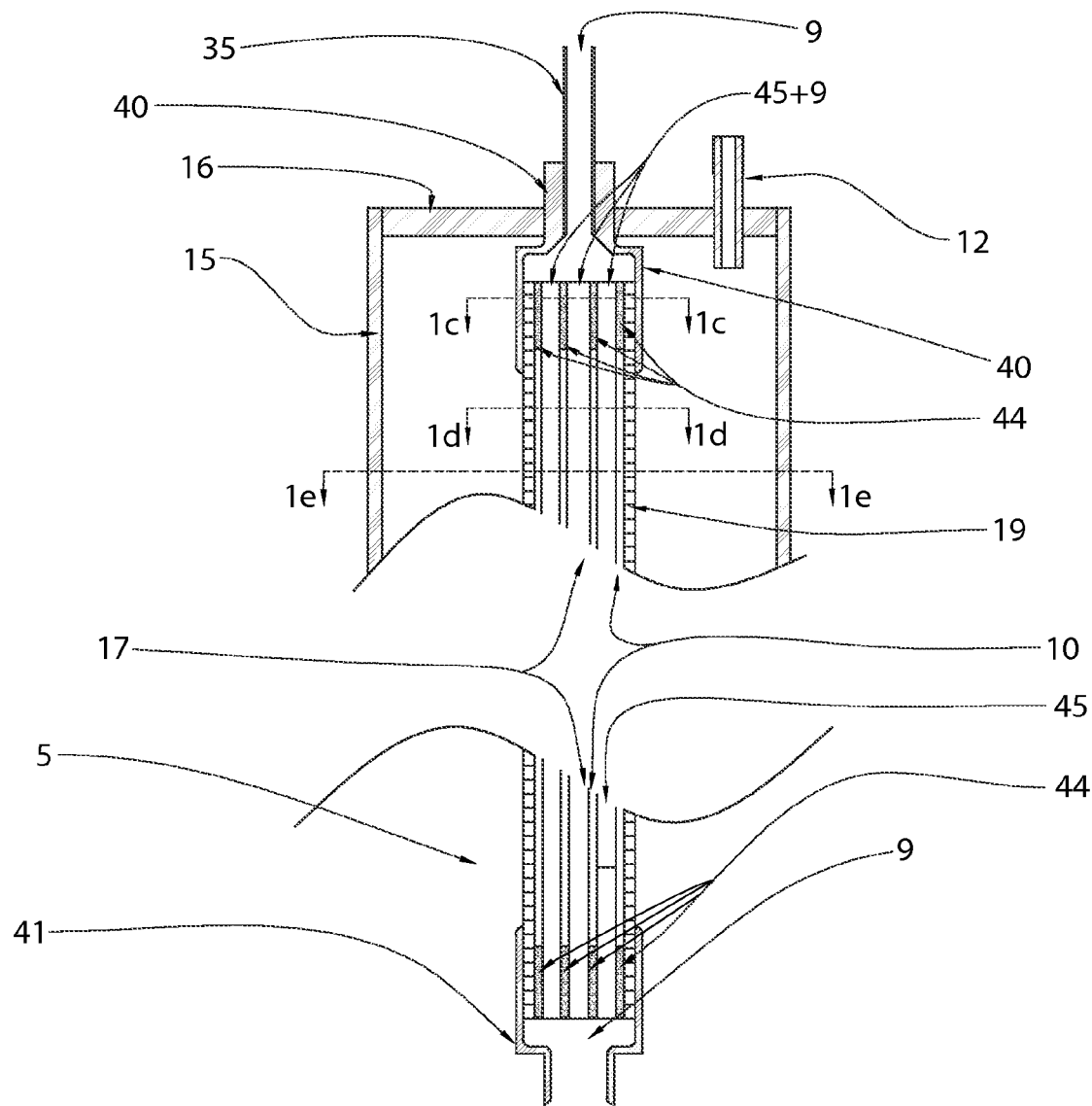

FIGS. 1*a*-1*h* illustrate a hollow fiber filter 5 useful for the present inventions. (The structural features visible in FIG. 1*h* are more easily seen than the same features as shown in FIG. 1*b*.) The filter 5 is a made as a cartridge that comprises multiple hollow fibers (HF) that run, in parallel, the length of the cartridge, from a cartridge entrance end to a cartridge exit end. A segment of the hollow fibers are externally potted at both ends of the cartridge, by methods common to manufacturers of hollow fiber cartridges; the hollow fibers are enclosed by the wall of the cartridge and the potting material 44 at the ends of the cartridge. Examples of potting compounds are epoxies and polyurethanes. As a result, there is a chamber bounded by the cartridge wall 19 potted ends 44 and the walls 17 of the HF. That chamber can be used as the filtrate chamber for the present inventions. One could say that there are multiple retentate chambers, each corresponding to a single HF intraluminar space. However, for purposes of description, the intraluminar spaces are considered collectively to constitute a retentate chamber in each of the present systems.

The walls 17 of the lumens (hollow fibers) of the illustrated hollow fiber filter are selectively-permeable, conveniently providing the selectively permeable wall referred to in the descriptions of the systems. The outer wall 19 of the filter cartridge (the cartridge wall) comprises a selective barrier referred to in the descriptions of the systems, that barrier also being selectively permeable.

Figure 2:
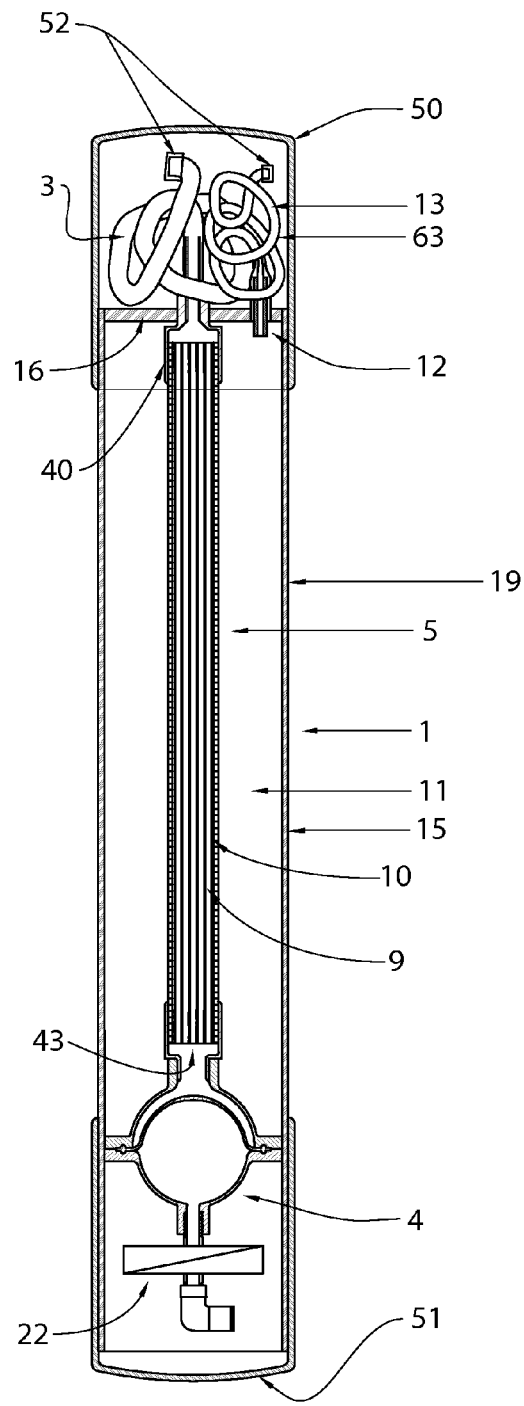
FIG. 2 shows a sectional view of an embodiment of the enclosed filtration system of the invention.

FIG. 2 also illustrates the enclosed filtration system 1 of FIGS. 1*a* through 1*h* but shows it augmented with coverings 50 and 51. In FIG. 2, the enclosed filtration system 1 is connected to both a connector line 3 (i.e., a fluid connector line) and, via harvest port(s) 12 to harvest line(s) 13. Furthermore the system is enclosed by coverings 50 and 51 at each end, so that its otherwise exposed ends are fully enclosed. The fluid connector line and harvest line(s) are shown as folded because in this particular example they need to be folded so that they can be enclosed by the coverings. Fluid connector line 3 and harvest line(s) 13 are each protected with a shield 52 at their end.

Reference numbers 4, 5 and 15 in FIG. 2 apply to the same components they refer to in FIGS. 1*a* through 1*h*.

Figure 3:
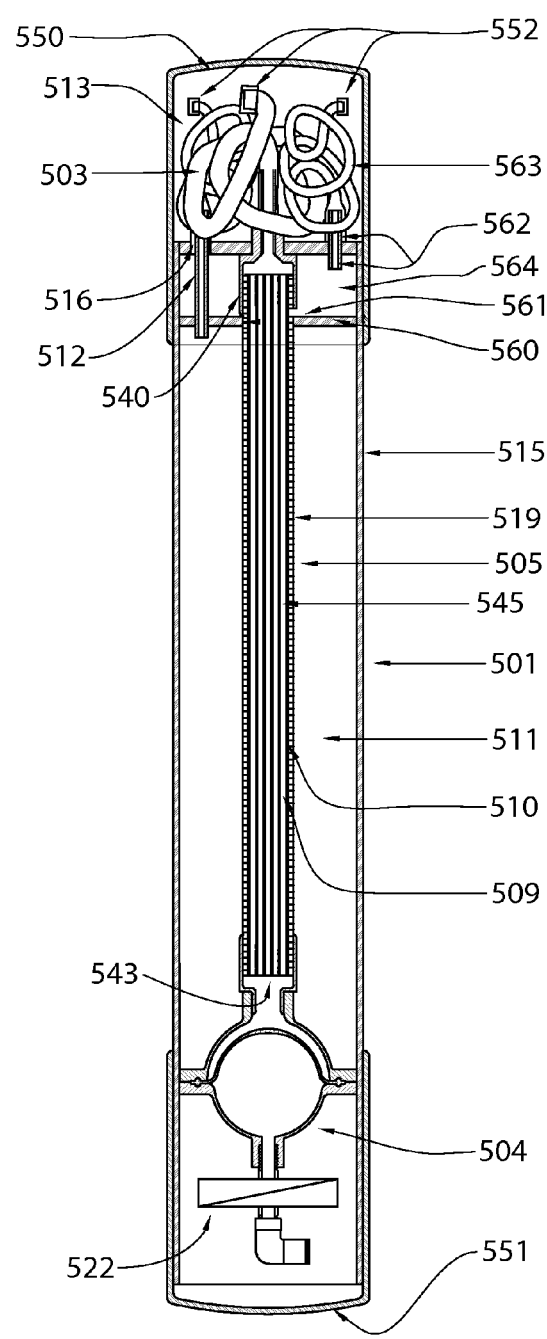
FIG. 3 shows a sectional view of an embodiment of the enclosed filtration system of the invention.

FIG. 3 illustrates a variation of the enclosed filtration system 1 shown in FIGS. 1*a*-1*h*. The system 501 shown in FIG. 3 has filtrate reservoir 564 not present in the system FIGS. 1a-1h. In FIG. 3, filtrate reservoir 564 and the reactor chamber 511 are separated from each other by a separating barrier 560 that does not permit direct fluid exchange between the reservoir 564 and the chamber 511. Both the filtrate reservoir 564 and the reactor chamber 511 can undergo fluid exchange separately with the filtrate chamber 510 of the filter element 505. Fluid exchange between the filtrate chamber 510 and the reactor chamber 511 is effected through a portion of the filter element 505, which has an outer wall similar in structure to the outer wall of the filter element 515 in FIGS. 1a-1h; i.e., it is a selective barrier.

In contrast, fluid exchange between the filtrate chamber 510 and the filtrate reservoir 564 is effected through an opening 561 which provides a direct conduit from the filtrate chamber 510 to reservoir 564, where filtrate can be harvested via harvest port 562 ("the second harvest port") and line 563. The harvest from reactor chamber 511 is collected via line 513, which can access reactor chamber through tube 512 that extends into that chamber; functioning as a port ("the first harvest port").

In the system 501 in FIG. 3, the housing 515 is similar to the housing 15 in FIGS. 1a and 1b.

In FIG. 3, critical connections, including the fluid connector segment 503, harvest tubes 512, 562, pump 504, filter element 505, and other system accessories, in their various forms, are shown enclosed and fully protected by coverings 550 and 551. Such coverings may also enclose other lines or devices connected to the system or to its various compartments. These may include tubings, sensors, electric lines, filters etc.; such devices may be further enclosed or protected by secondary shields; for example, fluid connector segment 503 and harvest tubes 563, may be further protected with shield 552 at their end; therefore, when covering 550 is removed and fluid connector segment 503 and harvest lines 563 are exposed, their internal volume remains protected against contamination while remaining available for their connection to their counterparts in a sterile manner.

It can be seen however, that many other components and features of the enclosed filtration system 1 as described in FIGS. 1a-1h are present in system 501 in FIG. 3. For example, all components of the filter element 5 are essentially paralleled by the filter element 505 in FIG. 3. Also the diaphragm pumps 4 and 504, and the interconnection between the filter element and the pump, are not only present in FIGS. 1a and 1b but as well as in FIG. 3. Such common components further include but are not limited to the retentate chamber 45 and 545 and the selectively permeable barrier 19 and 519). Furthermore fluid exchange port 35 of FIGS. 1a-1h is present is present in FIG. 3.

The enclosed fluid filtration system and filtrate reservoir system shown in FIGS. 2 and 3 may each be encapsulated in a protective bag for additional protection against contamination or mishandling; the entire system may be sterilized at once. Such safety features are essential in foreseen applications such as dialysis as well as other medical and cell culture related applications. In FIGS. 1a-1h and, as applicable, FIGS. 2 and 3, the primary function of the fluid connector 3 is to provide a reliable, sterile, low sheer fluid conduit. Preferably, it should allow the flow to be bidirectional between process vessel and fluid filtration system 1; furthermore, when using the system as a disposable unit, it becomes essential that a reliable and simple connection is formed between such a disposable unit and the process vessel. A preferred feature of the fluid connector 503 is the ability to form, break, or reform the connection between the fluid filtration system 1 and the process vessel 2 in a sterile and reliable manner. There are a number of well known techniques for joining or breaking a fluid connector in a sterile manner, including the use of tube welders, SIPable valve assemblies, joining or uncoupling sterilized couplings within a biological safety hood, use of sterile connectors such as the clean-pack (by Pall corp.) or the DAC™ (by GE), or for that matter any other device which permits a sterile connection or disconnection between tube segments; such connections, however, do not exclude using fluid connectors that may include more than one fluid connector, where one or more connector serve to deliver fluid to the enclosed filtration system and one or more connectors serve to deliver fluid from the enclosed filtration system; such connector(s) may include assorted types of valves, couplings, or devices which affect the flow through the conduit, including check valves, sensors, restrictors, etc. The fluid connector may also be partitioned to access more than one port on the process vessel or multiple vessels or multiple enclosed reactor systems, as the need arises. The fluid connector may also incorporate probes, such as flow meters, for monitoring flow rates through the connector, probes, the likes of pH, dissolved oxygen, etc., for monitoring the vitality of the culture flowing through the fluid connector. The rapid flow between vessel and enclosed reactor system reflects the conditions in the enclosed reactor system and process vessel. Any combination of the above or similar modifications to the fluid connector may be used by those with knowledge in the field.

For the enclosed filtration system and the filtrate reservoir system, a connector line will normally be connected, via a retentate chamber entrance end adapter to the entrance end of the retentate chamber. In an embodiment of the enclosed filtration system, referred to as the modified adapter embodiment, the system further comprises:

1) A reservoir adapter as its retentate chamber entrance end adapter, such that said reservoir adapter, in addition to being connected to a first connector line also comprises a second connector line;
2) a drainage tube connected at one of its two ends to the entrance chamber of the alternating flow pump, said drainage tube extending to a point exterior to the enclosed filtration system so that retentate in the entrance chamber of the pump can be collected outside the system.

Figure 1I:
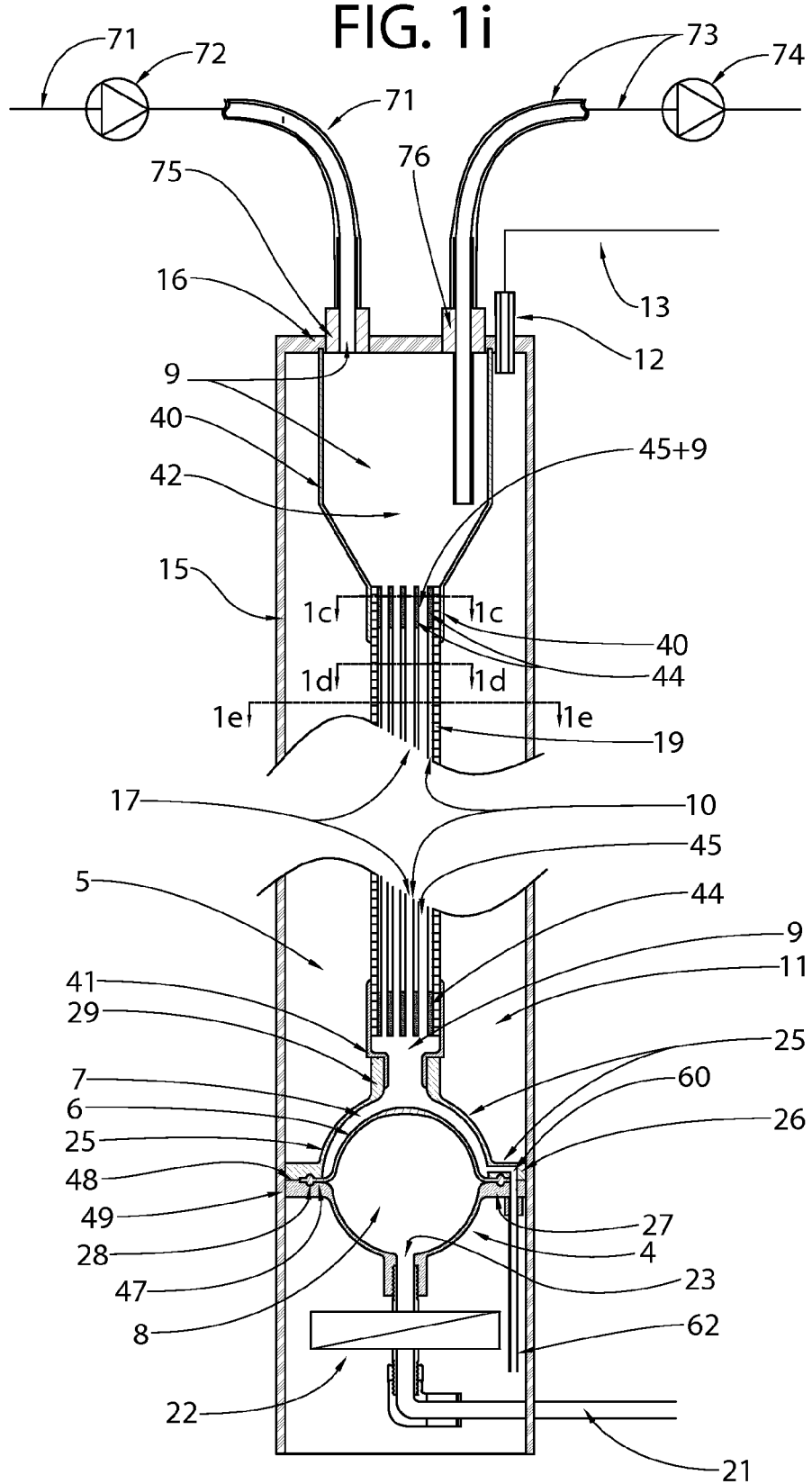
FIG. 1i shows a sectional view of an embodiment of the enclosed filtration system of the invention wherein an adapter is connected to a second connector line and wherein there is a conduit for fluid recovery from a pump chamber.

An example of the modified adapter embodiment of the enclosed filtration system is illustrated in FIG. 1i. It can be seen that the FIG. 1i can be considered a modified version of the enclosed filtration system illustrated in FIGS. 1a-1h.

Here the system comprises a reservoir adapter 42. In addition to connector line 71 that is connected to the reservoir adapter, there is a second connector line 73 connected to the reservoir adapter. Connector line 71 can be connected to an outside source of fluid such as a vessel but is particular suited for being connected via a catheter to a person's blood s stream, in which case the connector line will also be connected to the blood stream. The blood will enter the filtration system via line 71 and exit via line 73. In that mode, the system is suited for blood and kidney dialysis.

In the dialysis mode, an advantage of the system is that the benefits of an alternating tangential flow filtration system are utilized but the blood stream in the patient is always in the same direction.

When line 71 is connected to a vessel outside the system (such as vessel 2 in FIG. 1a), the modified adapter embodiment is also well suited to recovering small volumes from the vessel if such small volumes occur because of continued filtration.

In the modified adapter embodiment, one may add a pressure sensor to the reservoir adapter.

It can be seen from FIG. 1*i* that the embodiment also comprises a drainage tube 60, 62, which can be considered to have two sections, 60 and 62, respectively. The drainage tube is available for recovery of retentate, especially the final retentate volume, and generally for sampling the retentate. It is also available for diluting the retentate.

The volume of the reservoir adapter is preferably equal or slightly larger that the displacement volume of the diaphragm pump 4, but it can be any size.

Pumps 72 and 74 allow control of fluid addition to the reservoir adapter and the rate of removal of modified (concentrated) fluid from the reservoir adapter. The two pumps may be used as valves in a manner that allows pressurization of reservoir adapter 42. The system can thus be pressurized (requiring no vacuum for operation), which is useful for many filtration applications.

A diaphragm pump ("the reservoir pump") may be used in place of the reservoir adapter, in which case the system will comprise two such pumps. The reservoir pump would have two connector lines connected to one of its chambers. The other chamber would be connected to the filter element. The diaphragms of the two pumps would have to move in synchrony.

The features of the enclosed filtration systems facilitate their range of applications, storage and transportability. As shown in FIGS. 2 and 3, for example, the entire system may be packaged in a self-contained container. The pump(s), filter, fluid connector, harvest line, modifier module, modifier suspension solution can all be conveniently provided preassembled, enclosed and sterile.

An important attribute of the invention is the closed nature of the enclosed filtration system (as it is for the enclosed bioreactor systems described below). The enclosed nature of the system also allows filtration applications with hazardous materials (i.e., corrosive, flammable, bio hazardous, etc.), provided the appropriate filters and all other components of made of materials that are compatible with the process. This may include the use of filters made from metals, ceramics or other material. Similarly, the diaphragm and other components of the system may be made from any number of materials that will allow compatibility with the requirement of the process. As was described, all components can be connected in such a manner as to totally confine the process.

Enclosed Bioreactor System and Process

The enclosed bioreactor system, in a preferred aspect, comprises the following:

1) a hollow fiber filter element (preferably a cylindrical hollow fiber filter cartridge) said filter element comprising an entrance end and an exit end, said filter element further comprising a plurality (more than one) of filtration retentate chambers, each filtration retentate chamber being an open-ended hollow fiber, said fibers disposed in parallel to the center axis of the filter element (the center axis extends through the center of the cylinder from one filter element end to the other), wherein the fibers each have an entrance at the entrance end of the filter element and an exit at the exit end of the filter element, and wherein each fiber comprises a semi-permeable outer wall, said filter element further comprising a filtrate chamber that encloses said fibers but does not block their open ends, such that the semi-permeable outer walls of the fibers are also part of a filtrate chamber wall;

2) a filtrate harvest tube (preferably rigid), said tube penetrating the filter element and its filtrate chamber via the filter element entrance end, said tube, preferably, disposed along the center axis of the filter element;

an alternating flow diaphragm pump, said pump connected to the exit end of the filter element so as to permit fluid from the pump to enter the filtration retentate chambers, said pump comprising a pump housing, two chambers, and a diaphragm separating the chambers, 4) a processing chamber, said chamber enclosing the cartridge, said chamber comprising a base, an outer wall (preferably cylindrical), a base, and a top plate, wherein the base is attached to both the outer wall and the pump housing in a sealed manner and wherein said top plate is attached to the outer wall in a sealed manner, and wherein the top plate is penetrated by the harvest tube so that fluid can flow from the filtrate chamber to outside the reservoir chamber;

5) A processing chamber harvest line or lines and a processing chamber addition line or lines, said harvest and addition lines penetrating either the top plate (preferred), outer wall, or base of the processing chamber so that fluid can be harvested or removed from the processing chamber or added to it;

6) A port in either the top plate (preferred), outer wall, or base of the processing chamber through which oxygen can be fed into the processing chamber, said port comprising a sterilizing filter to prevent contamination of the processing chamber by microorganisms; and 7) Port(s) in either the top plate (preferred), outer wall, or base of the processing chamber through which sensing devices can be inserted into the processing chamber.

Preferably the foregoing preferred aspect of the enclosed bioreactor system comprises a tubular fluid connector inside the processing chamber and, preferably but not exclusively, disposed around the filter element such that said connector is not in direct contact with said filter element, said connector comprising a sealed exit end or sealed end and an entrance end, said sealed end disposed between the top plate of the processing chamber and the entrance end of the filter element, said sealed end penetrated by the harvest tube, said sealed end for deflecting fluid flowing from the filter element entrance so that such fluid flows through a separation space separating the fluid connector and the filter element, said fluid connector comprising an open end through which the deflected fluid can escape into the processing chamber;

It is preferred that the enclosed bioreactor system comprise a plurality of sparger holes in its base, which holes function as part of the ports through which the oxygen is fed into the processing chamber It is also preferred that the enclosed bioreactor system comprise additional ports, in either the outer wall, top plate, or base of the reservoir chamber so that fluid (or fluid containing suspended cells), can be added to the processing chamber It is also preferred that enclosed bioreactor system comprise an agitation device; exemplified by an open-ended draft tube (open at both ends; preferably cylindrical) inside the reservoir chamber and surrounding all or a part of the fluid connector tube, said draft tube not directly touching the fluid connector tube, said draft tube held in position by a support frame also connected to the outer wall of the reservoir chamber.

The exit of the pump is preferably protected by a filter that prevents microorganisms from entering the pump.

In a particular embodiment, the sealed end of the fluid connector tube is modified so that it comprises a puppet valve the permits part of the fluid to move in one direction directly from the processing chamber into the space between the valve and the entrance end of the filter element. However, the puppet valve does not permit fluid to flow in the opposite direction, deflecting fluid flowing from the filter element entrance so that such fluid flows through a space separating the tube and the filter element, directing the fluid exiting from the entrance end of the filter element to the processing chamber.

An enclosed bioreactor system comprising, in a general aspect, the following:

1) a filter element, said filter element comprising an entrance at an entrance end and an exit at an exit end, said filter element further comprising a plurality of filtration retentate chambers (such as a plurality of hollow fibers) wherein the filtration retentate chambers each comprise an entrance at the entrance end of the filter element and an exit at the exit end of the filter element, each of said filtration retentate chambers further comprising an outer wall, each said outer wall comprising a semi-permeable portion, said filter element further comprising a filtrate chamber that encloses the semi-permeable portions of the filtration retentate chamber outer walls but does not block the exits or entrances of the filtration retentate chambers, such that the semi-permeable portion of the outer walls of the filtration retentate chambers is also part of a filtrate chamber wall;
2) a filtrate harvest tube, said tube penetrating the filter element and filtrate chamber so as to permit fluid to leave the filtrate chamber;
3) an alternating flow pump, said pump connected to the exit end of the filter element so as to permit fluid from the pump to enter the filtration retentate chamber, said pump comprising a pump housing, two chambers, and a diaphragm separating the chambers,
4) a processing chamber, said chamber enclosing the filter element, said chamber comprising an outer wall, said outer wall attached to the pump housing in a sealed manner, wherein said outer wall is penetrated by the harvest tube so that fluid can flow from the filtrate chamber to outside the reservoir chamber;
5) A processing chamber harvest and addition line(s), said harvest and addition line(s) penetrating the wall of the reservoir chamber so that fluid can be, respectively, harvested or removed from the processing chamber or added to the processing chamber;
6) A port in either the wall of the reservoir chamber through which oxygen can be fed into the reservoir chamber, said port comprising a sterilizing filter to prevent contamination of the reservoir chamber by microorganisms; and
7) Port (s) in either the top plate (preferred), outer wall, or base of the processing chamber through which sensing devices can be inserted into the processing chamber.

Preferably the general aspect of the system is modified so that it further comprises a tubular fluid connector in the processing chamber and disposed, preferably, around the filter element such that said connector is not in direct contact with said filter element, said connector comprising a sealed end and an entrance end, said sealed end disposed between the wall of the process chamber and the entrance filter element, said fluid connector penetrated by the harvest tube, said sealed end for deflecting fluid flowing from the filter element entrance so that such fluid flows, preferably, through a space separating the fluid connector and the filter element, said fluid connector comprising an open end through which the deflected fluid can escape into the reservoir chamber.

It is preferred that the general aspect of the system be modified to comprise a single or plurality of holes in its wall, through which the oxygen is fed into the processing chamber.

It is also preferred that the general aspect of the system be modified to comprise additional ports, in the wall of the processing chamber so that fluid (or fluid containing suspended cells), can be added to the reservoir chamber.

It is also preferred that general aspect of the system be modified to comprise an an agitation device; exemplified by an open-ended draft tube (open at both ends) inside the processing chamber and surrounding all or a part of the fluid connector tube, said draft tube not directly touching the fluid connector tube.

In both the preferred and general aspects of the enclosed bioreactor invention, the line extending from the pump to an external controller preferably comprises a sterilizing filter that prevents microorganisms from entering the pump. Furthermore, in both aspects, the sealed end of the fluid connector tube is modified so that it comprises a poppet valve the permits fluid to move in one direction, directly from the processing chamber into the space between the valve and the entrance end of the filter element. However, the poppet valve does not permit fluid to flow in the opposite direction, deflecting fluid flowing from the filter element entrance so that such fluid flows through a space separating the tube and the filter element.

In both the preferred and general aspects of the enclosed bioreactor invention, in one preferred embodiment, the system further comprising a rigid harvest tube positioned along the center axis of the filter element, said tube extending from inside the filtrate chamber, through the top of the bioreactor, to outside the bioreactor.

In the enclosed bioreactor system, the processing chamber can be used as a bioreactor. As a bioreactor it can be used for culturing assorted cell types. The filter element (filtrate chamber plus retentate chamber) will function as a cell separation device for removal of spent medium and replacing removed medium with fresh medium. The enclosed bioreactor system may be used as a disposable perfusion bioreactor. Such a system can greatly simplify the process of continuous culture. It can eliminate the often complex setup involved in the set up of cell separation system with a bioreactor. It can reduce the effort involved in maintaining cell lines in continuous culture, as needed in research, development and production.

It is desirable that enclosed reactor systems of the invention be sterilizable and that, subsequent to sterilization, it can be stored sufficiently sealed to prevent subsequent contamination of its interior by external microorganisms that otherwise would enter into the interior of the system subsequent to its sterilization. It is also desirable that these systems are in a configuration and made with construction materials that render the system disposable.

The enclosed bioreactor system process, in a general aspect, comprises circulating fluid back and forth between a processing chamber and a plurality of filtration retentate chambers enclosed within that processing chamber, wherein fluid is driven in alternating directions by via a pump connected to the filtration retentate chambers, wherein motion of the fluid through the filtration retentate chambers results in transfer of fluid between the filtration retentate chambers and a filtrate chamber that is separated from the filtration retentate chambers by semi-permeable membranes, said filtrate chamber enclosed by said processing chamber.

Normally, material from the filtrate chamber will be harvested at least once during the processing of culture.

The processes is preferably carried out using an enclosed bioreactor system described herein.

FIGS. 4a-4e show that the many essential features of the enclosed filtration systems shown in FIGS. 1a-1h are retained. In the case of FIGS. 4a-4e, however, the processing chamber 211 can be used as a cell culture bioreactor containing a culture of animal cells or other microorganisms, where such content serves as retentate 209. As in FIGS. 1a-1h, a filter element, 205 is present. processing chamber size, makeup and configuration may be varied according to need. The processing chamber 211 serves the same function here as the process vessel 2, shown in FIG. 1a does. Another similarity with the system in FIGS. 1a-1h is: Fluid connector 203 provides a conduit between filter element 205 and the processing chamber 211 just as the fluid connector 3 provides a conduit between the reactor chamber 11 and process vessel 2. The fluid connector 203 directs the flow from the entrance end 242 of filter element 205 into the reservoir chamber 211. The fluid connector comprises a fluid connector entrance and a fluid connector exit. The fluid connector 203 may be further configured in a manner that directs the fluid discharging into chamber 211 to maximize mixing within in the chamber, and to increase oxygen transfer into the culture inside the chamber, while minimizing shear. Fluid connector 203 defines a separation space 284 that permits fluid flow, as shown in one form in FIGS. 4a and 4b, between filter element 205 wall 219 and fluid connector 203. Further, pump 204 at the base 243 (and 225) of the processing chamber 211 is connected to exit end 241 of the filter element 205, similar to how filter element 5 is connected to pump 4 in FIG. 1a. (Components 6, 7, 8, 23, 27, and 29 of the pump, pump adapter, and pump housing, pump air inlet port in FIG. 1 are similar to components 206, 207, 208, 223, 227, and 229 respectively in FIGS. 4a-4e. Other features shown include, but are not limited to the sterilizing filter 222 and the line (tube) 221. Another similarity is the fluid receiving end of fluid connector tube 203 positioned above the filter entrance end 242. A primary dissimilarity between the system shown in FIGS. 1a-1h and that in FIGS. 4a-4e is the extension of the fluid connector tube 203 from entrance end 242. Where in FIG. 1a, the fluid connector extends to an external vessel 2, in FIGS. 4a-4e the fluid connector 203 extends into an internal vessel, reservoir chamber, 211. It extends, preferably, though not exclusively, symmetrically about the filter element 205, down towards the base 243 of the filter element 205 and terminates in the processing chamber above its base 225.

Figure 4C:
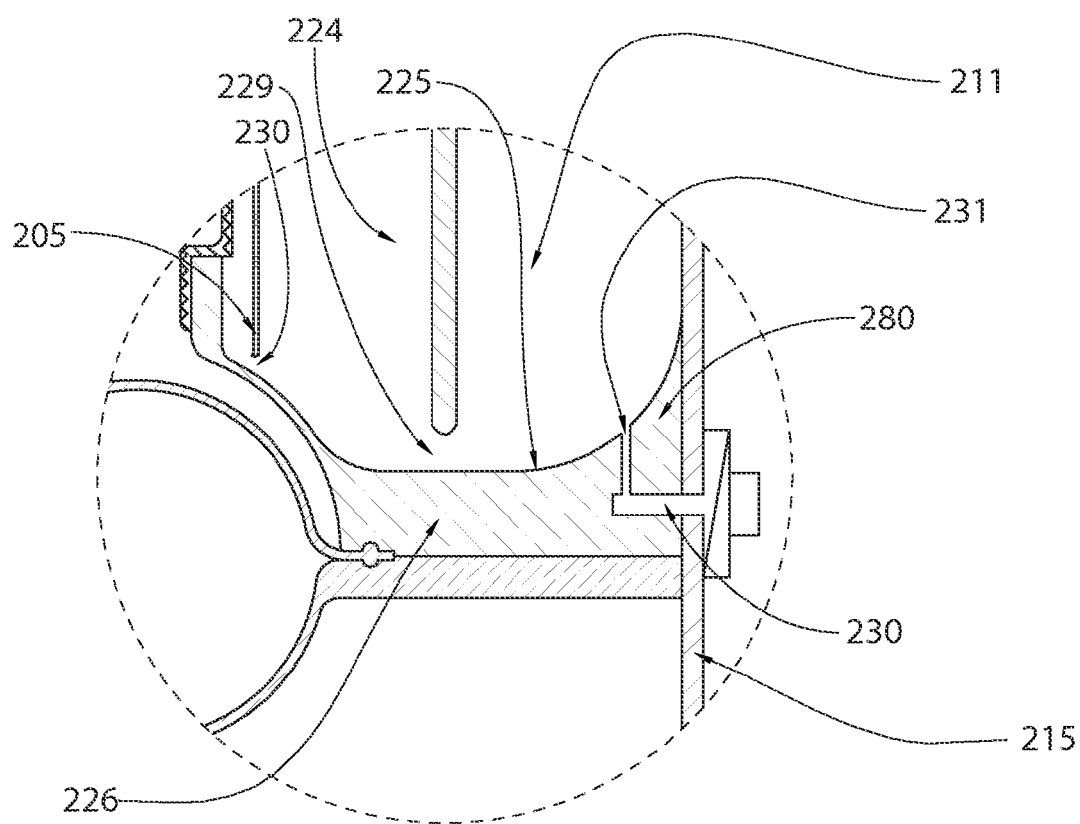

Therefore, during the pump 204 pressure cycle, fluid flows from pump chamber 207, through the hollow fiber lumens that function as filtering retentate chambers, (FIGS. 4a, 4b, and 4c; See also 45, 17 in FIGS. 1a-1h). The fluid then exits at the filter element entrance end 242 via entrances 270 at the entrance ends 271 of those retentate chambers (FIG. 4d). The fluid is then directed into the fluid connector 203 followed by discharge into the processing chamber at the other end of the fluid connector through opening 230 (See FIG. 4a). The fluid connector end disposed between the filter element entrance end 242 and the top plate 216 is sealed in FIG. 4a. Therefore, the fluid emerging from the filter element entrance cannot escape through that end of the fluid connector but rather is deflected towards opening 230.

During the exhaust cycle of the diaphragm pump, the direction of fluid flow reverses, flowing from processing chamber 211 through opening 230, into the fluid connector 203, through entrance end 242 into the hollow fibers, out of the fibers via their exits 272 at their exit ends 273, and back into pump chamber 207 (See FIG. 1h for the location of the exit and exit ends of the fibers). In addition to providing tangential flow for the filtration process, the alternating flow will also provide mixing in the processing chamber 211 due to the velocity of fluid discharging into the reactor chamber 211. FIG. 4a In addition to the mixing generated by the reversible flow of fluid between pump 204 and processing chamber, further agitation may be required; an example of which, is shown in FIGS. 4a and 4b; shown is the presence of a tubular open-ended draft tube within the processing chamber, to facilitate mixing within the reactor chamber, the draft tube being disposed around the fluid connector 203 but distanced from the fluid connector. The draft tube 224 comprises an open draft tube entrance and an open draft tube exit. The air or oxygen bubbled into the processing chamber through openings 231, that are positioned symmetrically on the external perimeter of the draft tube, provide fluid uplift energy, producing circular flow about both ends of the draft tube; a process well understood in the field and described further later in the text.

In FIG. 1a, the barrier 19 is preferably a selective barrier to regulate exchange between filtrate chamber 10 and reactor chamber 11. In the system in FIG. 4a, however, while one may use a selective barrier 219, typically, barrier 219 will be a non-permeable barrier in order to prevent the mixing between the adjacent chambers 210 and 211.

Although it is understood that the filtrate chamber 210 may be accessed in a variety of ways or filtered material removed from the system by various means, FIGS. 4a, 4d and 4e show an example of filtrate harvest line 213 connected to the preferably rigid filtrate harvest tube 214, the line and tube providing a route for removing filtrate (e.g., cell free filtrate) from the filtrate chamber 210. Medium removed from the culture as filtrate is replaced with fresh medium for example, via addition line 281 connected to one of the available ports (also referred to as "conduits") connected to the processing chamber. Harvest pump 249 controls the rate of filtrate removal. A processing harvest line 244 extends from outside the system into processing chamber 211. Line 244 optionally can be connected to a manifold of the kind described below or to another line.

Figure 5A:
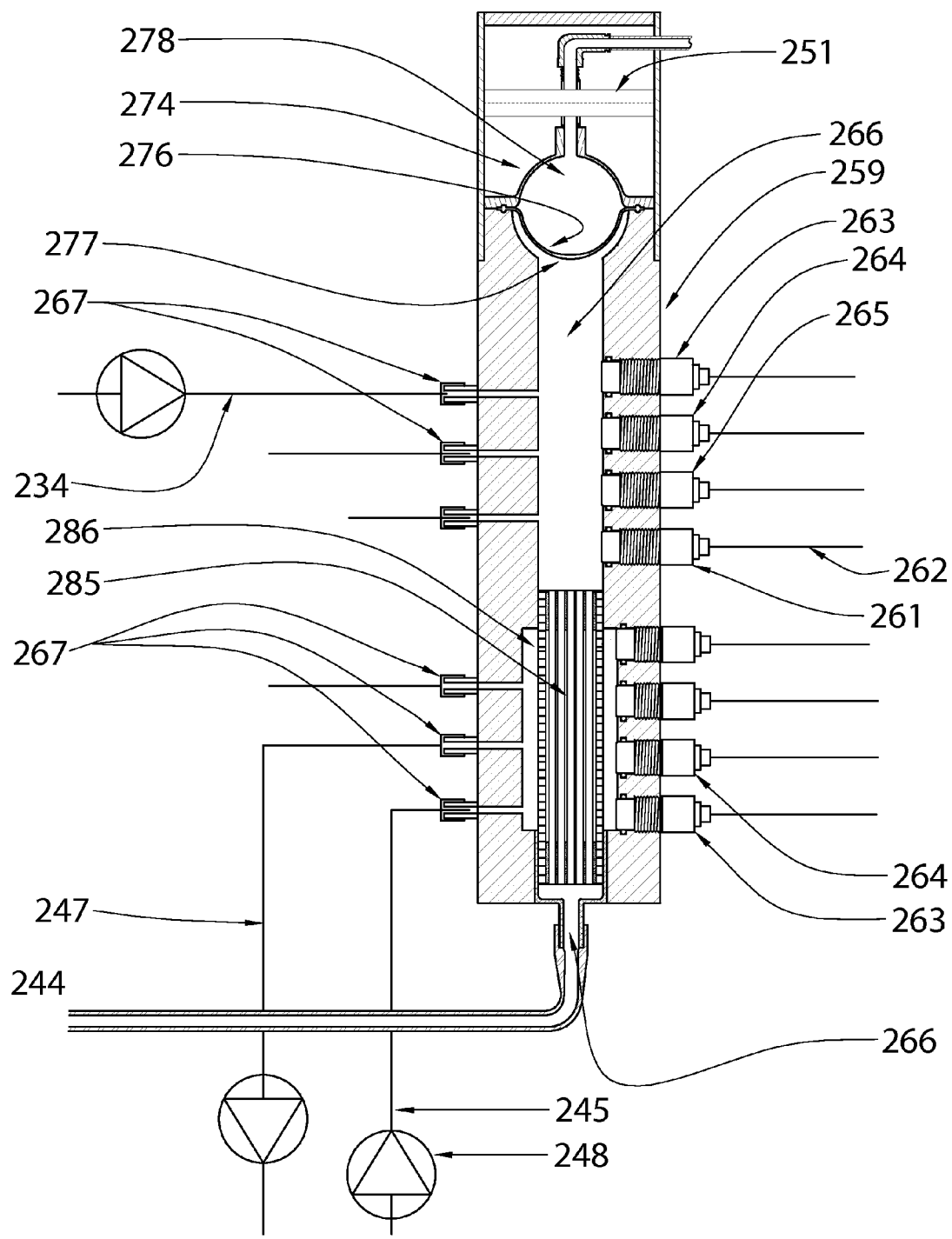
FIG. 5a shows an embodiment of the manifold sampling system invention in partial cross section.

A pump connected to a harvest line 244 may be used to "bleed" the culture, a procedure commonly used to control cell concentration. Control of fluid addition or removal to and from the system, may be manual or automated using common pumping systems, procedures and controls. Multiple ports and conduits can be inserted in the wall or top plate of the processing chamber, or be part of a manifold (ports 245, 246, and 247 in FIG. 5a) connected to lines such as 244. Others may be used for addition of media, supplements, base, gases or other additives. Other ports may be used as a vent(s) 238 or for sampling 234 (FIG. 4a; also manifold in FIG. 5a). It may be beneficial to place the harvest tube 214 into the center of the filtrate chamber 210, i.e., along the center axis of the filter element 205 (FIGS. 4a, 4d and 4e). Such placement facilitates construction and assembly of the entire system by minimizing the number of walls that the harvest tube needs to penetrate through in the enclosed bioreactor system. It also eliminates or minimizes obstructions onto which cells may attach and accumulate, as could occur by placement of a harvest tube perpendicular to the flow path in the fluid connector 203 and processing chamber 211. Filtrate harvest tube 214, especially when rigid, may also be used as point of attachment for fluid connector 203 at the point where the tube penetrates through the fluid connector. It may also serve for placement of flow control devices for controlling flow through the fluid connector or other parts of the system, as will be demonstrated.

A system, such as in FIGS. 4a-4e that has to sustain cells at high concentration and viability must also accommodate culture with its essential requirements, few examples, of which, are provided, since those familiar with cell culture or similar applications know what the essential requirements are:

Oxygen—an adequate oxygen level is a critical component required for sustaining a culture at high cell concentrations. An example of an oxygenation system, is shown in FIGS. 4a, 4b and 4c. Shown is a sparger ring 230 discharging gasses into the processing chamber 211 through pores 231. The sparger ring may be placed symmetrically in the base 225 of the reservoir chamber 211 or within pump flange 226. Channel 232, which may effectively extends from the pores to the outer wall 215 of the processing chamber is supplied with gasses through channel 232 which traverses the processing chamber wall 215 and contains a filter 233 at its inlet to sterilize the inflowing gas. Such a circular tubular sparger ring 230 and sparge pores 231 may be preformed into the pump flange 226 during its production.

It can be seen that the pores 231 are disposed at the end of the processing chamber proximal to the diaphragm pump.

Sparger pores 231 may be positioned along the base 225 to maximize oxygen transfer, reduce shear and increase agitation. Sparge pores 231 or other parts of the air inlet assembly may be equipped with one way check valves to assure flow is only in one direction, stopping back flow into the sparger ring 230. Another method (not shown) for delivering oxygen into the culture may involve forming a channel in the draft tube support frame 252 for delivery of gasses into the draft tube 224 itself. Such draft tube may itself be configured in a manner that oxygen entering the draft tube may be delivered into the culture by a sparge mechanism or by a diffusion mechanism by methods familiar to those in the field.

Agitation—Mixing of the culture, also a critical aspect of a suspension culture, may be provided by a number of known mechanisms; one example, shown in FIGS. 4a-4b, where draft tube 224, is placed centrally surrounding the filter element 205. In combination with the sparger pores 231, the updraft created by the rising bubbles generate an uplift of fluid flow within the draft tube. A fluid updraft may be created by bubbles on the outside of the draft tube 224 and a fluid return in downdraft through the center of the draft tube exiting opening 229, between the base of the draft tube and the reactor base 225, to resume the circular flow. Note that diaphragm pump flange 226 and the reactor base 225 may be shaped to minimize formation of dead zones for cell accumulation and to facilitate circular flow of the culture. The top end of the draft tube is maintained below liquid level 237 when there is liquid in the reservoir. This "air-lift" method of agitation is a well understood process and may be varied by those familiar with the process. Attachment and positioning of the draft tube may be accomplished in various ways. As shown in FIG. 4a, it may be secured to the reactor wall 215 through draft tube support frame 252, or to the top plate 216, or base 225 by other attachments. A vent tube 238 at the top of the reactor will provide a vent for the added gas or for gas flow in general.

Another possible form of agitation involves taking advantage of the alternating flow caused by the diaphragm pump. As shown in FIGS. 4d and 4e, It is possible to incorporate a one directional check valve assembly 225 into the fluid connector 203, which may direct flow through the fluid connector and flow direction in the processing chamber 211. As illustrated in FIGS. 4a and 4d: During the exhaust cycle of the pump 204, overall flow is from the processing chamber 211 to the pump chamber 207. At least part of the flow is directed through poppet valve opening 246 and part of the flow will proceed through opening 230, as previously described. Poppet valve 228 (See FIGS. 4d and 4e) which may be a flexible material, will be forced away from opening 246 by the negative pressure generated within the fluid connector relative to the reactor chamber and the resulting force generated by the flow of fluid flowing from the processing chamber 211 through port 246, into the filter element 205 on its way to pump chamber 207, (See FIG. 4a.) During the pump pressure cycle, on the other hand, when flow direction reverses, the flow emerging from pump chamber 207 flows into the filter element 205, emerging at the entrance end 242 and forcing puppet valve 228 against opening 246, effectively blocking further fluid flow through those openings; thereby, flow can only proceed through the fluid connector 203, emerging from opening 230. (See FIG. 4a.) The process offers circular flow within the processing chamber 211 to facilitate mixing. Orientation of the valve 225 or its configuration may be varied according to need. Other common forms of agitation may be used to facilitate mixing within the processing chamber.

Temperature control for the system may be accomplished in a variety of ways including using a thermal blanket, water or air jacket a heating element, etc.

The enclosed bioreactor system described can be customized for various uses and to achieve optimal results.

Figure 4F:
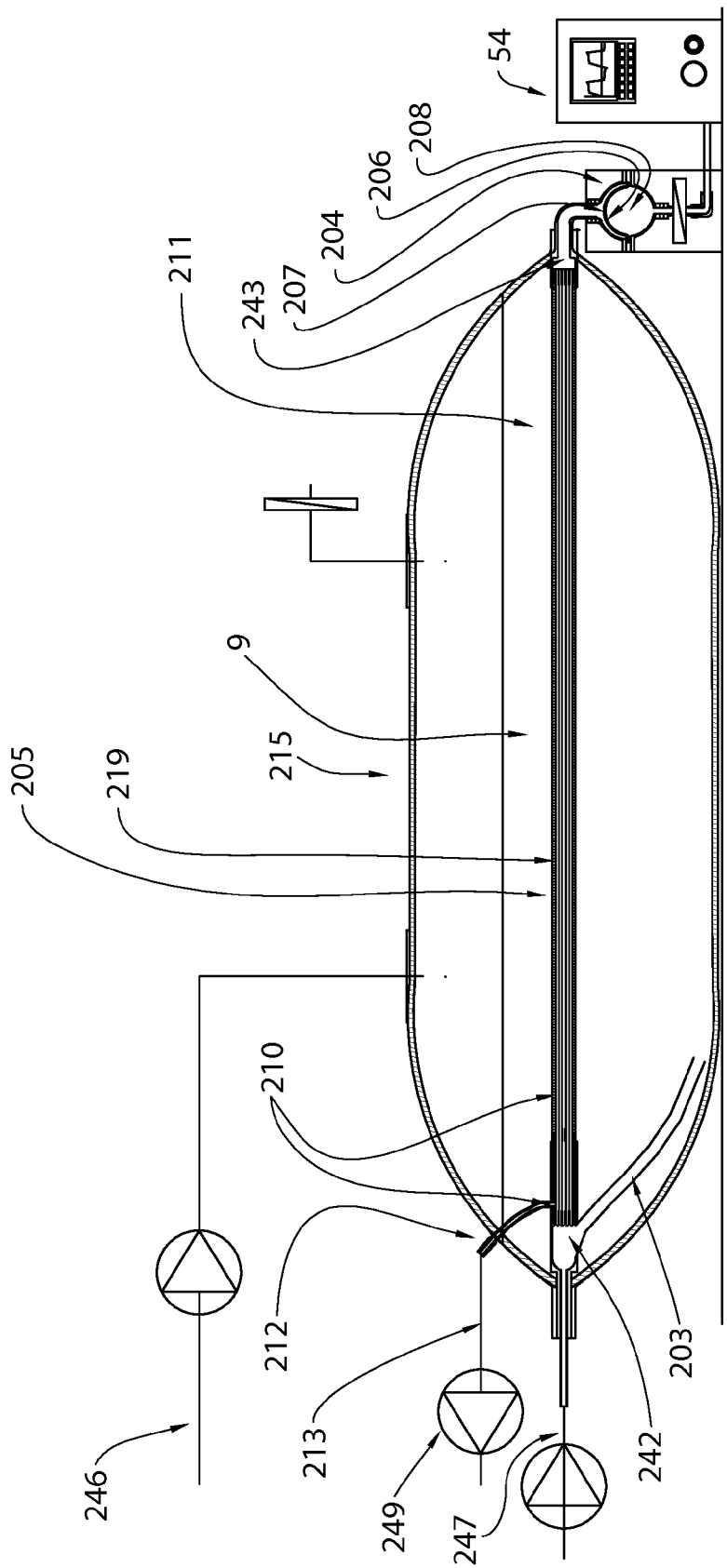
FIG. 4f shows a partial sectional view of an enclosed bioreactor system of the invention in which the reservoir chamber is horizontally disposed.

Another example of the enclosed bioreactor system is shown in FIG. 4f. The example in FIG. 4f shows an enclosed bioreactor system where the processing chamber 211 is inside a bag 215 and which also serves as an enclosure for the entire system, analogous to the system in FIG. 4a. The filter element 205 placement, however, is horizontal in this example. Also the draft tube 224, and the air sparging pores 231 present in FIG. 4 are absent here, other forms of agitation and oxygen delivery to the culture are provided. The pump 204 is connected to the filter element at one end, the exit end 243; at its other end or entrance end 242, the filter element is connected to the fluid connector 203 or the entrance end may discharge directly into the bag. As previously described, fluid flow generated by the diaphragm pump flows reversibly between pump chamber 207 and processing chamber 211 through the filter element 205. Filtered harvest may be collected from filtrate chamber 210 using port 212 and harvest line 213 and pump 204; further additions or subtractions from the system may be accomplished through other lines 246, 247, or others if necessary. Additionally, in FIG. 4f, components 54, 206, 208, and 219, are essentially the same or functionally the same as components 54, 206, 208, and 219 in FIGS. 4a, 4b, 4d and 4e. It is evident that there are other components in FIG. 4f that, although not numbered, have the same meaning as FIGS. 4a, 4b, 4c and/or 4d.

Accordingly, the fluid filtration system in FIG. 4f can be considered to be a simplified version of the fluid filtration system in FIG. 4a. Absent in FIG. 4f are connector tube 203 encircling the filter element 205, a cylindrical draft tube 224, sparger ring 230 and pores 231 for oxygen bubble entry.

Figure 4G:
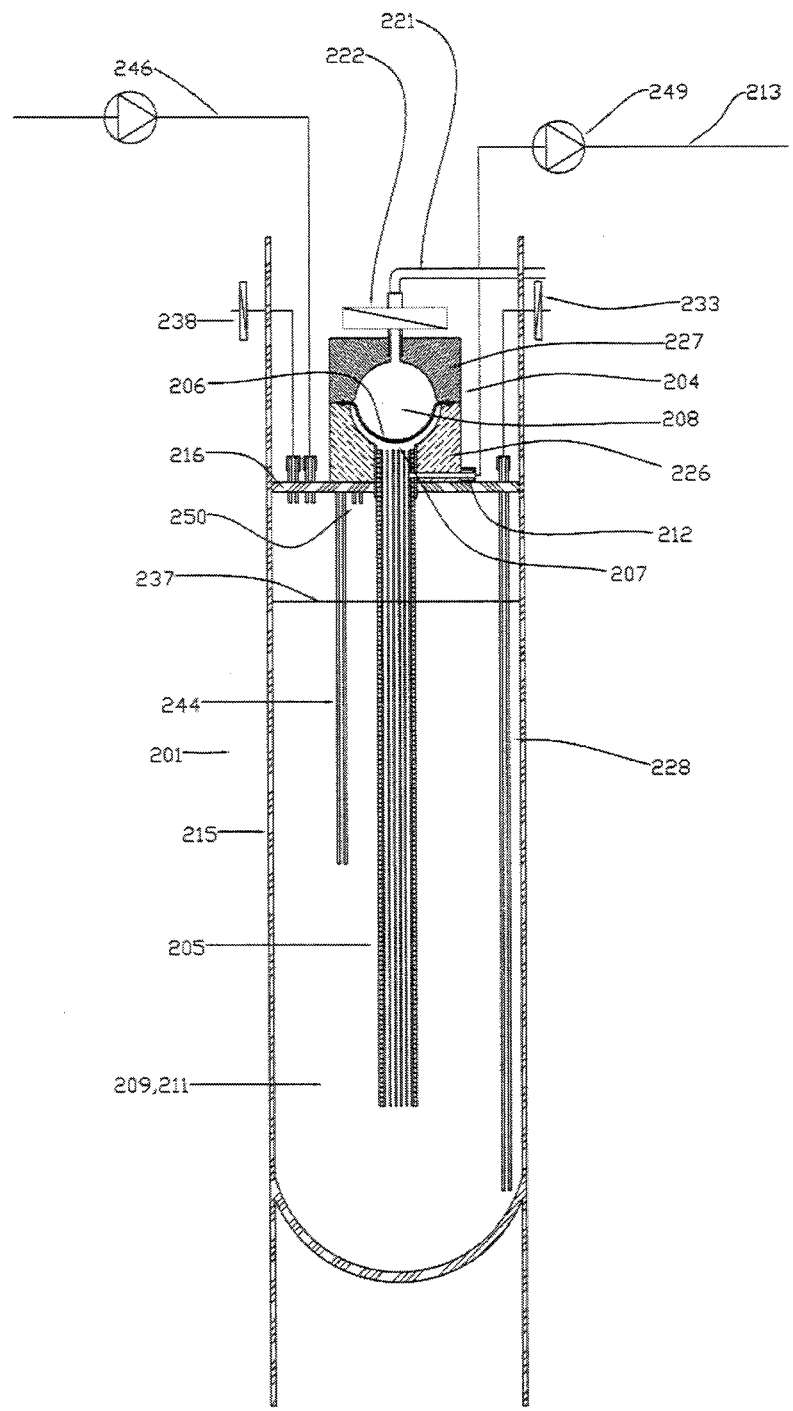
FIG. 4g shows a partial sectional view of an enclosed bioreactor system of the invention in which the pump is in the upper position and the filter element is below the pump.

The examples provided are to demonstrate some, but not all of the possible configurations of the system. One can envision a system where the pump is in the upper position and the filter element is below the pump. Fluid ejected from the diaphragm pump flows into the top of filter element and ejected into the reactor camber at the lower end of the filter. Such an embodiment is illustrated in FIG. 4g. (Note that in FIG. 4g, post 250 and the port for line 244 are only visible below the top plate 216. Those ports extend above top plate 216 but the portions of those ports above the top plate are not visible in FIG. 4g because cylindrical component 226, which comprises part of the pump flange, obscures them from view for purposes of that Figure.

One can further envision a system where the diaphragm pump is not connected to the filter element directly but through a conduit. Other examples are also possible.

Sampling Manifold and Process

The manifold invention in a general aspect comprises;
(1) a channel (such as the internal channel of a tube), the channel comprising a first end and a second end;
(2) an alternating flow diaphragm pump connected to the first end of said channel and tube, and
(3) a plurality (more than one) of probe ports located on the channel at a positions between the two ends of the channel; wherein the second end of the channel is connectable to a fluid source (such as a vessel or reactor chamber).

Ports provide places where a probe or sensor may be inserted for purposes of sampling or monitoring the fluid in the channel. Ports also provide places where, additions or subtractions to the content in the channel can be made. When used for sampling, each probe port is connected to a probe device. Each probe device will be a device that measures a physical or chemical property of fluid within the channel. The measurements can include, but are not limited to, measurement of pressure, pH, or the concentration of a particular material present in the fluid.

The manifold invention may further comprise a filter element within its channel and a filtrate chamber disposed between the filter element and one or more ports. The filter element will be, for example, a hollow fiber filter cartridge. The outer wall of the filter cartridge is preferably fully permeable so that the size selection step for smaller substances is controlled by the semi-permeable membrane walls of the hollow fibers.

The manifold sampling process of the invention comprises:
(1) causing fluid from a container (or chamber or compartment) to enter a manifold channel;
(2) and then causing the fluid to mostly or entirely exit said channel so as to return to the container, wherein the motion of the fluid controlled by an alternating flow diaphragm pump, and
(3) measuring a property of said fluid while it is in said channel, said measurement accomplished by probe device connected to said channel, said probe device capable of measuring a physical or chemical property of said fluid.

The process is preferably done using a manifold system described above.

Rapid fluid equilibration between the filtrate and retentate compartments (or chambers) in an alternating tangential flow process as described herein can facilitate such measurements such that one may sample the retentate and filtrate in the same sample stream.

Figure 5B:
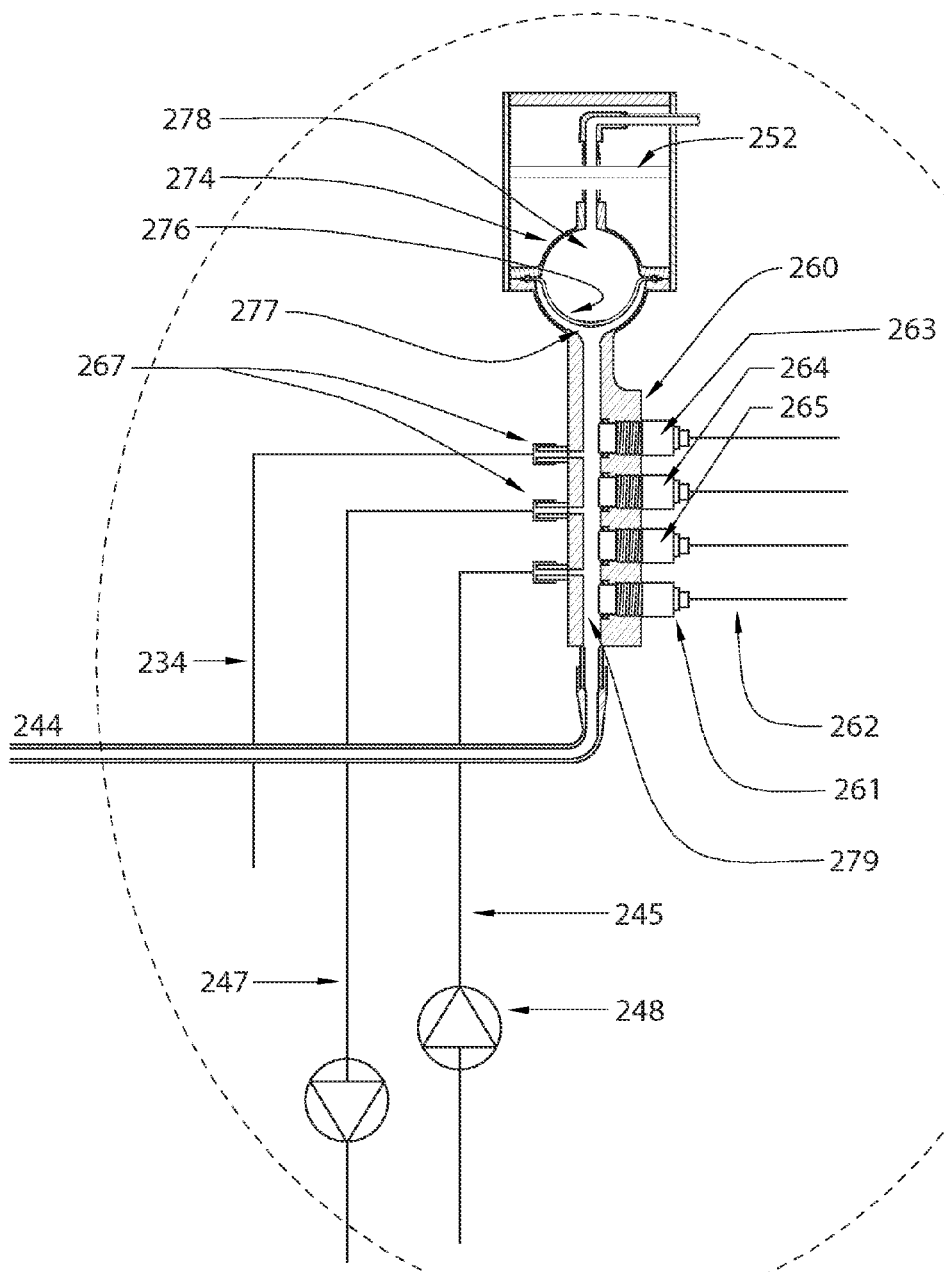
FIG. 5b shows an embodiment of the manifold sampling system invention in partial cross-section.
Figure 7:
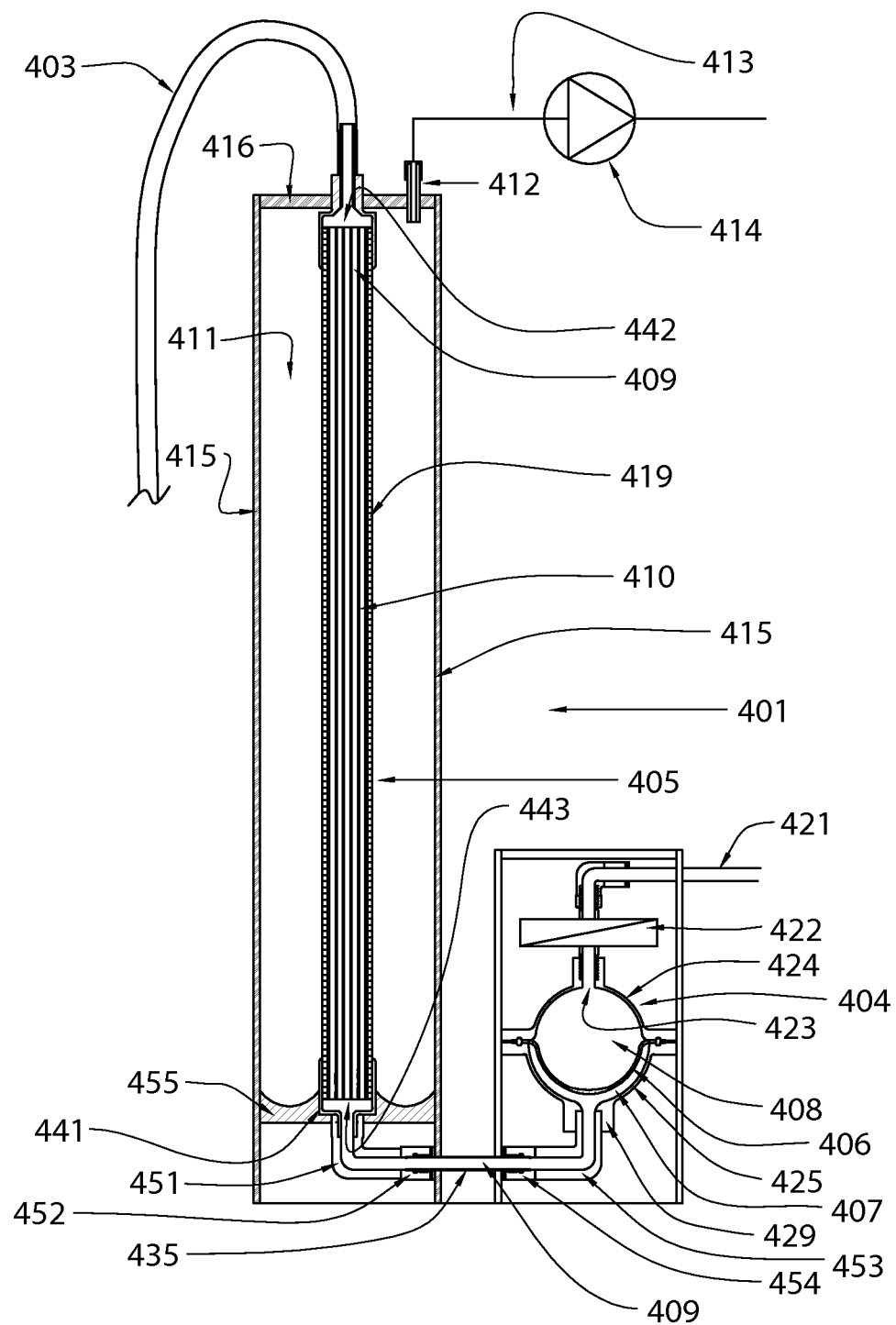
FIG. 7 shows a sectional view of the enclosed filtration system in which the diaphragm pump is separately enclosed.

FIGS. 5a and 5b illustrate two embodiments of the sampling manifold, 259 and 260. The connection 244 from the manifold to a process vessel facilitates severing the manifold from the bioreactor or its connection to the bioreactor; and facilitating the performance of such procedures in a sterile manner. The disposable nature of a bioreactor system (e.g., FIGS. 4a and 4f) is enhanced by the use of a removable sampling manifold, which via line 244 in FIG. 4a could, for example be reversibly connected to a bioreactor While it is possible to insert probes directly into processing chamber 211 (FIG. 4a), it would not be convenient to do so. Individual probes can be expensive; and if supplied with the bioreactor, greatly add to the cost of the system. Direct insertion of probes into a presterilized bioreactor risks contamination; such probes can fail in mid run or drift out of calibration rendering them useless and therefore jeopardizing the culture. Probes can be large, not easily accommodated by a small culture system, as may be necessary. It would be beneficial therefore to incorporate a device such as the present manifold invention capable of a single sterile connection, frequently sampling the culture and monitoring the status of the culture by analyzing the samples. Such sampling would have to be sufficiently rapid to monitor rapid changes in the culture. The manifolds 259 and 260 shown in FIGS. 5a and 5b, are capable of holding multiple and varied probes such as 261, 263, 264, and 265. The outputs from the probes may be connected, for example via a line 262, to a controller device or devices (not shown) capable of monitoring such outputs and provide data output and control capability of culture parameters such as pH, DO, $CO_2$, and others.

Manifolds 259 and 260 both contain a channel (e.g., a tube), 266 and 279 respectively, which at one end (a first end) is connected to the pump 274 and at the other end (a second end) is connectable, for example, to a bioreactor, bioreactor system, or filtration system, through line 244 so as to allow fluid to flow between the manifold and the bioreactor. Channels 266 and 279 are connected to a diaphragm pump 274. Such pump is similar to the diaphragm pumps 4 and 204 and has two chambers, 277 and 278 separated by a diaphragm 276. The pump 274 is capable of receiving and expelling fluid through pump chamber 277 and process chamber 211 (See FIG. 4a), as previously described for pumps 7 and 207. The frequency of fluid cycling between vessel and pump, through the line 244 and probe manifold can be controlled by controlling the cycling frequency of diaphragm pump 274. This provides a convenient method for controlling the culture sampling rate. Probes 261, 263, 264, and 265 can be secured in the manifold 260 with their sensing ends exposed into the manifold channel 266 or 279. Fluid within the manifold channel 266 or 279 can thus be probed and monitored. The probe placement within the manifold must be in a manner to prevent contamination of the fluid within the manifold from an external sources and to confine the fluid within the manifold from escaping. Although less preferable, it is not beyond the scope of the concept being described to use a continuous pump, such as a peristaltic pump, to remove culture media through one conduit, directing the sample through a manifold 260 for analysis, than return the sample to the culture vessel through another conduit.

There are other substantial benefits to the described sampling manifold 260. The following are some examples:

1. The sampling manifold may also incorporate multiple ports, such as 267, for making additions and subtractions to and from the culture in the bioreactor, for example via a line 234, 245 or 247, and for example, pump 248. Thereby, the number of ports that need to be added to the enclosed reactor system can be greatly reduced, facilitating that system's construction and simplifying its use.

2. A single connecting line 244 between sampling manifold 260 and an enclosed reactor system such as 201 shown in FIG. 4a, allows quick attachment or detachment of the sampling manifold to the vessel using a common tube welder or similar sterile connectors. Should a probe fail or require calibration, one sampling manifold can be rapidly exchanged with another, greatly reducing the risk to the culture.

3. Such sampling manifolds may be prepared and sterilized separately from a bioreactor, such as 201 shown in FIG. 4a, greatly adding to the convenience of their use, and sterilization.

4. The sampling manifold may be readily used with disposable bags. One of the limitations of disposable bags is the difficulty in placing multiple probes into the bag and in monitoring and control of culture conditions within the bag. The probe manifold such as described can alleviate this handicap.

5. The described manifold may be modified in a manner, as shown in FIG. 5a that includes a filter element 285 (such as a hollow fiber filter cartridge) in channel 266. When the filter element 285 is used, it is preferred to use a manifold filtrate chamber (or compartment) 286 surrounding the filter element and in fluid contact with the ports 263, 264, and 267. The position of the filter element 285 in FIG. 5a is a one position; however, the filter element and filtrate chamber 286 can be similarly positioned elsewhere inside channel 266. Culture media will flow reversibly between chamber 211, containing the culture, and pump chamber 277.

6. The ability to remove culture samples from the bioreactor offers the user with additional diagnostic capabilities not readily possible with fixed probes within the bioreactor; for example, the flow of a sample, flowing from the bioreactor to the pump can be stopped for a certain duration, during which the decay rate of oxygen concentration can be monitored, reflecting the condition of the culture; similarly, the rate of change in other culture parameters, glucose, $CO_2$, pH, and others, may be repeatedly monitored without disturbing the culture. Repeated removal of samples from the bioreactor is not required, thereby reducing the risk of contamination and change in the sample.

7. The ability to form a filtered stream by filter element 285 allows directing of the stream by a filtrate line 247 to a secondary analytical device such as a HPLC or some other analyzer.

The filter element 285 can be held in position within channel 266 by two O-rings 258. However, the filter can also be positioned and sealed within channel 266 using adhesives or mechanically.

A manifold filtrate chamber 286 formed between the filter and the wall of channel 266 may be probed by the probes exposed to channel 266. Preferably the filter element 285 has a fully permeable outer wall. The alternating flow between chamber 211 and 277 facilitates flux of fluids between the retentate and filtrate compartments in manifold 260. (The retentate compartment of the manifold is, for example, the spaces inside the hollow fibers of the filter element 285 plus the portion of channel 266 not occupied by the filter element).

The alternating flow through the manifold between bioreactor and pump 274 enables the probe manifold to accurately reflect the condition of a culture. One can extend this concept to include monitoring of culture conditions either in the retentate, filtrate, or processing chambers of a system, and in parallel streams if desired. Monitoring the condition of the culture in a filtered stream, free of cell debris, can extend the life of the probe by minimizing accumulation of debris on the probes; the filtered stream may also be directed to other analytical instrumentation that require a filtered sample. This provides the user with the ability to monitor cell growth and culture activity on an ongoing basis. Such a device is illustrated in FIGS. 5a and 5b.

Dual Pump System

The Dual Pump Invention

Another invention is a dual pump system, said system comprising:
1) a first pump, said first pump being a two-chambered diaphragm pump, said first pump comprising a first chamber that is a pump reservoir chamber connectable to a source of fluid, said first pump further comprising a second chamber being an interface chamber connectable to a conduit, said first and second chambers being separated by an elastically deformable diaphragm;
2) a conduit connected to the interface chamber of said first pump; and
3) a second pump, said second pump comprising an interface chamber connected to said conduit, said second pump interface chamber comprising a movable element selected from the group consisting of an elastically deformable diaphragm or a non-elastic, piston-like, movable wall, said second pump being connectable to a pressure controlling mechanism.

In one embodiment, said pressure controlling mechanism is connected to the second pump exclusively (not also to the first pump). In another embodiment, said pressure controlling mechanism is connected to both the first pump and the second pump, for example by using a peristaltic pump.

Examples of the source of fluid include but are not limited to bioreactor chambers, for example, the retentate chamber of the enclosed fluid filtration system or enclosed bioreactor systems described above In one embodiment, the second pump is also an alternating flow diaphragm pump, such that the pump comprises an elastically deformable diaphragm. In another embodiment, the second pump is a mechanical pump, such that the pump comprises a movable wall, whose reversible movement and pumping action are imparted by well established methods. One example of many possible mechanical pumps is one where the movable wall is a piston (a piston wall) that is part of a piston pump driven by a cam mechanism coupled to a motor or a step motor. It is well understood, the reversible piston movement is determined by the cam stroke In another embodiment of a possible mechanical pump, the movable wall comprises coupling, directly or indirectly, to a screw or threaded drive shaft which in turn is coupled to a motor or stepper motor. Rotation of the drive shaft causes, in screw-like fashion, the wall to move. The direction of shaft rotation (and therefore the direction of wall movement), and the distance traveled by the wall, can be controlled by direction and duration of rotation of an electro-mechanical rotary device and/or by configuration of the screw shaft. The rate of piston movement in either of the above two embodiments may be controlled by the rate of motor rotation, by the pitch and pitch direction of the screw; it is also understood that the second pump chamber and wall must be sealed and leak proof in order to transfer all its energy to the first pump.

It is preferred that the interface chamber of the first pump be larger than any other chamber of a pump in the two pump system, thus limiting the travel of the diaphragm within the first diaphragm pump.

Preferably the interface chamber of the first pump, the interface chamber of the second pump, and the conduit connecting them, are preferably filled with a non compressible medium, preferably a liquid.

Optionally, the dual pump system further comprises sensors in one or more chambers, especially the interface chamber of the second diaphragm pump, for added control of pump action. Also, optionally, one or more additional pumps are connected to the two pumps of the dual pump system through air, liquid or mechanical coupling capable of controlling the action of the pump(s) in the multiple pump system.

The dual pump pumping process comprises cycling a first and second pump through one or more pump cycles, the pumps being connected to each other by their respective interface chambers, the first pump being a two-chambered diaphragm pump which, in addition to its interface chamber, comprises a pump reservoir chamber connected to an external source of fluid, wherein the interface chamber of the second pump is exposed to a pressure emanating from an external source of pressure (a pressure controlling mechanism) that is alternately less than or greater than the pressure in the external source of fluid.

Using a single pump system (e.g., rather than a double pump system), driven by air pressure (For example in FIGS. 1a and 4a) has proven quite effective, particularly at large scale. However, it suffers from a number of features that negatively effect its reliability and pumping accuracy. Such shortcomings are derived from the inherent compressibility of air. For example, referring to FIGS. 1a and 1b during the pressure cycle, gas (usually air) flows into the pump's first chamber 8, pressurizing and compressing the gas therein. Having a flexible diaphragm 6 between the pump's air first chamber 8 and its second chamber 7 separates the content in the chambers and permits expansion of first chamber 8 during its pressurization, simultaneously driving the liquid from the second chamber 7 towards process vessel 2. The resulting flow rate is a function of the pressure difference, ΔP, between the first chamber 8 and process vessel 2. For the purpose of description, assuming the pressure in vessel 2 remains constant, the pressure in chamber 8 required to drive diaphragm 6 at a specific rate is term "driving pressure"; therefore, with increasing ΔP, and the resulting increase in driving pressures, hence, flow rates, it becomes more difficult to control diaphragm position. Slight changes in service air pressure, inherent delays in response of sensors, regulators, valves or controller electronics can effect the final position of the diaphragm at the end of the pressure cycle.

Similar difficulties arise during the exhaust cycle. As gas pressure in pump first interior chamber 8 is reduced relative to process vessel 2, flow direction reverses from vessel 2 towards the diaphragm pump 4. The rate of flow will depend on the ΔP between the vessel 2 and diaphragm pump 4, and is termed "negative driving pressure".

However because of the compressibility of gases, generating similar +ΔP or −ΔP during the pressure and exhaust cycle, respectively, does not result in similar flows in both directions. To determine the flow rates to and from chamber 8, one may use the following equation:

Flow rate=chamber 8 displacement volume/displacement time,

It is apparent that by maintaining same flow rates to and from chamber 8, the duration of the respective pressure and exhaust cycle will not be similar; pressurizing chamber 8 relative to vessel 2 compresses the gas within that chamber; thereby, increasing the mass of the gas within the chamber; conversely, transitioning to the exhaust cycle decreases the pressure in chamber 8; effectively requiring longer to clear the gaseous mass from chamber 8. Efforts to establish constant cycle periods during pressurization and exhaust can be achieved but at dissimilar gas flow rates, an undesirable effect.

Another effect of using a gas to drive a single pump alternating tangential flow system is observed during cycle transitions. Transitioning to a pressure cycle, the pressure in first interior chamber 8 needs to switch from full exhaust to pressure driving pressure; similarly, transitioning to the exhaust cycle, the pressure in chamber 8 needs to switch from full pressure to negative driving pressure; such drastic changes in pressure during an alternating flow cycle result in a short delay during cycle transition, and are referred to as a "soft transition. Such a delays becomes severe at higher flow rates, where fluid flow momentum becomes increasingly significant in disrupting the transition. These are some factors that can greatly complicate cycle flow control accuracy. While a soft transition may be beneficial in many applications, it may not be beneficial in many others. It is well known for example that any reduction in tangential flow, (technically reverting to the less efficient "dead end filtration"), during the soft transition can decreases the life of the filter or reduce its filtration capacity. Uninterrupted or undelayed cycle transition may be more desirable, particularly where a more consistent alternating tangential flow is essential; such undelayed cycle transitions are termed "hard transitions", Yet another potential problem of using one diaphragm pump is inherent in the use of a single diaphragm to separate the pump into an air drive chamber and a liquid chamber. Should the diaphragm rupture, pressurized air will flow into the process vessel unrestricted, creating potentially a hazardous condition. Also liquid may flow towards the controller, potentially contaminating the process and damaging the controller.

It is possible to compensate for some of the described shortfalls, of the air driven single pump system, with various control schemes sensors, pneumatic devices, process modifications, or other possible schemes. Nevertheless, it would be more desirable if diaphragm cycle or flow rate could be controlled with greater precision and reliability during the alternating flow cycles. It would also be preferable if the integrity of an enclosed reactor system remain intact and uncontaminated should a diaphragm rupture. In some cases, it would be highly desirable if sources of pumping energy other than compressed air or vacuum are used to drive the pump, particularly in those cases where compressed air or vacuum services are limited or not available. FIGS. 3a, 3b, 3c and 3e provide examples of methods, other than the direct air driven single pump system described.

Figure 3A:
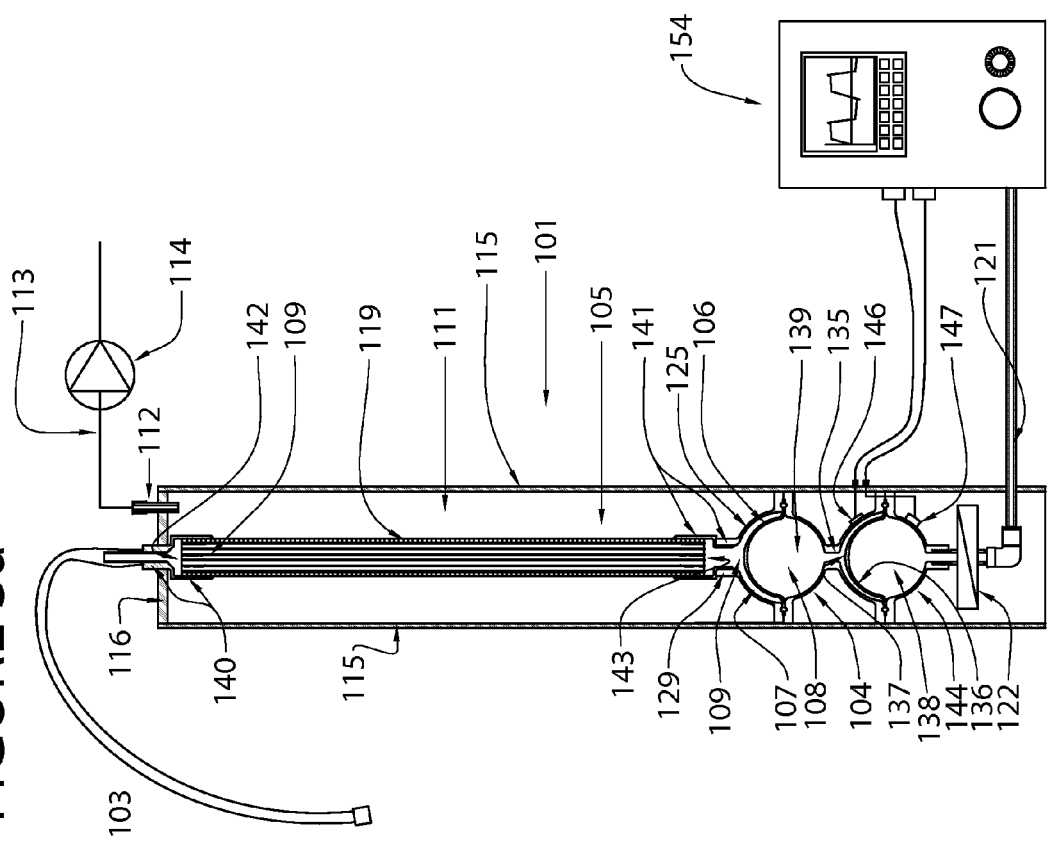
FIG. 3a shows a sectional view of an example of a enclosed filtration system being used with a dual pump system in which both pumps are diaphragm pumps.

FIG. 3a shows an enclosed filtration system 101 that comprises a dual pump system which is an improvement over using only the diaphragm pump 104.

It can be seen however, that many features of the enclosed filtration system 1 as described in FIGS. 1a-1h are present in system 101 shown in FIG. 3a. For example, components 3, 4, 5, 6, 7, 8, 9, 11, 12, 13, and 14, in FIG. 1a are present as components 103, 104, 105, 106, 107, 108, 109, 111, 112, 113, and 114, respectively. Further examples are components 15, 16, 19, 24, 25, 29, 40, 41, 42, and 43, in FIG. 1a which are present as components 115 (albeit sufficiently long to include the second pump 144), 116 (although it needs cross hatching because sectional view), 119, 124, 125, 129, 140, 141, 142, and 143, respectively. All of the foregoing components common to FIGS. 1a and 3a are also present in FIG. 3b.

In FIG. 3a, however, a second pump 144 is incorporated, to form a dual pump system, the two pumps connected in series through conduit 135. Conduit 135 may be short, minimizing the length of the connection between the two pumps as in FIG. 3a; this allows combining the entire enclosed reactor system with both pumps, to be combined into one module. Conduit 135 may be long, allowing separation of the two pumps as in FIG. 3b. Either choice of conduit allows greater flexibility as to the choice of method of driving the pump, including but not limited to the use of air, motor drives or other mechanical devices.

Figure 3B:
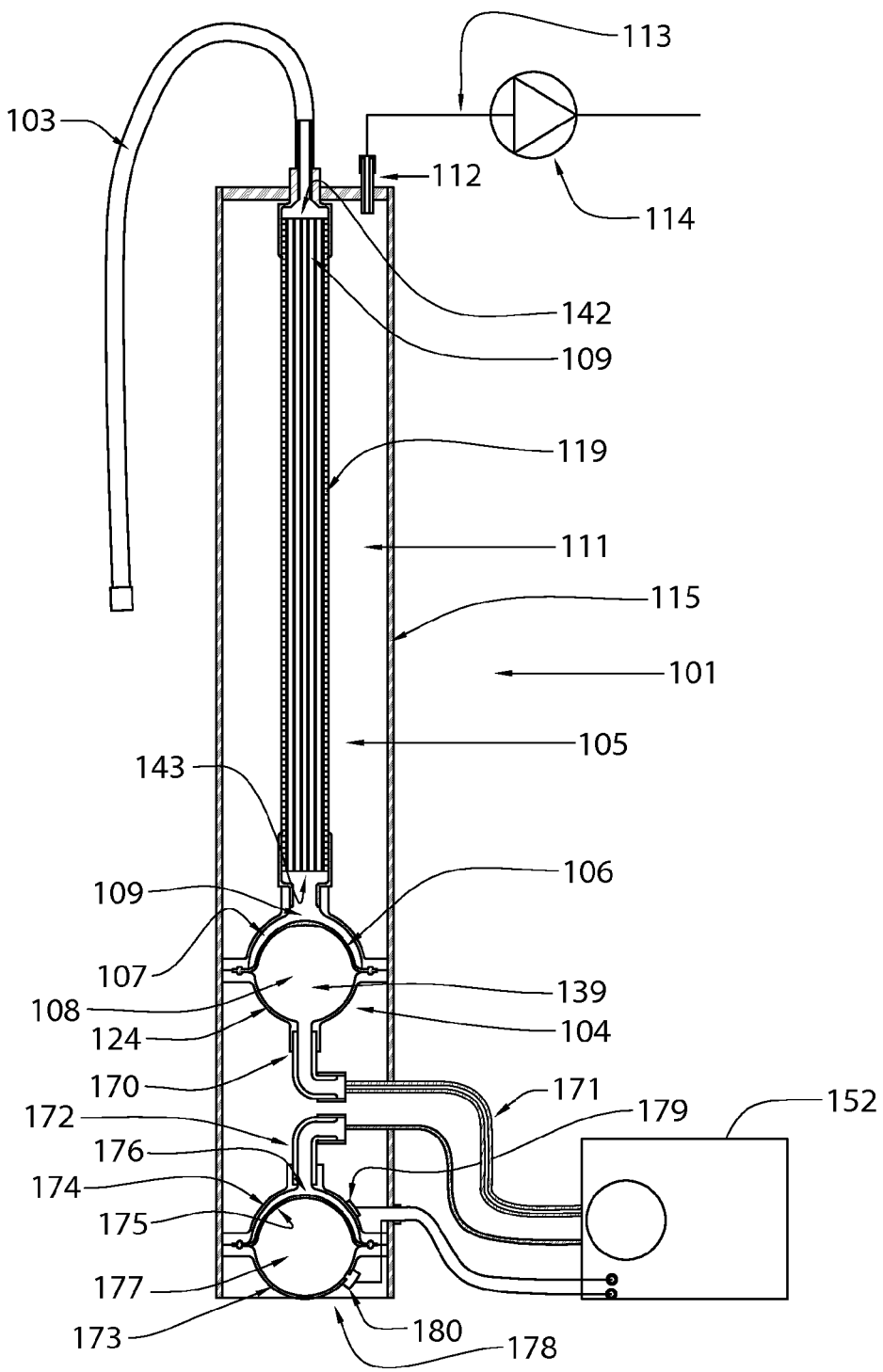
FIG. 3b shows a sectional view of an example of a enclosed filtration system being used with a dual pump system, where the two pumps are diaphragm pumps connected by a connector line controlled by a peristaltic pump.

In FIGS. 3a and 3b, the examples of the dual pump system show the use of a second pump 144 that is similar to the first pump 104, i.e., is also a two-chambered diaphragm pump. Like first pump 104, second pump 144 contains two chambers 137 and 138 separated by a diaphragm 136. Chamber 107 (also referred to herein as the "pump reservoir chamber") in the first pump 104 remains the same as previously described. It continues as a reservoir for receiving or expelling retentate flowing from or to a vessel (see for example vessel 102 in FIG. 1a); however, unlike the air driven system previously described, chamber 108 (also referred to herein as the "interface chamber of the first pump") in the first pump 104 connects with chamber 137 (also referred to as the "interface chamber of the second pump) of the second pump 144 through conduit 135. In addition, chamber 108 of the first pump 104, chamber 137 of the second pump as well as conduit 135 are preferably filled with a non compressible medium, preferably a liquid (The 139 refers to the location of the liquid when such an embodiment is used.) The second chamber 138 of the second pump 144 may drive the alternating pump 104 cycle, by using air flow to or from chamber 138 or by changing the volume of chamber 137 by some other mechanism as described. The second chamber 138 of pump 144 may be connected, optionally, via a sterile filter 122 and a line 121 to an air pressure controlling mechanism or device 154 that can exert a positive or negative pressure on the contents of that second chamber. In the case where gas is used, adding a gas to chamber 138 will drive the diaphragm 136 and cause the chamber to expand. This in turn will drive the liquid in chamber 137 outward through conduit 135 into chamber 108, expanding that chamber. As before, expansion of chamber 108 will drive the retentate in chamber 107 towards vessel 102, provided that the pressure in chamber 108 is higher than in vessel 102. Conversely, exhausting chamber 138 and reducing its pressure relative to vessel 102, will cause non compressible liquid at location 139 to flow from the first pump chamber 108 to the second pump chamber 137; in turn, retentate flows into the first pump chamber 107 from vessel 102. The following are some benefits of the described double pump system:

One benefit is that non-compressible liquid at location 139 may be varied depending on the application; for example, when used in a cell culture system, a non-compressible liquid at location 139 may be PBS (phosphate-buffered saline) or the culture medium itself. As further protection, non-compressible liquid at position 139 may be sterilized simultaneously with the entire enclosed reactor system or added into the pump chambers following sterilization in a sterile manner through a dedicated port (not shown). Therefore, should diaphragm 106 rupture, the non-compressible liquid at location 139 will spill into the retentate pathway 109 without harming the culture. Should either diaphragm 106 or 136 rupture separately, the culture will remain protected against total loss and may, in fact, be continued until the run is completed under a "safe" mode or allow the exchange of the damaged enclosed reactor system with a new enclosed reactor system.

Another benefit of the dual pump system shown in FIG. 3a involves the use of different size of chambers 107 and 137; for example, volume of chamber 107 can be made larger than chambers 108 and 137. This becomes useful if expansion of diaphragm 106 into chamber 107 has to limited, e.g., to prevent its extension to the wall of the chamber. Smaller maximum volumes of chambers 108 and 137, using an inelastic fluid coupling in between will displace a volume smaller than the maximum volume of chamber 107. Chamber 107 will remain unfilled by the difference in volumes Where previously, if chamber 108 was over pressurized, as was common at high flow rates, it was somewhat difficult to control diaphragm 106 position; the diaphragm would be commonly forced to extend to the walls of chamber 107 with potentially harmful effects on the cultured cells. In the modified system a second pump 144 with smaller chambers 137 would eliminate such over extension of diaphragm 106.

Some other benefits of the dual pump system involve added flexibility in controlling alternating tangential flow. In FIG. 3a, for example, where, the conduit 135 between the two pumps is inelastic, it provides the means of controlling the first pump 104 with a "remote" second pump 144. It becomes possible to incorporate sensors 146 and 147 into the second pump 144 for locating the position of the diaphragm within. That information may than be used for precise location and control of the diaphragm in the first pump 104. Where, with the use of a single pump, which has to remain sterile, the use or insertion of sensors is greatly limited. The use of a second pump removes that limitation. Positioning devices or sensors based on proximity, pressure, contact and optical amongst many others that may be incorporated preferably into the second pump without affecting the first pump or the culture within and with minimal effect on the process; this may be achieved before or after sterilization of the system since the two pumps are separated by an impermeable diaphragm. In addition, the use of the second pump opens the possibility of using sensitive sensors or positioning devices that otherwise may be damaged by the sterilization process; in such cases, the first pump could be sterilized by usual means, while the second pump could receive labile, unsterile sensors. Placement of sensors into the second pump is less critical since, as indicated, the pumps are separated by an impermeable barrier. By retaining the liquid coupling provided by the liquid at location 139 between the two pumps, it becomes possible to include agents in the liquid that could neutralize potential contaminants. The proposed system would protect the culture from contamination while retaining a high degree of pump control.

Another benefit of the dual pump system, as indicated, involves the ability to couple the enclosed reactor systems to energy sources other than compressed air or vacuum. One may couple the first pump 104 to a second diaphragm pump 144 through a liquid coupling as to a second pump 144 where the second pump drive system is provided by an electric motor as shown in FIGS. 3b and 3c.

FIG. 3b shows second pump 178 connected via an electric (here peristaltic) pump 152 to first pump 104. The liquid flow between the second pump chamber 176 and the first pump chamber 108 is generated by an electric pump 152 (for example, a reversible peristaltic pump), through conduit 171, for example tubing, which connects to the interface chambers of both pumps. The peristaltic pump 152 would pump the liquid from chamber 176 to chamber 108 in one direction, "pressure" cycle. When the liquid in chamber 176 has been pumped out, a sensor 179 on chamber 176 would signal for change in pumping direction. Similarly, sensor 180 would signal the end of the "exhaust" cycle. Any number of pumping mechanisms may replace a peristaltic pump. Numbers in FIG. 3b that also appear in FIG. 3a represent many, but not all, components common to the systems in the two figures.

Other components of the system in FIG. 3b are first pump connector tube 170, second pump connector tube 172, second pump housing components 173 and 174, second pump diaphragm 175, the first chamber (interface chamber) 176 of the second pump, second chamber 177 of the second pump FIGS. 3c and 3d show a variation of the dual pump system of shown in FIG. 3a. FIGS. 3e and 3f show another variation of the dual pump system of shown in FIG. 3a. The second pumps in FIGS. 3c-3d and their structures are well known in the art.

In FIGS. 3c and 3d, the second pump 644 is a piston pump. There is liquid coupling 621 (e.g. tubing) between the two pumps of the dual pump system. (A cam mechanism, shown in FIGS. 3c and 3d in two different configurations (on the left and right of the Insert respectively) with 638, 630 and 634 numbering its component parts in its two configurations, is connected to the motor drive shaft 630 and may be used to generate an eccentric stroke via lobe 634, which when coupled to piston 636 of the second pump 644 (also referred to as the piston wall of the second pump), may be used to generate the exhaust and pressure strokes. The pressure cycle will be generated as the cam 638 moves the piston 636 into pump chamber 637, expelling the contents in that chamber towards chamber 108 in the first pump 104. The exhaust cycle is generated by the continued rotation of the cam mechanism and withdrawal of piston 636 from chamber 637; in the process, chamber 637 expands receiving fluid flowing from chamber 108. The volume of chamber 637 may be set to equal the volume of chamber 108, thus setting the diaphragm displacement stroke of the first pump 104; furthermore, fluid flow rate could then be accurately controlled by controlling the electric pump rotational speed.

FIGS. 3e and 3f demonstrate another example of the second pump 656 being a piston pump here driven by a reversible screw drive 658. The reversible screw drive is coupled to a motor drive shaft 652. The linear motion of piston 653 (also referred to as the piston wall of the second pump) within pump housing 657 is than be established by the motor rotation rate, size of the pump chamber 654 and the pitch and length of the reversible screw 658. The threaded screw 658 may be coupled to piston 653 directly or indirectly; in the first case, the screw may be coupled to the piston by passing through threaded opening 659 in the piston 653, so that rotation of the screw causes the piston to move; in the second case, the piston is added to an unthreaded part of the screw shaft 658, not shown. A separate, threaded coupling is placed on the threaded portion of the shaft like in the first case, and like the first case rotation of the shaft causes the threaded coupling to move. A union between the threaded coupling and piston imparts the movement of the threaded coupling on to the piston. The indirect coupling is preferable by simplifying sealing between surfaces. Where sealing a threaded coupling can be complicated, sealing a round tubular object, piston opening 659, against a round shaft, part of the reversible screw 658, using an "O" ring, a gasket, mechanical coupling, etc. is much simpler and reliable. Similarly, the peripheral diameter of the round piston can be sealed against the round inner pump chamber wall 657. It is understood that pump chamber 654 in FIGS. 3e and 3f and chamber 637 in FIGS. 3c and 3d must be sealed in order to transmit their energy through conduit 651 to the first pump chamber 108. Elimination of leaks allows accurate control of liquid displacement or flow control to and from chamber 637 and chamber 108. There is a liquid conduit 651 (e.g. tubing) for the two pumps of the dual pump system.

The second pump e.g., pump 144, need not assume a specific shape or be composed of specific materials as long as it serves as means for reversibly pumping liquid into chamber 108 of the first pump 104.

Note that in FIGS. 3c-3d and FIGS. 3e-3f, 636 and 653, respectively, are movable pistons, the center hash representing an "O" ring or some other gasket. Chambers 637 and 654 are similar to chamber 7 in FIG. 1a. Liquid in those chambers will flow from those chambers to the first pump chamber 8, to drive the diaphragm in the first pump. In FIGS. 3e-3f, 658 is a reversible screw that drives piston 653 reversibly.

By their nature, the cam or reversible screw set the stroke of the piston; so as the motor is turning, the piston moves back and forth by a set distance. With an air driven diaphragm pump or reversible peristaltic pump as in FIGS. 3a and 3b, the controller needs to know when the stroke ends, therefore, one uses a device such as a sensor to inform the controller of when the cycle ends and its time to reverse direction.

Any numbers in FIGS. 3c, 3d, 3e and/or 3f that also appear in FIG. 3a represent components common to the systems in which they appear. All common components not marked by numbers are nevertheless recognizable as common components.

The pump descriptions herein do not limit the number of pumps that may be used in series or parallel with the first pump 104. For example a third pump may be used to drive a second diaphragm pump by a non-compressible coupling. The second diaphragm pump may than be coupled to the first pump, also, through a non-compressible coupling. The third pump may be a piston or diaphragm pump and driven by an electric motor or some other means; for example, chamber 138 of second diaphragm pump 144 in FIG. 3a could be coupled to the third pump's piston or a diaphragm chamber through a liquid conduit, as previously described. Chamber 138 would cycle in accordance with the cycling of piston or diaphragm of third pump. The second pump 144 may than serve to drive the first pump 104, through a liquid coupling, as previously described. The advantage of such a system is the ability to fully sterilize the first and second diaphragm pumps as well as the liquid connection between them and yet maintain a none sterile liquid connection between the second and the third pump. In this manner, one can retains a sterile environment should either diaphragm in the first pump or the second pump rupture and at the same time retain the pumping accuracy and control offered by an electric pump. Such a system could offer the high level of reliability require in dialysis applications, or some other medical or critical, none medical, application.

The Modifier Module Invention

The invention is a modifier module designed for use inside filtration and bioreactor systems so as to modify some (or less commonly, all) of the components in the system.

The modifier module (preferably columnar in shape), comprises in one general aspect:

1) a scaffold; and
2) a population of modifier agents bound to said scaffold.

Optionally, the module further comprises a semi-permeable membrane that surrounds the population of modifier agents and, in conjunction with the scaffold, encloses that population.

The modifier module (preferably columnar in shape), comprises in another general aspect:

1) a scaffold;
2) a semi-permeable membrane partially or completely surrounding said scaffold in a manner that allows a compartment between said membrane and said scaffold; and
3) a population of modifier agents in said compartment; wherein the semipermeable membrane is not permeable to the agents but permeable to molecules small enough to pass through the membrane; and wherein the modifier agent population is retained within the compartment (preferably stacked against the scaffold).

Examples of modifier agents are antibodies or enzymes.

A modifier agent population bound to the scaffold can coat the surface of the scaffold (e.g., where the agent is a resin).

A modifier agent population may be part of or attached to beads, particularly where it is not bound to the scaffold but rather held in position within the membrane-scaffold compartment.

The modifier agent is preferably selected from the group consisting of an antibody, an enzyme, a non-enzymatic catalyst, a receptor, a ligand, a chemical that will modify a biological molecule, an affinity resin, and an ion exchange resin, a biological receptor, a ligand that will bind to a biological receptor, and a chemical that will modify a biological molecule.

Of particular interest are modifying agents that can bind or modify components, such as those that may accumulate in the kidneys and blood to undesirable levels and can be removed using a filtration system, such as the enclosed filtration system described herein. Components that could be considered undesirable include, but are not limited to, toxins generally, inflammatory proteins (such as plasma C-reactive protein (CRP) and amyloid A (SAA)), colony stimulating or growth factors, chemokines, (such as a member of the leukocyte chemoattractive cytokines, also known as CXC, CC, C and CX3C chemokines), pro-inflammatory interleukins (for example, IL-1, IL-6), tumor necrosis factor-$\alpha$ (TNF-$\alpha$)], pancreatic secretory trypsin inhibitor (PSTI), HDL cholesterol (HDL), low-density-lipoprotein (LDL) cholesterol, hormones, urea, salts, drugs, and vitamins.

A modification process of the invention comprises the steps of:

(1) contacting a fluid with a modifier module of the invention, and
(2) filtering the fluid using a semi-permeable membrane, wherein the modifier module is within either a chamber of a filtration system or a chamber of a bioreactor system, preferably an enclosed filtration system or enclosed bioreactor system of the invention.

With the enclosed filtrations systems of the invention described herein, the preferred location of the modifier is the reactor chamber, and the preferred sequence is that step (2) follows step (1). In one embodiment, the process further comprises a step (3) where the filtered and modified fluid is administered to a human, especially either via dialysis, by injection, or orally.

Modification of Reactor Chamber Fluid and Other Fluids

A potential application of a modifier module 351 is shown in FIG. 6a. In that Figure, the reactor chamber 311 is designed to accept a modifier module 350, whose function is primarily to affect the composition of fluid in that chamber. Accordingly FIG. 6a illustrates an embodiment of the enclosed filtration system of the invention.

Many features of the enclosed reactor system 301 in FIG. 6a are present in system 1 of FIGS. 1a, 1b, 1c, 1d, 1e and 1f. Components 303, 306, 307, 308, 309, 313, 314, 315, 316, 321, 322, 323, 324, 325, 326, 327, 329, 335, 340, 341, 342, and 343, are the same as components 3, 6, 7, 8, 9, 12, 13, 14, 15, 16, 21, 22, 23, 24, 25, 26, 27, 29, 35, 40, 41, 42, and 43 respectively, in FIGS. 1a, 1b, 1c, 1d, 1e and 1f. Additional marked components in FIG. 6a are discussed below.

A modifier module may, for example, be constituted as follows: The primary parts of the modifier module may consist of a scaffold body 354 and a modifier agent population 352.

Optionally, the module further comprises a semi-permeable membrane that surrounds the population of modifier agents and, in conjunction with the scaffold, encloses that population.

Semi permeable membrane 353 is a membrane across which constituents from chamber 311 cross to react with modifier agent 352. Bellows-like cover 362 surrounds the scaffold body to isolate it from contamination from the external environment, (see FIGS. 6a, 6c).

The entire modifier module needs to be enclosed to protect it against contamination. Cover 362 is inner most protective layer that is flexible, bellows like. The bellows 362 (FIG. 6c) is represented in collapsed form in FIG. 6a. As the modifier is inserted into reactor chamber through opening 358, covering 362 (or 370) collapses during insertion without exposing the modifier within. Coverings 365 and 366 provided a rigid enclosure. Positioners 367 serve to position and retain the modifier within the rigid housing 365. Body 355 is fixed by the ledge 367.

Channel 358 in adapter 356 directs the modifier scaffold end 354 into the reactor chamber through port 331 in the reactor top.

The modifier agent population 352 may be part of the scaffold body 354, directly attached to it or unattached to it but enclosed (and preferably stacked) against the scaffold body 354 with a retaining porous (fully permeable) or semi porous (semipermeable) membrane 353.

The representation of the modifier agent populations 352 in the FIGS. 6a-6d is highly schematic since the agents are so much smaller than the filter systems, scaffolds, and other items represented in those Figures. In FIG. 6c, each agent is represented by a small hexagon. If the modifier agent is an antibody, for example, the number of hexagons needed to represent the agent population would be so great that the hexagons would not be recognizable. However, the representation in FIG. 6c provides the clearest basis among FIGS. 6a-6d for discussing the geometric relationship of the agents to the scaffold and any semi-permeable membrane surrounding the agents.

In FIG. 6c, the agent population 352 consists of a two sub-populations: a sub-population of agents touching the scaffold 354 and a sub-population of agents touching the semi-permeable membrane 353. As such it can be considered to be a schematic representation of a stacked agent population retained within the compartment by the membrane and stacked against the scaffold 354.

In FIG. 6c, Elimination of the sub-population of agents that touches the semi-permeable membrane 353 would provide a schematic representation of the embodiment where the agent population is bound to the scaffold. In that case, the semi-permeable membrane 353 optionally may be removed—the decision being based on part on whether a filtering by such a membrane is desired.

FIGS. 6a, 6b and 6d, provide in schematic fashion a representation of a population of modifier agents bound to the scaffold.

Part of the scaffold 354 may function as a scaffold structural "head" 355. As illustrated in FIGS. 6b and 6c, the scaffold head can serve as a place of attachment for membrane 362. The scaffold head can, as shown in FIG. 6c, have a greater diameter at the top of the scaffold than at the lower portion of the scaffold, head, thereby providing a lip that can sit on the module support ring 367 which ring is attached to the housing 365 of storage case 371, a case adapted for storing a sterilized modifier module until the module is needed.

In FIG. 6c, the storage case 371 comprises additional features designed to hold the modifier module in place: A lower adapter 356 whose position within housing 365 is fixed by the circular holder ring 368 attached to both the holder 356 and the housing 365 of storage case 371.

The objective of membrane 353 is to retain the modifier agent population 352 against the scaffold and allow fluid exchange across its wall. Therefore, If module 351 shown in FIG. 6c is inserted into chamber 311 of system 301 in FIG. 6a as the module 351 in that Figure, fluid in reactor chamber 311 will be free to flow across porous membrane 353, and to contact the modifier agent population 352; thereby, allow constituents in the reactor chamber fluid to react with the modifier agent population. The modifier agent population may comprise any agents capable of reacting or interacting with selected constituents in the reactor chamber fluid. For example, the modifier agent may be an antibody, in which case it would be chosen to be one reactive against some component in the reactor chamber fluid. Alternatively, however, it may be more effective to link the agent, such as an antibody, to some solid resin. The resin in that case may be directly linked to, or coated onto, the scaffold 354. The screen pore size would be smaller than the resin to retain the resin and allow free exchange across its surface. Both ends of the screen or membrane 353 would be sealed against the scaffold body so as to fully enclose and retain the resin.

Filtrate generated during the process may be allowed to flow freely or in a selective manner through pores 318, in barrier 319, into the reactor chamber 311, immersing the modifier module 350. If we assume that an attached antibody on the resin is against a secreted agent produced by cultured cells, then the agent will be captured by the antibody and selectively removed from the reactor chamber fluid. The system 301 illustrated in FIG. 6a has many uses, one of which is dialysis. A catheter provides, as a result of its insertion in a person's vein, a direct or indirect fluid connector 333 between the system and the person. In this example, the reactor chamber is provided with a defined dialysate solution. Such a solution may be customized to protect the user, to assist in the dialysis process, to enhance the efficacy of the modifier or effect the process in some other way. The retentate chamber 345 of the filter element (e.g., the fibers of a HF filter cartridge) in this case may be a micro filter membrane or ultra filter membrane. Barrier (wall) 319 may also be selective in nature to facilitate further fractionation of blood constituents such that only the desired molecules escape into the reactor chamber to react with the modifier. Blood will cycle reversibly between the alternating pump 304 and the venous system, through the filter element 305. As previously described, during the alternating tangential flow filtration cycle, fluid not only flows through the lumens of the hollow fibers but it also facilitates bidirectional fluid flux across the filtration membrane 317 between the retentate and filtrate chambers, across barrier 319 between the filtrate and reactor chambers 310 and 311, respectively, and across barrier 353 or other barriers that are part of the modifier module, in both directions; the alternating flow therefore enhances mixing between system compartments. Using hollow fibers with the appropriate MWCO (molecular weight cutoff) may be used for selective retention of essential constituent of blood, cellular fraction, proteins, etc. Also depending on the MWCO of the membrane, other, selective, molecular constituents may be allowed to exchange across the membrane/selectively permeable barrier 317 surface. It becomes possible to allow urea, certain proteins, hormones, toxins, byproducts, etc, to exchange across filter membrane 317. Selective membrane 319 and potentially selective membrane 353 may be used to further regulate the flow of specified constituents from the filtrate chamber 310 to the reactor chamber 311. The selectivity of membrane/barrier 319 may be established by controlling its charge properties, permeability, porosity, chemical nature, etc. The configuration of barrier 319 may be modified to increase its surface area.

Once in the reactor chamber 311, the product of interest can freely exchange across barrier 353 to react or bind with the modifier agent population 352. Once bound, the selected product is prevented from returning into the retentate or blood stream. Another possibility is to use an enzyme(s) in place of an antibody as the modifying agent. The enzyme would be selective for a particular harmful component in circulation or to affect some critical metabolic reaction beneficial to the patient. If that component flows from the circulation across the selective membrane(s) into the reactor chamber, it would be available to react with the attached enzyme(s) modifier. The altered component, either inactivated or made more potent, will be free to exchange across barriers 353, 319 and 317 to reenter the retentate or blood stream or to react with a second modifier module (not shown) in the reactor chamber, for further modification or removal of fluid. In a similar manner, one can foresee many other uses for the described configuration of the invention, in the healthcare or other fields.

It is also foreseen that a sterile system may be supplied separately with a presterilized modifier module(s) 350 and 351. One has the choice from various modifier modules to further increase the flexibility of the system. It becomes possible to insert a selective modifier module 351 into the reactor chamber 311 as the need may arise or based on immediate requirements. This modular concept, in addition to providing the capability to select from a variety of potential modules 351, also provides the ability to use modifier modules 351 containing a labile modifier agent population 352; such as proteins, that cannot be normally sterilized preassembled with the system, but can be sterilized or sanitized by other less severe means; for example, assembly of the modifier module 351 separately may involve using steam, radiation, etc for the nonlabile parts of module 351, using filtration to sterilize the labile components and assembly of the two in a sterile environment. The use of antibiotics or other preservatives offer other sanitization options. Or one may store labile modifier agents in a stable form such as frozen or freeze dried, then prior to use the modifier agent population may be hydrated and activated.

It is possible that the insertion of the modifier module into an enclosed bioreactor system of the present inventions may have to take place in the "field" in the open, in an unprotected, unsterile, environment, a procedure that has the potential to result in contamination the system. The enclosed bioreactor system described offer the capability of performing the procedure in an aseptic manner. Such connectors are commercially available the clean-pack (from Pall, Inc) and the DAC (from GE); such that, anyone familiar with the use of such connectors may effectively insert the modifier module into the enclosed reactor system in a sterile manner.

Product Concentration Device, System and Process

There is a growing list of products being produced by cell culture; the products may include proteins which may be natural or recombinant, cells, or any product that may be produced by the cellular synthetic machinery. The production cultures may be mammalian cells, insect cells, plant cells, yeast, bacteria etc. . . . . Considerable effort has gone into improving methods for producing such cellular products; these include improvements in the methods of growing cells, including, manipulating the cells to express product, improving the ability to sustain cultures in production phase at very high cell concentrations, improving stability of the process as well as other improvements. Today there are cultures that can be grown to very high cell concentrations, >$100 \times 10^6$ cells/ml (greater than 100 million cells/ml) which generate product at ever increasing concentrations. A key bottle-neck that results from such improvements is in the ability to harvest the product efficiently without damaging the product or the culture. Currently, product harvesting is achieved in a number of ways. The following are some examples of product harvesting: (1) In cases where the production culture is taken to its termination, (e.g. batch, fed-batch, limited perfusion), and where the product is soluble in the culture medium, the entire culture is subjected to a fractionation process that separates cells from media plus product. The separation process is typically achieved by centrifugation or by filtration. (2) In a continuous culture process, such as "perfusion", the product may be separated from the cultured cells continuously. The separation process may involve filtration, cell settling or centrifugation. The product is removed from the culture and processed appropriately, while the cells are retained in the culture vessel. (3) Continuous fed batch is a process, demonstrated by Kearns (U.S. Pat. No. 5,286,646), that uses a filter with pore size capable of retaining the cells and product in the culture, while allowing harvesting of material smaller than the pore size of the filter. Kearns demonstrated that removal of the lower molecular weight filtrate supports continued cell growth and increased product formation.

In examples (1) and (3) of product harvesting, the cells and product are maintained in the culture until its termination. Approaching its termination, the culture typically loses viability and cell integrity is unable to be maintained; it is also a period when increasing number of cells rupture and release their content into the culture. The viability and integrity of the cells typically begin to deteriorate significantly prior to the end of the culture. The product may, therefore, be subjected to the toxic environment of the culture, subjected to digestive enzymes, shear, temperatures and other conditions not ideal to the stability of the product. Other effects, particularly in continuous fed batch (example (3)), where cells and product may be at very high cell concentration, is the potential for formation of multimers, modification of protein glycosylation, as well as other potential factors that may modify the product. The effects of such adverse conditions on the product will vary from product to product. Some products are highly unstable and rapidly deteriorate in culture; other products are more stable and can tolerate such adverse condition for longer periods.

In example (2) of product harvesting, perfusion, the product can be rapidly removed from the toxic environment of the culture and stored in an environment that would preserve its stability, including storage at reduced temperatures, pH stabilized media, etc. Two primary disadvantages of the perfusion are: one, lower product concentration in the harvest, as the product is not allowed to accumulate in the culture; two, large volumes of harvest that requires storage and processing to recover the product. It is preferable, therefore, to take advantage of the process which removes the product continuously from the toxic environment of the culture, yet provide the product continuously in concentrated form at reduced volumes. Such a system is described herein.

Figure 10:
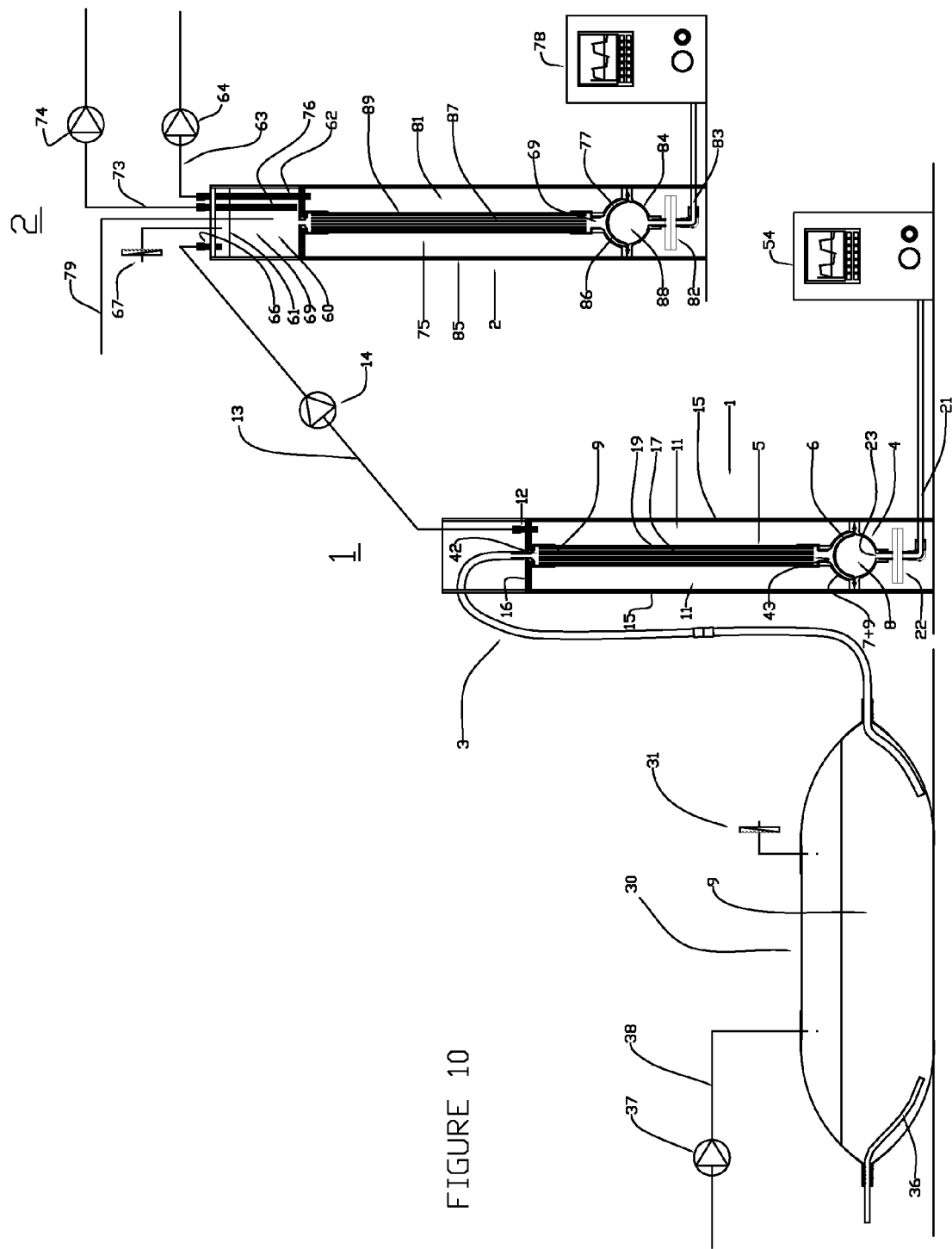
FIG. 10 shows a sectional view of an embodiment of the system of the invention for modification or concentration of a cell-depleted filtrate.

FIG. 10 shows a system with a continuous two stage system, Unit 1 and Unit 2. In the first stage, Unit 1, the product is continuously removed from a culture, while retaining the cells in the culture. In the second stage, Unit 2, the product stream from Unit 1 is concentrated by a filtration device, preferably an alternating tangential filtration device, capable of retaining and separating the product from lower molecular weight constituents, primarily water in the product stream.

In FIG. 10, a culture vessel or bioreactor system 30, analogous to vessel 2 shown in FIG. 1a, is connected to input line 3 of separation device 1 (also referred to as Unit 1).

While the cell separation device shown in Unit 1, FIG. 10, is a filtration device based on an alternating tangential flow filtration system (described earlier and in U.S. Pat. No. 6,544,424), it is not limited to that particular system or to filtration. Unit 1 may constitute any cell separation device capable of retaining cells in reactor 30 while permitting the product and waste media to be removed from the culture; such devices may include ones that operate based on cell settling, centrifugation, electric or magnetic fields as well as other techniques. Therefore, while all such cell retention devices retain the cells in vessel 30, they also generate a cell depleted steam, (henceforth, also labeled "product stream" or "filtrate stream"), that contains the product of interest as well as the waste generated by the culture.

Although not limited to any particular cell retention or cell separation system, the alternating tangential flow system shown in FIG. 1a and as Unit 1 in FIG. 10 is used to illustrate the process of the invention. In Unit 1, a filter element is used with pore size that retains the cells and allow most biomolecules including the product (e.g., IgG of 150 kDa) and waste media to be removed in the filtrate stream. A filter element consisting a membrane with 0.2 micron pore size may be such a filter. In FIG. 10, the filtrate product stream emerging from the filter into the filtrate chamber 17 of filter element 5 may be further directed through channels in filter housing 19 of filter element 5 and collected in chamber 11. The filtrate stream can be removed directly from the filtrate chamber 17 within filter element 5 or from chamber 11. In the latter case, the filter stream is removed through port 12 into tubing 13 which directs the filtrate stream to Unit 2 reservoir 60 via port 66. A pump 14 controls the rate and direction of fluid transfer between separation Unit 1 and separation Unit 2. Pump 14 therefore serves as a one-way valve, preventing back flow of fluid from Unit 2 to Unit 1; alternatively, a non-pump one way check valve, (not shown), may replace pump 14 in line 13 to prevent such back flow.

Unit 2 may be any filtration system, including one based on dead end filtration, or tangential flow filtration, but preferably one based on alternating tangential flow filtration. As illustrated in FIG. 10, like the previously described alternating flow filtration system of Unit 1, Unit 2 contains an alternating tangential pump 84 capable of generating an alternating tangential flow between the pump liquid chamber 77 and reservoir 60 through filter element 75. As before, controller 78, using conduit 83, alternately pressurizes or depressurizes chamber 88 of the pump relative to reservoir 60. A flexible diaphragm, bladder or air column 86, allows the transfer of pressures in chamber 88 of the pump to chamber 77. The resulting alternating pressures changes in chamber 77 relative to reservoir 60, is used to generate and control alternating tangential flow or reversible flow between chamber 77 and reservoir 60 through a filter element 75.

Reservoir 60, in addition to providing a storage container for micro-filtrate 69 from Unit 1, also serves as a reservoir for the fluid 69 flowing reversibly from and to pump chamber 77. Fluid reservoir 60 can serve as a single liquid reservoir or interconnected with two or more liquid reservoirs (not shown) through connecting conduits (not shown) which allows fluid flow between such reservoirs. The reservoirs may serve as temporary storage buffer for filtrate generated in Unit 1 or for modifying such filtrate prior to addition to reservoir 60; whether singly or in multiples the term reservoir 60 is applied. Additionally and optionally, the content in fluid reservoir 60 may be monitored by probes to determine fluid level 61 within the reservoir, to determine its pH, temperature, turbidity, for spectroscopic analysis or conductivity as well as other parameter; such information may be used to adjust indicated parameters to the desired settings by known methods. Conditioning the fluid in reservoir 60 may be used to stabilize the content in the reservoir or to facilitate separation of desired constituents. A device such as a manifold invention described in the present application (FIGS. 5*a* and 5*b*) connected to reservoir 60 through line 79 may be used to monitor the conditions in reservoir 60 and to affect such conditions. Reservoir 60 while passive in nature, serving as a container for filtrate flowing from Unit 1, one can also envision a more active system, where reservoir 60 consists of a second alternating tangential flow pump, where fluid flowing from pump 84 is received in such second pump liquid chamber; conversely, the second pump may be pressurized to cause fluid in its liquid chamber to through the filter module 75 to pump 84 liquid chamber 77. Such reversible and alternating flow may be used in a manner that would maintain the filtration process in Unit 2 under continuous positive pressure, which may be beneficial in many applications. Furthermore, in yet another variation a knowledgeable user may invert the process described above, where reservoir 60 is shown in the preferred form and its preferred use; for example, its conceivable that chamber 81 in Unit 2 may serve as a container for micro-filtrate 69 emanating from Unit 1, while reservoir 60 may serve as an ultra-filtrate reservoir; in which case, the filtration direction though filter element 75 of Unit 2 will be conducted in reverse. (Reservoir 60 need not be attached to housing 2, a conduit from the entrance end of the filter element 75 to reservoir 60 is also possible.) Fluid 69 would be concentrated in chamber 81 and externally to the hollow fiber in chamber 17, while low molecular stream filtered through the ultra-filter will flow into the lumen of the hollow fibers and into reservoir 60 from where it can be removed through line 73. The concentrate can be removed from chamber 81 through line 64, which extends into chamber 81 through tubing 62.

Hollow fiber module 75 within the housing 2 of Unit 2 may be selected for desired properties, specifically for its pore sized; for example, a pore size may be selected that will retain constituents, such as the product, larger than the pore size; while constituents smaller than the filter membrane pore size and water will pass thorough the membrane as ultra-filtrate; for example, an ultrafiltration membrane with a 50 Kda pore size is commonly used to separate proteins such IgG antibodies from smaller MW constituents. Therefore, micro-filtrate or product stream 69 within reservoir 60 flowing reversibly between said reservoir and pump chamber 77 through such a selective hollow fiber module can be used as an efficient filtration process to retain the product but allow particles smaller than the filter pores, particularly water to be removed from the product stream 69. The resulting ultra-filtrate or "waste stream" can be collected in the filtrate chamber 87 of the filter element 75. The filter element 75 may provide openings 89 in its enclosure for the filtrate to flow from the inside of module into a filtrate collection chamber 81 enclosed peripherally by the Unit 2 containment wall 85. From chamber 81 the filtrate may be harvested through port 62 and line 63 and pump 64. Alternately the filtrate may be collected directly from the filtrate chamber 87 bypassing chamber 81. The rate of ultra-filtrate collection through port 62 and line 63 may be controlled with harvest pump 74. Removal of ultra-filtrate and particularly water from the micro-filtrate product pool 69 will concentrate the product within reservoir 60. (The product can be concentrated two fold, preferably it may be concentrated four fold, more preferable still, the product may be concentrated more than ten fold, The volume of suspending medium will be decreased inversely to the concentration). The rate of concentration of the product will be determined not only by the rate of water removal from the micro-filtrate product pool 69 but also by the following factors: Product concentration will be effected by the rate of micro-filtrate flow from Unit 1 into pool 69, diluting the product in the pool. Product concentration in pool 69 will also be effected by the rate of concentrate removal from pool 69; such removal may be achieved through port 76, line 73 and pump 74. Product concentration in pool 69 may also be effected by optional addition of fluids from an external source, as needed to condition the concentrate to facilitate its further processing. In summary, the process provides the user the means for continuous concentration of the product, the means for controlling product concentration, including the rate of product concentration and the rate of product harvest in its concentrated form.

The system offers the ability to maintain a culture in perfusion to achieve high cell concentrations and high product through-put. It offers the ability to remove the product from the toxic environment of the culture in a vessel 30 connected to line 3. Optionally it offers the ability to condition the product stream produced by Unit 1. It offers the ability for continuous concentration of the product in Unit 2 and provides a continuous stream of concentrated product. It provides the means for controlling the indicated flows. Unit 2, in part or fully, may be maintained at lower temperature to preserve the product; additionally, the emanating concentrated product stream may also be preserved at lower temperature for subsequent processing or for immediate modification as required for purification or other procedures.

In a general aspect, the product concentration comprises:
1) a hollow fiber filter element (or module; preferably a cylindrical hollow fiber filter cartridge) said filter element comprising an entrance end and an exit end, said filter element further comprising a plurality (more than one) of filtration retentate chambers, each filtration retentate chamber being an open-ended hollow fiber, wherein each fiber comprises a semi-permeable outer wall, said filter element further comprising a filtrate chamber, said filter chamber comprising a filtrate chamber inner wall and a filtrate chamber outer wall, such that said filtrate chamber encloses said fibers but does not block their open ends, such that the semi-permeable outer walls of the fibers are also part of the filtrate chamber inner wall, said filtrate chamber outer wall optionally comprising pores or outlet(s) for flowing the filtrate from the filtrate chamber to an intermediate or final collection vessel;

2) an alternating flow pump, said pump said pump connected to the exit end of the filter element so as to permit fluid from the pump to enter the filtration retentate chambers and fluid from the retentate chambers to enter the pump (said pump, for example, comprising a pump housing, two chambers, and a diaphragm separating the chambers);

3) A reservoir connected to said filter element entrance end, so that fluid can flow between said reservoir and the retentate filtration chambers;

wherein the retentate chamber fibers are disposed in parallel to the center axis of the filter element (the center axis extends through the center of the cylinder from one filter element end to the other, wherein those fibers each have an entrance at the entrance end of the filter element and an exit at the exit end of the filter element. (In one embodiment, the pump does not comprise an open drainage tube that would allow removal of retentate from the filtration retentate chambers).

In the case where the filtrate chamber outer wall contains pores, the production concentration device further comprises a filtrate collection chamber, said filtrate collection chamber disposed so that it at least partially encloses both the filtrate chamber and the filtration retentate chamber in a sealed manner but does not block fluid flow in and out of the filter element entrance, said filtrate collection chamber comprising a filtrate collection chamber inner wall and a filtrate collection chamber outer wall, said filtrate collection chamber inner wall comprising the filtrate chamber outer wall;

In the case where the filtrate chamber wall contains pores, the production concentration device may further comprise a filtrate collection chamber harvest line and/or a reservoir adapter line, said filtrate collection chamber harvest line connected to the filtrate collection chamber so as to allow fluid to be harvested from the filtrate collection chamber, said reservoir adapter line connected to the reservoir so as to allow fluid to be harvested from the reservoir adapter.

In a particular aspect, the product retention device further comprises a line (tube) connected to the reservoir so that fluid can enter the reservoir from an external source of fluid; wherein a one-way valve and/or pump connected to or in said line so that fluid can flow from the external source into the reservoir but preferably not in the reverse direction.

In another general aspect of the invention, a product retention system related to the product retention device for modification or concentration of a cell-depleted filtrate, comprises:

1) a product concentration device as specified in Claim 1 or 2;

2) a cell depletion device, said cell depletion device capable of generating a cell-depleted product fluid, said cell depletion device comprising a chamber where the cell-depleted fluid resides, said chamber connected to the line (tube) of the product concentration device.

In a particular aspect of the product retention system, the chamber is connected to the line of the product concentration device.

In a particular aspect of the product retention system the cell depletion device has a component selected from the group consisting of a filter, a centrifuge or other cell separation devices.

In a particular aspect of the product retention system, the cell depletion device comprises a filter, said filter capable of preventing the passage of cells while allowing the passage of product in fluid.

In a particular aspect of the product retention system, cell depletion device comprises a centrifuge, said centrifuge capable removing cells from a portion of a fluid comprising product, thereby creating a cell-depleted product fluid.

In a related process, in a general aspect, the process comprises utilizing an aforementioned product concentration device such the result of the process is to generate a product concentration greater than the product concentration in the cell depleted fluid at the start of the process.

What is claimed is:

1. A product concentration device for modification or concentration of a cell-depleted filtrate, the device comprising:
   a filter cartridge comprising:
      an entrance end opposing an exit end and a cartridge wall; and
      a retentate chamber comprising a plurality of open-ended hollow fibers each having a semi-permeable outer wall, wherein the cartridge wall surrounds the retentate chamber such that each end of the retentate chamber is at least partially unobstructed by the cartridge wall, and wherein a filtrate chamber is formed between the retentate chamber and the cartridge wall;
   an alternating flow pump connected to the exit end of the filter cartridge and configured to cause fluid flow between the retentate chamber and the pump in a first direction and a second direction; and
   a reservoir connected to the entrance end of the filter cartridge such that the connection comprises a fluid path between the reservoir and the retentate chamber, wherein the open-ended hollow fibers are aligned parallel to a center axis of the filter cartridge.

2. The device of claim 1, further comprising a filtrate collection chamber surrounding the filter cartridge such that at least a portion of the entrance end of the filter cartridge is at least partially unobstructed by the filtrate collection chamber.

3. The device of claim 2, wherein the cartridge wall comprises a plurality of pores.

4. The device of claim 3, wherein the filter cartridge wall and the semi-permeable outer wall of the plurality of fibers each comprise a pore size of about 0.2 micron.

5. The device of claim 3, wherein at least one of the cartridge wall and the semi-permeable outer wall of the plurality of fibers comprises a pore size of about 10 to 500 kDa.

6. The device of claim 1, wherein the device further comprises a conduit connected to the reservoir and to an external fluid source, wherein the conduit comprises a one-way valve configured to permit fluid flow from the external source to the reservoir.

7. The device of claim 6, wherein the one-way valve comprises a check valve.

8. The device of claim 1, wherein the device further comprises a conduit connected to the reservoir and to an external fluid source, wherein the conduit comprises a one-way pump configured to permit fluid flow from the external source to the reservoir.

9. The device of claim 2, wherein at least one of the filtrate chamber and the filtrate collection chamber comprises at least one outlet.

10. The device of claim 9, wherein the reservoir further comprises a reservoir conduit connected to the filtrate collection chamber.

11. The device of claim 1, wherein the filter cartridge comprises a cylindrical hollow fiber filter element.

12. The device of claim 1, wherein the reservoir further comprises at least one port configured to receive one or more probes for monitoring one of more of the following: a fluid level, a pH level, a temperature, and a turbidity.

13. The device of claim 1, wherein the device is configured to condition the fluid to stabilize the fluid in the device or to facilitate a separation of the fluid based at least in part on the monitoring.

14. The device of claim 1, wherein the alternating flow pump is directly connected to the exit end of the filter cartridge.

15. A system for modification or concentration of a cell-depleted filtrate, the system comprising:
a product concentration device comprising:
a filter cartridge comprising:
an entrance end opposing an exit end and a cartridge wall; and
a retentate chamber comprising a plurality of open-ended hollow fibers each having a semi-permeable outer wall, wherein the cartridge wall surrounds the retentate chamber such that each end of the retentate chamber is at least partially unobstructed by the cartridge wall, and wherein a filtrate chamber is formed between the retentate chamber and the cartridge wall;
an alternating flow pump connected to the exit end of the filter cartridge and configured to cause fluid flow between the retentate chamber and the pump in a first direction and a second direction; and
a reservoir connected to the entrance end of the filter cartridge such that the connection comprises a fluid path between the reservoir and the retentate chamber, wherein the open-ended hollow fibers are aligned parallel to a center axis of the filter cartridge; and
a cell depletion device configured to generate a cell-depleted product fluid, wherein the cell depletion device comprises a depletion chamber configured to store the cell-depleted fluid and is connected to the retentate chamber of the product concentration device.

16. The system of claim 15, further comprising a filtrate collection chamber surrounding the filter cartridge such that at least a portion of the entrance end of the filter cartridge is at least partially unobstructed by the filtrate collection chamber.

17. The system of claim 16, wherein the cartridge wall comprises a plurality of pores.

18. The system of claim 15, wherein the device further comprises a conduit connected to the reservoir and to an external fluid source, wherein the conduit comprises a one-way valve configured to permit fluid flow from the external source to the reservoir.

19. The system of claim 18, wherein the one-way valve comprises a check valve.

20. The system of claim 15, wherein the device further comprises a conduit connected to the reservoir and to an external fluid source, wherein the conduit comprises a one-way pump configured to permit fluid flow from the external source to the reservoir.

21. The system of claim 16, wherein at least one of the filtrate chamber and the filtrate collection chamber comprises at least one outlet.

22. The system of claim 15, wherein the cell depletion device is a cell separation device.

23. The system of claim 22, wherein the cell separation device is selected from the group consisting of a filter and a centrifuge.

24. The system of claim 15, wherein the cell depletion device comprises a filter configured to prevent passage of cells while allowing passage of a product in fluid.

25. The system of claim 15, wherein the cell depletion device comprises a centrifuge configured to remove cells from a portion of a fluid comprising product, thereby creating a cell-depleted product fluid.

26. A process of concentrating a cell depleted fluid, the process comprising:
providing a product concentration device comprising:
a filter cartridge comprising a retentate chamber within the filter cartridge, wherein the retentate chamber comprises a plurality of open-ended hollow fibers each having a semi-permeable outer wall, wherein the open-ended hollow fibers are aligned parallel to a center axis of a filter element;
an alternating flow pump connected to the filter cartridge and configured to cause fluid flow between the retentate chamber and the pump in a first direction and a second direction; and
a reservoir connected to the filter cartridge;
connecting the filter cartridge to a fluid source comprising a first product concentration;
pumping the fluid into the filter cartridge and into the retentate chamber, wherein the pumping causes a waste stream to pass through the semipermeable outer wall of at least one of the plurality of open-ended hollow fibers, thereby creating a product stream; and
pumping the product stream into the reservoir, wherein the product stream comprises a second product concentration, the second product concentration being greater than the first product concentration.

27. The process of claim 26, further comprising selecting a porosity of the semi-permeable outer wall such that the product is larger than the selected porosity.

28. The process of claim 27, wherein the waste stream comprises water and particles smaller than the porosity of the semi-permeable outer wall.

29. The process of claim 26, further comprising collecting the waste stream from a filtrate chamber arranged between the filter cartridge and the retentate chamber.

30. The process of claim 26, wherein the product concentration device further comprises a filtrate collection chamber surrounding the filter cartridge, and wherein the filter cartridge comprises a porous housing such that the pumping causes a waste stream to pass through the semi-permeable outer wall of at least one of the plurality of open-ended hollow fibers and through the porous housing of the filter cartridge thereby causing the waste stream to collect within the filtrate collection chamber.

31. The process of claim 26, further comprising harvesting the product stream from the reservoir.

32. The process of claim 26, wherein pumping the fluid into the fluid cartridge and into the retentate chamber further comprises causing the fluid to flow between the retentate chamber and the pump in a first direction and a second direction.

33. The process of claim 26, further comprising inserting at least one probe into an one or more port in the reservoir and monitoring the product stream using the at least one probe in the reservoir to determine one of more of the following: a fluid level, a pH level, a temperature, and a turbidity.

34. The process of claim 26, further comprising conditioning the product stream in the reservoir to stabilize the product stream in the reservoir, to facilitate a separation of the product stream, or to stabilize the product stream in the reservoir and facilitate a separation of the product stream.

* * * * *